(12) United States Patent
Bailey et al.

(10) Patent No.: US 7,772,155 B2
(45) Date of Patent: *Aug. 10, 2010

(54) FUNGAL ISOLATES AND BIOLOGICAL CONTROL COMPOSITIONS FOR THE CONTROL OF WEEDS

(75) Inventors: Karen L. Bailey, Saskatoon (CA); JoAnne Derby, Saskatoon (CA)

(73) Assignee: Her Majesty the Queen in right of Canada, as represented by the Minister of Agriculture and Agri-Food, Saskatoon (CA)

(*) Notice: Subject to any disclaimer, the term of this patent is extended or adjusted under 35 U.S.C. 154(b) by 988 days.

This patent is subject to a terminal disclaimer.

(21) Appl. No.: 11/190,078

(22) Filed: Jul. 25, 2005

(65) Prior Publication Data

US 2006/0084574 A1 Apr. 20, 2006

Related U.S. Application Data

(63) Continuation-in-part of application No. 10/478,829, filed as application No. PCT/CA02/00797 on May 30, 2002.

(60) Provisional application No. 60/294,475, filed on May 30, 2001.

(51) Int. Cl.
*A01N 63/00* (2006.01)
(52) U.S. Cl. .................... 504/116.1; 504/117
(58) Field of Classification Search ............... 435/910; 504/116.1, 117
See application file for complete search history.

(56) References Cited

U.S. PATENT DOCUMENTS

| | | | |
|---|---|---|---|
| 4,606,751 A | 8/1986 | Van Dyke et al. |
| 4,636,386 A | 1/1987 | Anderson et al. |
| 5,082,489 A | 1/1992 | Watson et al. |
| 5,391,538 A | 2/1995 | Heiny et al. |
| 5,472,690 A | 12/1995 | Winder |
| 5,635,444 A | 6/1997 | Walker et al. |
| 5,698,491 A | 12/1997 | Kadir et al. |
| 5,747,029 A | 5/1998 | Walker et al. |
| 5,795,845 A | 8/1998 | Yang et al. |
| 5,952,264 A | 9/1999 | Walker et al. |
| 5,993,802 A | 11/1999 | Mallett |
| 6,008,159 A | 12/1999 | Medd et al. |
| 6,403,530 B1 | 6/2002 | Sands et al. |
| 2006/0084574 A1 | 4/2006 | Bailey et al. |

FOREIGN PATENT DOCUMENTS

| | | |
|---|---|---|
| EP | 0 187 341 | 7/1986 |
| EP | 0 497 728 | 8/1992 |
| JP | 61-209507 | 9/1986 |
| JP | 61-210006 | 9/1986 |
| JP | 61210006 A * | 9/1986 |
| JP | 04-312508 | 11/1992 |
| JP | 2001-000012 | 1/2001 |
| WO | 98/08389 | 3/1998 |
| WO | WO 00/54568 | 9/2000 |
| WO | WO 02/096204 A1 | 12/2002 |

OTHER PUBLICATIONS

Graupner et al., 2003, *J. Nat. Prod.* 66: 1558-1561, "The Macrocidins: Novel Cyclic Tetramic Acids with Herbicidal Activity Produced by *Phoma macrostoma*".
Kothera et al., 2003, *Mycol. Res.* 107: 297-304, "AFLP analysis of a worldwide collection of *Didymella bryoniae*".
Larsen et al., 2002, *Plant Disease* 86: 928-932, "A Rapid Method Using PCR-Based SCAR Markers for the Detection and Identification of Phoma sclerotioides: The Cause of Brown Root Rot Disease of Alfalfa".
Voight et al., 1998, *J. Phytopathology* 146: 567-576, "RAPD-based Molecular Probes for the Blackleg Fungus *Leptosphaeria maculans* (Phoma lingam): Evidence for Pathogenicity Group-specific Sequences in the Fungal Genomes".
Vos et al., 1995, *Nucleic Acids Research* 23, "AFLP: a new technique for DNA fingerprinting".
Zhou et al., 2005, *Mycologia* 97, "Molecular and genetic analyses of geographic variation in isolates of *Phoma macrostoma* used for biological weed control".
Zhou et al., 2004, *Biological Control* 30, "Plant colonization and environmental fate of the biocontrol fungus *Phoma macrostoma*".
Chrysayi-Tokousbalides, M., "Phoma Metabolites Toxic to *Convolvulus* spp.", Phytopath. Medit. (1997); vol. 36: 19-23.
Connick et al., "An Improved Invert Emulsion with High Water Retention for Mycoherbicide Delivery", Weed Technology (1991); vol. 5: 442-444.
Connick, Jr. et al., "Applications Note, Shelf life of a bioherbicide product", American Biotechnology Laboratory (1996): 34-35.
Evidente et al., "Putaminoxin, A Phytotoxic Nonenolide From Phoma Putaminum", Photochemistry (1995); vol. 40, No. 6: 1637-1641.
Nyvall et al., "Laboratory Evaluation of Indigenous North American Fungi for Biological Control of Purple Loosestrife", Biological Control (1997); vol. 8: 37-42.

(Continued)

Primary Examiner—Tekchand Saidha
(74) Attorney, Agent, or Firm—Merchant & Gould P.C.

(57) ABSTRACT

The present invention discloses fungal isolates of *Phoma macrostoma* or extracts obtained therefrom, useful for the control of broad leaf weeds, including Canada thistle, perennial sowthistle, dandelion, scentless chamomile, false cleavers, chickweed, wild buckwheat, and field bindweed. The present invention also discloses biological control compositions comprising fungal isolates formulated in a growth medium for maintaining the viability of the fungal isolates when the biological control composition is applied to soil. The present invention also discloses a novel probe and primer pair sequence for use in detecting *Phoma macrostoma* isolates that exhibit biocontrol activity. The present invention also discloses methods of screening fungal isolates to determine if they exhibit biocontrol activity.

4 Claims, 31 Drawing Sheets

OTHER PUBLICATIONS

Venkatasubbaiah et al., "Phytotoxic Metabolites of *Phoma Sorghina*, A New Foliar Pathogen of Pokeweed", Mycologia (1992); vol. 84, No. 5: 715-723.

Williamson et al., "First Report of the Teleomorph of an *Oidium* sp. Causing Powdery Mildew on Flowering Dogwood in South Carolina", Agriculture and Natural Resources (1999); vol. 83: 200.

Agrios, G.N., "Plant Pathology," *Academic Press* $2^{nd}$ Edition, 1978, pp. 30-31, 90-93.

Gilbert et al., "Phylogenetic signal in plant pathogen—host range," PNAS (2007) 104 (12): 4979-4983.

Melzer et al., "Index of plant hosts of *Sclerotinia minor*," *Canadian Journal of Plant Pathology* (1997) 19: 272-280.

U.S. Department of Agriculture, Agricultural Research Service webpage on Phoma Proboscis, http://nt.ars.grin.gov/fungaldatabases/fungushost/new_hostFamGen.cfm, printed Sep. 4, 2007.

Wapshere, A.J., "A strategy for evaluating the safety of organisms for biological weed control," *Anm. Appl. Biol.* (1974) 77: 201-211.

Office Action for corresponding Mexican application 2008/001233 and English translation.

Notification of Reason for Refusal for corresponding Japanese application 2002-592726, dispatched on Feb. 3, 2009 (and English translation).

Restriction Requirement and Notice of References Cited by the Examiner for co-pending U.S. Appl. No. 10/478,829 mailed on Apr. 1, 2009.

Office Action for related Canadian Application 2,448,890 mailed Jul. 10, 2009.

Office Action for related Canadian Application 2,448,890 mailed on Oct. 8, 2008.

Office Action for related U.S. Appl. No. 10/478,829 mailed Mar. 14, 2006.

Office Action for related U.S. Appl. No. 10/478,829 mailed Jul. 11, 2007.

Office Action for related U.S. Appl. No. 10/478,829 mailed Nov. 7, 2007.

Office Action for related Australian Patent 2002311116 mailed Oct. 6, 2006.

Office Action for related Australian Patent 2002311116 mailed Oct. 3, 2007.

Office Action for related European Application 02734935.6 mailed on Feb. 20, 2007.

Office Action for related European Application 02734935.6 mailed on Mar. 25, 2008.

Office Action for related New Zealand Patent 529796 mailed on Apr. 11, 2005.

Office Action for related Mexican Application MX/a/2008/001233 mailed Apr. 27, 2009.

Office Action for related Mexican Application MX/a/2008/001233 mailed Aug. 18, 2009.

* cited by examiner

Plasmid DNA *pBluescript KSII* containing *probe*: 1370 bases in length:

(KpnI)

<u>GGTAC</u>

<u>C</u>GATCCCCGCAATACACCACGATTCTGGATGCGACAGGCAAGATTATCGCACCTGGATTCGTCGACACTCACCGTCATGGTTGGCAA
ACGTTTTTTAAGACCATGGTCTCAAACATCACTCTGATTGAGTATTTCGGCCGTTTCGGGGAGTCAGCTTCTGCAGGACGCATCAAT
GCTGAGCAAGTATACCTTGGTCAGCTCGCCGGCCTCTATGAATCAGTGAACACGGGAGTCACTACGACCGTTGATCACGCCCATCAC
ACTTGGTCAGATGAGACGTCCTGGGCTGGTCTAAACGCCAGTATAGACAGCGGTGCGCGCGTGTTCTGGTCTTACACCTTCCATGAA
GTTGCAAACTATACCATCGAGCAGCAACTCCAAAACTATCGCGACATTGTGAGCCGCGCCCCACAGGCAGGATCGGCTGCTGAGATC
GGAGTTGCTTTCGACAGCTTCGACAATGGCTCTGTTGATCTGGACACTATCACTGCGATCATAGACTTAGCTAAGTAAGTTTACTCG
TTACTCACCTTATGATTCAAGGTATACATTGTTTTAGTTAGTCTAACGTTGTGTGTTTAGAGAATCAAATGCCTCGGTTATCACAAC
CCACGGTGGAGGAGGTGTCTATGGAAGTAGGTGACCCGATGTCC*TTTTGTTTTGTTTG*AGACCGCACTCTTGAACAATGGGAACTGA
CCAAAATCTGCAGACGACAATTCTCCTTCGACCCTACAGTCCCTTGGCATTCTCAACACAAGCATTCCTGTCGTTATCTCTCACGCG
ACGTACGTGACTTTGCGGGACACAATGCTGTTGCGCGAGACAAATCAGTTCGTTTCTATCACGCCCGAGTCAGAGATGGGGTTCGGC
CTCGGACGGCCGACGAGCAACATGATCATTGACCAAGCCTCCTTAGGTGTTGATTCACACGCCTTTGCTTCTAGTGATCTAGTATCC
CAGGCGCGCTTGTTTCTTCAGAGTACGCGGTCAGCAGTCACCGATCAACTCTTCAAGAAATGGCAGGCTCCTAAGTCGAACCCTATG
AGTGTCGTTCAGGCTTTTCTCCTTAGCACACGTAACGGAGGCCTTGCACTTCGCCGCCCAGACCTTGGTGTTCTCAGTGTCGGCGCT
AAAGCTGACGTTGTGGTGTGGGACGGGACCAGTCCGAGCCTGCTGGGCTGGCGTGATCCTGTGGCCGCAATCATCCAGCACTCCAAT
GTCGGCGATGTTGAGCATGTTCTCATCGATGGCAAATTTGTGAAAAGAGATCACAAGCTGGTTGTTGGGAACTACGCGAATGTAAAG
TCTCGGTTCCTGGAAGTCGCAAACCGCATCCAGGAGGACTGGGAGCTGATCCCCCGTCCC<u>GAGCT</u>

<u>C</u>

(SacI)

FIG. 9

```
OLIGO    start len  tm    gc%   any  primer3 www results help.cgi-PRIMER THREE 3' seq
LEFT PRIMER   449   20  60.02  50.00  4.00  1.00  ACAGCTTCGACAATGGCTCT
RIGHT PRIMER 1301   20  60.00  50.00  4.00  3.00  ACATTCGCGTAGTTCCCAAC
SEQUENCE SIZE: 1370; INCLUDED REGION SIZE: 1370
PRODUCT SIZE: 853, PAIR ANY COMPL: 5.00, PAIR 3' COMPL: 0.00

1 CGATCCCCGCAATACACCACGATTCTGGATGCGACAGGCAAGATTATCGCACCTGGATTC
   61 GTCGACACTCACCGTCATGGTTGGCAAACGTTTTTTAAGACCATGGTCTCAAACATCACT
  121 CTGATTGAGTATTTCGGCCGTTTCGGGGAGTCAGCTTCTGCAGGACGCATCAATGCTGAG
  181 CAAGTATACCTTGGTCAGCTCGCCGGCCTCTATGAATCAGTGAACACGGGAGTCACTACG
  241 ACCGTTGATCACGCCCATCACACTTGGTCAGATGAGACGTCCTGGGCTGGTCTAAACGCC
  301 AGTATAGACAGCGGTGCGCGCGTGTTCTGGTCTTACACCTTCCATGAAGTTGCAAACTAT
  361 ACCATCGAGCAGCAACTCCAAAACTATCGCGACATTGTGAGCCGCGCCCCACAGGCAGGA
  421 TCGGCTGCTGAGATCGGAGTTGCTTTCGACAGCTTCGACAATGGCTCTGTTGATCTGGAC
                                  >>>>>>>>>>>>>>>>>>>>
  481 ACTATCACTGCGATCATAGACTTAGCTAAGTAAGTTTACTCGTTACTCACCTTATGATTC
  541 AAGGTATACATTGTTTTAGTTAGTCTAACGTTGTGTGTTTAGAGAATCAAATGCCTCGGT
  601 TATCACAACCCACGGTGGAGGAGGTGTCTATGGAAGTAGGTGACCCGATGTCCTTTTGTT
  661 TTGTTTGAGACCGCACTCTTGAACAATGGGAACTGACCAAAATCTGCAGACGACAATTCT
  721 CCTTCGACCCTACAGTCCCTTGGCATTCTCAACACAAGCATTCCTGTCGTTATCTCTCAC
  781 GCGACGTACGTGACTTTGCGGGACACAATGCTGTTGCGCGAGACAAATCAGTTCGTTTCT
  841 ATCACGCCCGAGTCAGAGATGGGGTTCGGCCTCGGACGGCCGACGAGCAACATGATCATT
  901 GACCAAGCCTCCTTAGGTGTTGATTCACACGCCTTTGCTTCTAGTGATCTAGTATCCCAG
  961 GCGCGTTGTTTCTTCAGAGTACGCGGTCAGCAGTCACCGATCAACTCTTCAAGAAATGG
 1021 CAGGCTCCTAAGTCGAACCCTATGAGTGTCGTTCAGGCTTTTCTCCTTAGCACACGTAAC
 1081 GGAGGCCTTGCACTTCGCCGCCCAGACCTTGGTGTTCTCAGTGTCGGCGCTAAAGCTGAC
 1141 GTTGTGGTGTGGGACGGGACCAGTCCGAGCCTGCTGGGCTGGCGTGATCCTGTGGCCGCA
 1201 ATCATCCAGCACTCCAATGTCGGCGATGTTGAGCATGTTCTCATCGATGGCAAATTTGTG
 1261 AAAAGAGATCACAAGCTGGTTGTTGGGAACTACGCGAATGTAAAGTCTCGGTTCCTGGAA
                                   <<<<<<<<<<<<<<<<<<<<
 1321 GTCGCAAACCGCATCCAGGAGGACTGGGAGCTGATCCCCCGTCCCGAGCT
KEYS (in order of precedence):>>>>>> left primer, <<<<<< right primer
```

FIG. 10

|          | 10 | 20 | 30 | 40 | 50 | 60 | 70 | 80 |
|----------|----|----|----|----|----|----|----|----|
|          | ....\|....\| | ....\|....\| | ....\|....\| | ....\|....\| | ....\|....\| | ....\|....\| | ....\|....\| | ....\|....\| |
| ATCC24524 | TTTCCGTAGG | TGAACCTGCG | GAAGGATCAT | TACCTAGAGT | T-GTAGGCTT | TGCCTGCTAT | CTCTTACCCA | TGTCTTTTGA |
| ATCC46580 | .......... | .......... | .......... | .......... | .-.CG..... | ......C... | .......... | .......... |
| CBS112.36 | .......... | .......... | .......... | .......... | .-........ | .......... | .......... | .......... |
| CBS115.12 | .......... | .......... | .......... | .......... | .-........ | .......... | .......... | .......A. |
| CBS154.83 | .......... | .......... | .......... | .......... | .-........ | .......... | .......... | .......... |
| CBS185.25 | .......... | .......... | .......... | .......... | .-........ | .......... | .......... | .......... |
| CBS198.69 | .......... | .......... | .......... | .......... | .-........ | .......... | .......... | .......... |
| CBS223.69 | .......... | .......... | .......... | .......... | .-........ | .......... | .......... | .......... |
| CBS297.36 | .......... | .......... | .......... | .......... | .-........ | .......... | .......... | .......... |
| CBS300.36 | ......C... | .......... | .......... | .......... | .-........ | .......... | .......... | .......... |
| CBS345.97 | .......... | .......... | .......... | .......... | .-........ | .......... | .......... | .......... |
| CBS371.61 | .......... | .......... | .......... | .......... | .-........ | .......... | .......... | .......... |
| CBS482.95 | .......... | .......... | .......... | .......... | .-........ | .......... | .......... | .......... |
| CBS483.66 | .......... | .......... | .......... | .......... | .-........ | .......... | .......... | .......... |
| CBS488.94 | .......... | .......... | .......... | .......... | .-........ | .......... | .......... | .......... |
| CBS529.66 | .......... | .......... | .......... | .......... | .-........ | .......... | .......... | .......... |
| CBS560.70 | .......... | .......... | .......... | .......... | .-........ | .......... | .......... | .......... |
| CBS598.94 | .......... | .......... | .......... | .......... | .-........ | .......... | .......... | .......... |
| CBS837.84 | .......... | .......... | .......... | .......... | .-........ | .......... | .......... | .......... |
| CBS839.84 | .......... | .......... | .......... | .......... | .-........ | .......... | .......... | .......... |
| CCM-F322 | .......... | .......... | .......... | .......... | .-........ | .......... | .......... | .......... |
| CCM-F323 | .......... | .......... | .......... | .......... | .-........ | .......... | .......... | .......... |
| DAOM175135 | .......... | .......... | .......... | .......... | .T..G..... | ...C....C. | .......... | .......... |
| DAOM175940 | .......... | .......... | .......... | .......... | .-.CG....C | .......C.. | .......... | .......... |
| DAOM175951 | .......... | .......... | .......... | .......... | .-........ | .......... | .......... | .......... |
| ICMP10843 | .......... | .......... | .......... | .......... | .-.CG..... | .......C.. | .......... | ........C |
| ICMP10963 | .......... | .......... | .......... | .......... | .-........ | .......... | .......... | .......... |
| ICMP11186 | .......... | .......... | .......... | .......... | .-........ | .......... | .......... | .......... |
| ICMP12948 | .......... | .......... | .......... | .......... | .-........ | .......... | .......... | .......A. |
| ICMP2325 | .......... | .......... | .......... | .......... | .-........ | .......... | .......... | .......... |
| ICMP2715 | .......... | .......... | .......... | .......... | .-........ | .......... | .......... | .......... |
| ICMP3173 | .......... | .......... | .......... | .......... | .-........ | .......... | .......... | .......... |
| ICMP6603 | .......... | .......... | .......... | .......... | .-........ | .......... | .......... | .......... |
| ICMP6628 | .......... | .......... | .......... | .......... | .-........ | .......... | .......... | .......... |
| ICMP6803 | .......... | .......... | .......... | .......... | .-........ | .......... | .......... | .......... |
| ICMP6814 | .......... | .......... | .......... | .......... | .-........ | .......... | .......... | .......... |
| ICMP7033 | .......... | .......... | .......... | .......... | .-........ | .......... | .......... | .......... |
| IMI118020 | .......... | .......... | .......... | .......... | .-........ | .......... | .......... | .......... |
| IMI175661 | .......... | .......... | .......... | .......... | .-........ | .......... | .......... | .......... |
| IMI192267 | .......... | .......... | .......... | .......... | .-........ | .......... | .......... | .......... |
| IMI192268 | G.......T C........ | .......... | .......... | .......... | .-........ | .......... | .......... | .......... |
| IMI299239 | .......... | .......... | .......... | .......... | .-........ | .......... | .......... | .......... |
| IMI336757 | .......... | .......... | .......... | .......... | .-........ | .......... | .......... | .......... |
| IMI336761 | .......... | .......... | .......... | .......... | .-.CG..... | .......C.. | .......... | .......... |
| MA1908B | .......... | .......... | .......... | .......... | .-........ | .......... | .......... | .......... |
| MA3312 | .......... | .......... | .......... | .......... | .-........ | .......... | .......... | .......... |
| SCR97-15B2 | .......... | .......... | .......... | .......... | .-.CG....C | .......C.. | .......... | .......... |
| SRC02-2A | .......... | .......... | .......... | .......... | .-.CG....C | .......C.. | .......... | .......... |
| SRC03-1A8 | .......... | .......... | .......... | .......... | .-.CG....C | .......C.. | .......... | .......... |
| SRC85-24B | .......... | .......... | .......... | .......... | .-.CG....C | .......C.. | .......... | .......... |
| SRC89-25A2 | .......... | .......... | .......... | .......... | .-.CG....C | .......C.. | .......... | .......... |
| SRC94-134 | .......... | .......... | .......... | .......... | .-.CG....C | .......C.. | .......... | .......... |
| SRC94-26 | .......... | .......... | .......... | .......... | .-.CG....C | .......C.. | .......... | .......... |
| SRC94-26A | .......... | .......... | .......... | .......... | .-........ | .......... | .......... | .......... |
| SRC94-359A | .......... | .......... | .......... | .......... | .-.CG....C | .......C.. | .......... | .......... |
| SRC94-44B | .......... | .......... | .......... | .......... | .-.CG....C | .......C.. | .......... | .......... |
| SRC95-268B | .......... | .......... | .......... | .......... | .-.CG....C | .......C.. | .......... | .......... |
| SRC95-54A1 | .......... | .......... | .......... | .......... | .-.CG....C | .......C.. | .......... | .......... |
| SRC95-54A2 | .......... | .......... | .......... | .......... | ...CG....C | .......C.. | .......... | .......... |
| SRC97-12B | .......... | .......... | .......... | .......... | .-.CG....C | .......C.. | .......... | .......... |
| WAC7788 | .......... | .......... | .......... | .......... | .-........ | .....A.C.. | .......... | .......... |
| WAC7881 | .......... | .......... | .......... | .......... | .-........ | .......... | .......... | .......... |

|            | 170        | 180        | 190        | 200        | 210        | 220        | 230        | 240        |
|------------|------------|------------|------------|------------|------------|------------|------------|------------|
| ATCC24524  | AACATAATAG | TTACAACTTT | CAACAACGGA | TCTCTTGGTT | CTGGCATCGA | TGAAGAACGC | AGCGAAATGC | GATAAGTAGT |
| ATCC46580  | ...T...... | .......... | .......... | .......... | .......... | .......... | .......... | .......... |
| CBS112.36  | .......... | .......... | .......... | .......... | .......... | .......... | .......... | .......... |
| CBS115.12  | ...T...... | .......... | .......... | .......... | .......... | .......... | .......... | .......... |
| CBS154.83  | .......... | .......... | .......... | .......... | .......... | .......... | .......... | .......... |
| CBS185.25  | .......... | .......... | .......... | .......... | .......... | .......... | .......... | .......... |
| CBS198.69  | .......... | .......... | .......... | .......... | .......... | .......... | .......... | .......... |
| CBS223.69  | .......... | .......... | .......... | .......... | .......... | .......... | .......... | .......... |
| CBS297.36  | .......... | .......... | .......... | .......... | .......... | .......... | .......... | .......... |
| CBS300.36  | ...T...... | .......... | .......... | .......... | .......... | .......... | .......... | .......... |
| CBS345.97  | .......... | .......... | .......... | .......... | .......... | .......... | .......... | .......... |
| CBS371.61  | .......... | .......... | .......... | .......... | .......... | .......... | .......... | .......... |
| CBS482.95  | .......... | .......... | .......... | .......... | .......... | .......... | .......... | .......... |
| CBS483.66  | .......... | .......... | .......... | .......... | .......... | .......... | .......... | .......... |
| CBS488.94  | .......... | .......... | .......... | .......... | .......... | .......... | .......... | .......... |
| CBS529.66  | .......... | .......... | .......... | .......... | .......... | .......... | .......... | .......... |
| CBS560.70  | .......... | .......... | .......... | .......... | .......... | .......... | .......... | .......... |
| CBS598.94  | .......... | .......... | .......... | .......... | .......... | .......... | .......... | .......... |
| CBS837.84  | .......... | .......... | .......... | .......... | .......... | .......... | .......... | .......... |
| CBS839.84  | .......... | .......... | .......... | .......... | .......... | .......... | .......... | .......... |
| CCM-F322   | .......... | .......... | .......... | .......... | .......... | .......... | .......... | .......... |
| CCM-F323   | .......... | .......... | .......... | .......... | .......... | .......... | .......... | .......... |
| DAOM175135 | .-........ | .......... | .......... | .......... | .......... | .......... | .......... | .......... |
| DAOM175940 | ...T...... | .......... | .......... | .......... | .......... | .......... | .......... | .......... |
| DAOM175951 | .......... | .......... | .......... | .......... | .......... | .......... | .......... | .......... |
| ICMP10843  | .-......A. | .......... | .......... | .......... | .......... | .......... | .......... | .......... |
| ICMP10963  | .......... | .......... | .......... | .......... | .......... | .......... | .......... | .......... |
| ICMP11186  | .......... | .......... | .......... | .......... | .......... | .......... | .......... | .......... |
| ICMP12948  | ...T...... | .......... | .......... | .......... | .......... | .......... | .......... | .......... |
| ICMP2325   | .......... | .......... | .......... | .......... | .......... | .......... | .......... | .......... |
| ICMP2715   | .......... | .......... | .......... | .......... | .......... | .......... | .......... | .......... |
| ICMP3173   | .......... | .......... | .......... | .......... | .......... | .......... | .......... | .......... |
| ICMP6603   | .......... | .......... | .......... | .......... | .......... | .......... | .......... | .......... |
| ICMP6628   | .......... | .......... | .......... | .......... | .......... | .......... | .......... | .......... |
| ICMP6803   | .......... | .......... | .......... | .......... | .......... | .......... | .......... | .......... |
| ICMP6814   | .......... | .......... | .......... | .......... | .......... | .......... | .......... | .......... |
| ICMP7033   | .......... | .......... | .......... | .......... | .......... | .......... | .......... | .......... |
| IMI118020  | .......... | .......... | .......... | .......... | .......... | .......... | .......... | .......... |
| IMI175661  | .......... | .......... | .......... | .......... | .......... | .......... | .......... | .......... |
| IMI192267  | ...T...... | .......... | .......... | .......... | .......... | .......... | .......... | .......... |
| IMI192268  | ...T...... | .......... | .......... | .......... | .......... | .......... | .......... | .......... |
| IMI299239  | .......... | .......... | .......... | .......... | .......... | .......... | .......... | .......... |
| IMI336757  | ...T...... | .......... | .......... | .......... | .......... | .......... | .......... | .......... |
| IMI336761  | ...T...... | .......... | .......... | .......... | .......... | .......... | .......... | .......... |
| MA1908B    | .......... | .......... | .......... | .......... | .......... | .......... | .......... | .......... |
| MA3312     | .......... | .......... | .......... | .......... | .......... | .......... | .......... | .......... |
| SCR97-15B2 | ...T...... | .......... | .......... | .......... | .......... | .......... | .......... | .......... |
| SRC02-2A   | ...T...... | .......... | .......... | .......... | .......... | .......... | .......... | .......... |
| SRC03-1A8  | ...T...... | .......... | .......... | .......... | .......... | .......... | .......... | .......... |
| SRC85-24B  | ...T...... | .......... | .......... | .......... | .......... | .......... | .......... | .......... |
| SRC89-25A2 | ...T...... | .......... | .......... | .......... | .......... | .......... | .......... | .......... |
| SRC94-134  | ...T...... | .......... | .......... | .......... | .......... | .......... | .......... | .......... |
| SRC94-26   | ...T...... | .......... | .......... | .......... | .......... | .......... | .......... | .......... |
| SRC94-26A  | ...T...... | .......... | .......... | .......... | .......... | .......... | .......... | .......... |
| SRC94-359A | ...T...... | .......... | .......... | .......... | .......... | .......... | .......... | .......... |
| SRC94-44B  | ...T...... | .......... | .......... | .......... | .......... | .......... | .......... | .......... |
| SRC95-268B | ...T...... | .......... | .......... | .......... | .......... | .......... | .......... | .......... |
| SRC95-54A1 | ...T...... | .......... | .......... | .......... | .......... | .......... | .......... | .......... |
| SRC95-54A2 | ...T...... | .......... | .......... | .......... | .......... | .......... | .......... | .......... |
| SRC97-12B  | ...T...... | .......... | .......... | .......... | .......... | .......... | .......... | .......... |
| WAC7788    | .......... | .......... | .......... | .......... | .......... | .......... | .......... | .......... |
| WAC7881    | ...T...... | .......... | .......... | .......... | .......... | .......... | .......... | .......... |

FIG. 19A-3

```
                         250        260        270        280        290        300        310        320
                    ....|....| ....|....| ....|....| ....|....| ....|....| ....|....| ....|....| ....|....|
ATCC24524           GTGAATTGCA GAATTCAGTG AATCATCGAA TCTTTGAACG CACATTGCGC CCCTTGGTAT TCCATGGGGC ATGCCTGTTC
ATCC46580           .......... .......... .......... .......... .......... .......... .......... ..........
CBS112.36           .......... .......... .......... .......... .......... .......... .......... ..........
CBS115.12           .......... .......... .......... .......... .......... .......... .......... ..........
CBS154.83           .......... .......... .......... .......... .......... .......... .......... ..........
CBS185.25           .......... .......... .......... .......... .......... .......... .......... ..........
CBS198.69           .......... .......... .......... .......... .......... .......... .......... ..........
CBS223.69           .......... .......... .......... .......... .......... .......... .......... ..........
CBS297.36           .......... .......... .......... .......... .......... .......... .......... ..........
CBS300.36           .......... .......... .......... .......... .......... .......... .......... ..........
CBS345.97           .......... .......... .......... .......... .......... .......... .......... ..........
CBS371.61           .......... .......... .......... .......... .......... .......... .......... ..........
CBS482.95           .......... .......... .......... .......... .......... .......... .......... ..........
CBS483.66           .......... .......... .......... .......... .......... .......... .......... ..........
CBS488.94           .......... .......... .......... .......... .......... .......... .......... ..........
CBS529.66           .......... .......... .......... .......... .......... .......... .......... ..........
CBS560.70           .......... .......... .......... .......... .......... .......... .......... ..........
CBS598.94           .......... .......... .......... .......... .......... .......... .......... ..........
CBS837.84           .......... .......... .......... .......... .......... .......... .......... ..........
CBS839.84           .......... .......... .......... .......... .......... .......... .......... ..........
CCM-F322            .......... .......... .......... .......... .......... .......... .......... ..........
CCM-F323            .......... .......... .......... .......... .......... .......... .......... ..........
DAOM175135          .......... .......... .......... .......... .......... .......... .......... ..........
DAOM175940          .......... .......... .......... .......... .......... .......... .......... ..........
DAOM175951          .......... .......... .......... .......... .......... .......... .......... ..........
ICMP10843           .......... .......... .......... .......... .......... .......... .......... ..........
ICMP10963           .......... .......... .......... .......... .......... .......... .......... ..........
ICMP11186           .......... .......... .......... .......... .......... .......... .......... ..........
ICMP12948           .......... .......... .......... .......... .......... .......... .......... ..........
ICMP2325            .......... .......... .......... .......... .......... .......... .......... ..........
ICMP2715            .......... .......... .......... .......... .......... .......... .......... ..........
ICMP3173            .......... .......... .......... .......... .......... .......... .......... ..........
ICMP6603            .......... .......... .......... .......... .......... .......... .......... ..........
ICMP6628            .......... .......... .......... .......... .......... .......... .......... ..........
ICMP6803            .......... .......... .......... .......... .......... .......... .......... ..........
ICMP6814            .......... .......... .......... .......... .......... .......... .......... ..........
ICMP7033            .......... .......... .......... .......... .......... .......... .......... ..........
IMI118020           .......... .......... .......... .......... .......... .......... .......... ..........
IMI175661           .......... .......... .......... .......... .......... .......... .......... ..........
IMI192267           .......... .......... .......... .......... .......... .......... .......... ..........
IMI192268           .......... .......... .......... .......... .......... .......... .......... ..........
IMI299239           .......... .......... .......... .......... .......... .......... .......... ..........
IMI336757           .......... .......... .......... .......... .......... .......... .......... ..........
IMI336761           .......... .......... .......... .......... .......... .......... .......... ..........
MA1908B             .......... .......... .......... .......... .......... .......... .......... ..........
MA3312              .......... .......... .......... .......... .......... .......... .......... ..........
SCR97-15B2          .......... .......... .......... .......... .......... .......... .......... ..........
SRC02-2A            .......... .......... .......... .......... .......... .......... .......... ..........
SRC03-1A8           .......... .......... .......... .......... .......... .......... .......... ..........
SRC85-24B           .......... .......... .......... .......... .......... .......... .......... ..........
SRC89-25A2          .......... .......... .......... .......... .......... .......... .......... ..........
SRC94-134           .......... .......... .......... .......... .......... .......... .......... ..........
SRC94-26            .......... .......... .......... .......... .......... .......... .......... ..........
SRC94-26A           .......... .......... .......... .......... .......... .......... .......... ..........
SRC94-359A          .......... .......... .......... .......... .......... .......... .......... ..........
SRC94-44B           .......... .......... .......... .......... .......... .......... .......... ..........
SRC95-268B          .......... .......... .......... .......... .......... .......... .......... ..........
SRC95-54A1          .......... .......... .......... .......... .......... .......... .......... ..........
SRC95-54A2          .......... .......... .......... .......... .......... .......... .......... ..........
SRC97-12B           .......... .......... .......... .......... .......... .......... .......... ..........
WAC7788             .......... .......... .......... .......... .......... .......... .......... ..........
WAC7881             .......... .......... .......... .......... .......... .......... .......... ..........
```

FIG. 19A-4

```
                    330        340        350        360        370        380        390        400
                ....|....| ....|....| ....|....| ....|....| ....|....| ....|....| ....|....| ....|....|
ATCC24524       GAGCGTCATT TGTACCTTCA AGCTCTGCTT GGTGTTGGGT GTTTGTCTCG CCTCTGCGTG TAGACTCGCC TCAAAACAAT
ATCC46580       .......... ....T..... .......... .......... .......... ........C. C......... ..........
CBS112.36       .......... .......... .......... .......... .......... .......... .......... ..........
CBS115.12       .......... .......... .......... .......... .......... .......... .......... ..........
CBS154.83       .......... .......... .......... .......... .......... .......... .......... ..........
CBS185.25       .......... .......... .......... .......... .......... .......... .......... ..........
CBS198.69       .......... .......... .......... .......... .......... .......... .......... ..........
CBS223.69       .......... .......... .......... .......... .......... .......... .......... ..........
CBS297.36       .......... .......... .......... .......... .......... .......... .......... ..........
CBS300.36       .......... .......... .......... .......... .......... ........C. .......... ..G.......
CBS345.97       .......... .......... .......... .......... .......... .......... .......... ..........
CBS371.61       .......... .......... .......... .......... .......... .......... .......... ..........
CBS482.95       .......... .......... .......... .......... .......... .......... .......... ..........
CBS483.66       .......... .......... .......... .......... .......... .......... .......... ..........
CBS488.94       .......... .......... .......... .......... .......... .......... .......... ..........
CBS529.66       .......... .......... .......... .......... .......... .......... .......... ..........
CBS560.70       .......... .......... .......... .......... .......... .......... .......... ..........
CBS598.94       .......... .......... .......... .......... .......... .......... .......... ..........
CBS837.84       .......... .......... .......... .......... .......... .......... .......... ..........
CBS839.84       .......... .......... .......... .......... .......... .......... .......... ..........
CCM-F322        .......... .......... .......... .......... .......... .......... .......... ..........
CCM-F323        .......... .......... .......... .......... .......... .......... .......... ..........
DAOM175135      .......... .......... .......... .......... .......... .......... .......... .T........
DAOM175940      .......... ...CT..... .......... .......... .......... ........C. C......... ..........
DAOM175951      .......... .......... .......... .......... .......... .......... .......... ..........
ICMP10843       .......... ....T..... .......... .......... .......... .......... .......... .T........
ICMP10963       .......... .......... .......... .......... .......... .......... .......... ..........
ICMP11186       .......... .......... .......... .......... .......... .......... .......... ..........
ICMP12948       .......... .......... .......... .......... .......... .......... .......... ..........
ICMP2325        .......... .......... .......... .......... .......... .......... .......... ..........
ICMP2715        .......... .......... .......... .......... .......... .......... .......... ..........
ICMP3173        .......... .......... .......... .......... .......... .......... .......... ..........
ICMP6603        .......... .......... .......... .......... .......... .......... .......... ..........
ICMP6628        .......... .......... .......... .......... .......... .......... .......... ..........
ICMP6803        .......... .......... .......... .......... .......... .......... .......... ..........
ICMP6814        .......... ...CT..... .......... .......... .......... ......C... .......... ..........
ICMP7033        .......... .......... .......... .......... .......... .......... .......... ..........
IMI118020       .......... .......... .......... .......... .......... .......... .......... ..........
IMI175661       .......... .......... .......... .......... .......... .......... .......... ..........
IMI192267       .......... .......... .......... .......... .......... ........C. .......... ..........
IMI192268       .......... .......... .......... .......... .......... ........C. .......... ..........
IMI299239       .......... .......... .......... .......... .......... .......... .......... ..........
IMI336757       .......... .......... .......... .......... ........C ---------. .......... .T........
IMI336761       .......... .......... .......... .......... .......... ........C. C......... ..........
MA1908B         .......... .......... .......... .......... .......... .......... .......... ..........
MA3312          .......... .......... .......... .......... .......... .......... .......... ..........
SCR97-15B2      .......... ...CT..... .......... .......... .......... ........C. C......... ..........
SRC02-2A        .......... ...CT..... .......... .......... .......... ........C. C......... ..........
SRC03-1A8       .......... ...CT..... .......... .......... .......... ........C. C......... ..........
SRC85-24B       .......... ...CT..... .......... .......... .......... ........C. C......... ..........
SRC89-25A2      .......... ...CT..... .......... .......... .......... ........C. C......... ..........
SRC94-134       .......... ...CT..... .......... .......... .......... ........C. C......... ..........
SRC94-26        .......... ...CT..... .......... .......... .......... ........C. C......... ..........
SRC94-26A       .......... .......... .......... .......... .......... ........C. .......... ..........
SRC94-359A      .......... ...CT..... .......... .......... .......... ........C. C......... ..........
SRC94-44B       .......... ...CT..... .......... .......... .......... ........C. C......... ..........
SRC95-268B      .......... ...CT..... .......... .......... .......... ........C. C......... ..........
SRC95-54A1      .......... ...CT..... .......... .......... .......... ........C. C......... ..........
SRC95-54A2      .......... ...CT..... .......... .......... .......... ........C. C......... ..........
SRC97-12B       .......... ...CT..... .......... .......... .......... ........C. C......... ..........
WAC7788         .......... .......... .......... .......... .......... ......T... .......... .T........
WAC7881         .......... ....T..... .......... .......... .......... ........C. C......... ..........
```

FIG. 19A-5

```
                410        420        430        440        450        460        470        480
           ....|....|....|....|....|....|....|....|....|....|....|....|....|....|....|....|
ATCC24524  TGGCAGCCGG CGTATTGATT TCGGAGCGCA GTACATCTCG CGCTTTGCAC TCAGAACGAC GACGTCCAAA AGTACATTTT
ATCC46580  .......... .......... .......... .......... .......... .......... .......... ..........
CBS112.36  .......... .......... .......... .......... .......... .......... .......... ..........
CBS115.12  .......... .......... .......... .......... .......... ...T...... .......... ..........
CBS154.83  .......... .......... .......... .......... .......... .......... .......... ..........
CBS185.25  .......... .......... .......... .......... .......... .......... .......... ..........
CBS198.69  .......... .......... .......... .......... .......... .......... .......... ..........
CBS223.69  .......... .......... .......... .......... .......... .......... .......... ..........
CBS297.36  .......... .......... .......... .......... .......... .......... .......... ..........
CBS300.36  .......... .......... .......... .......... ....C..... ...T...... .......... ..........
CBS345.97  .......... .......... .......... .......... .......... .......... .......... ..........
CBS371.61  .......... .......... .......... .......... .......... .......... .......... ..........
CBS482.95  .......... .......... .......... .......... .......... .......... .......... ..........
CBS483.66  .......... .......... .......... .......... .......... .......... .......... ..........
CBS488.94  .......... .......... .......... .......... .......... .......... .......... ..........
CBS529.66  .......... .......... .......... .......... .......... .......... .......... ..........
CBS560.70  .......... .......... .......... .......... .......... .......... .......... ..........
CBS598.94  .......... .......... .......... .......... .......... .......... .......... ..........
CBS837.84  .......... .......... .......... .......... .......... .......... .......... ..........
CBS839.84  .......... .......... .......... .......... .......... .......... .......... ..........
CCM-F322   .......... .......... .......... .......... .......... .......... .......... ..........
CCM-F323   .......... .......... .......... .......... .......... .......... .......... ..........
DAOM175135 .......... .......... .......... .......... .......... ...T...... .......... ..........
DAOM175940 .......... .......... .......... .......... .......... ...CC...G. .G........ ..........
DAOM175951 .......... .......... .......... .......... .......... .......... .......... ..........
ICMP10843  .......... ........T. .......... .C...AT.T. .......T.. ...T...... .G.A...... ...CAT..C.
ICMP10963  .......... .......... .......... .......... .......... .......... .......... ..........
ICMP11186  .......... .......... .......... .......... .......... .......... .......... ..........
ICMP12948  .......... .......... .......... .......... .......... ...T...... .......... ..........
ICMP2325   .......... .......... .......... .......... .......... .......... .......... ..........
ICMP2715   .......... .......... .......... .......... .......... .......... .......... ..........
ICMP3173   .......... .......... .......... .......... .......... .......... .......... ..........
ICMP6603   .......... .......... .......... .......... .......... .......... .......... ..........
ICMP6628   .......... .......... .......... .......... .......... .......... .......... ..........
ICMP6803   .......... .......... .......... .......... .......... .......... .......... ..........
ICMP6814   .......... .......... .......... .......... ........T. .......... .......... ..........
ICMP7033   .......... .......... .......... .......... .......... .......... .......... ..........
IMI118020  .......... .......... .......... .......... .......... .......... .......... ..........
IMI175661  .......... .......... .......... .......... .......... .......... .......... ..........
IMI192267  .......... .......... .......... .......... .......... ...T...... .......... ..........
IMI192268  .......... .......... .......... .......... .......... ...T...... .......... ..........
IMI299239  .......... .......... .......... .......... .......... .......... .......... ..........
IMI336757  .......... .......... .......... .......... .......... ...T...... ...A...... ..........
IMI336761  .......... .......... .......... .......... .......... .......... .......... ..........
MA1908B    .......... .......... .......... .......... .......... .......... .......... ..........
MA3312     .......... .......... .......... .......... .......... .......... .......... ..........
SCR97-15B2 .......... .......... .......... .......... .......... ...CC...G. .G........ ..........
SRC02-2A   .......... .......... .......... .......... .......... ...CC...G. .G........ ..........
SRC03-1A8  .......... .......... .......... .......... .......... ...CC...G. .G........ ..........
SRC85-24B  .......... .......... .......... .......... .......... ...CC...G. .G........ ..........
SRC89-25A2 .......... .......... .......... .......... .......... ...CC...G. .G........ ..........
SRC94-134  .......... .......... .......... .......... .......... ...CC...G. .G........ ..........
SRC94-26   .......... .......... .......... .......... .......... ...CC...G. .G........ ..........
SRC94-26A  .......... .......... .......... .......... .......... ...T...... .......... ...T....
SRC94-359A .......... .......... .......... .......... .......... ...CC...G. .G........ ..........
SRC94-44B  .......... .......... .......... .......... .......... ...CC...G. .G........ ..........
SRC95-268B .......... .......... .......... .......... .......... ...CC...G. .G........ ..........
SRC95-54A1 .......... .......... .......... .......... .......... ...CC...G. .G........ ..........
SRC95-54A2 .......... .......... .......... .......... .......... ...CC...G. .G........ ..........
SRC97-12B  .......... .......... .......... .......... .......... ...CC...G. .G........ ..........
WAC7788    .......... .......... .......... .......... .......... ...T...... .......... .AGTAC....
WAC7881    .......... .......... .......... .......... .A..C...CT ...T...... .G........ ..........
```

FIG. 19A-6

```
                         490        500        510        520
                    ....|....|....|....|....|....|....|....|....|
ATCC24524           TACACTCTTG ACCTCGGATC AGGTAGGGAT ACCCGCTGAA CTTAA
ATCC46580           .......... .......... .......... .......... .....
CBS112.36           .......... .......... .......... .......... .....
CBS115.12           .......... .......... .......... .......... .....
CBS154.83           .......... .......... .......... .......... .....
CBS185.25           .......... .......... .......... .......... .....
CBS198.69           .......... .......... .......... .......... .....
CBS223.69           .......... .......... .......... .......... .....
CBS297.36           .......... .......... .......... .......... .....
CBS300.36           .......... .......... .......... .......... .....
CBS345.97           .......... .......... .......... .......... .....
CBS371.61           .......... .......... .......... .......... .....
CBS482.95           .......... .......... .......... .......... .....
CBS483.66           .......... .......... .......... .......... .....
CBS488.94           .......... .......... .......... .......... .....
CBS529.66           .......... .......... .......... .......... .....
CBS560.70           .......... .......... .......... .......... .....
CBS598.94           .......... .......... .......... .......... .....
CBS837.84           .......... .......... .......... .......... .....
CBS839.84           .......... .......... .......... .......... .....
CCM-F322            .......... .......... .......... .......... .....
CCM-F323            .......... .......... .......... .......... .....
DAOM175135          .......... .......... .......... .......... .....
DAOM175940          .......... .......... .......... .......... .....
DAOM175951          .......... .......... .......... .......... .....
ICMP10843           .......... .......... .......... .......... .....
ICMP10963           .......... .......... .......... .......... .....
ICMP11186           .......... .......... .......... .......... .....
ICMP12948           .......... .......... .......... .......... .....
ICMP2325            .......... .......... .......... .......... .....
ICMP2715            .......... .......... .......... .......... .....
ICMP3173            .......... .......... .......... .......... .....
ICMP6603            .......... .......... .......... .......... .....
ICMP6628            .......... .......... .......... .......... .....
ICMP6803            .......... .......... .......... .......... .....
ICMP6814            .......... .......... .......... .......... .....
ICMP7033            .......... .......... .......... .......... .....
IMI118020           .......... .......... .......... .......... .....
IMI175661           .......... .......... .......... .......... .....
IMI192267           .......... .......... .......... .......... .....
IMI192268           .......... .......... .......... .......... .....
IMI299239           .......... .......... .......... .......... .....
IMI336757           .......... .......... .......... .......... .....
IMI336761           .......... .......... .......... .......... .....
MA1908B             .......... .......... .......... .......... .....
MA3312              .......... .......... .......... .......... .....
SCR97-15B2          .......... .......... .......... .......... .....
SRC02-2A            .......... .......... .......... .......... .....
SRC03-1A8           .......... .......... .......... .......... .....
SRC85-24B           .......... .......... .......... .......... .....
SRC89-25A2          .......... .......... .......... .......... .....
SRC94-134           .......... .......... .......... .......... .....
SRC94-26            .......... .......... .......... .......... .....
SRC94-26A           .......... .......... .......... .......... .....
SRC94-359A          .......... .......... .......... .......... .....
SRC94-44B           .......... .......... .......... .......... .....
SRC95-268B          .......... .......... .......... .......... .....
SRC95-54A1          .......... .......... .......... .......... .....
SRC95-54A2          .......... .......... .......... .......... .....
SRC97-12B           .......... .......... .......... .......... .....
WAC7788             .......... .......... .......... .......... .....
WAC7881             A......... .......... .......... .......... .....
```

FIG. 19A-7

```
tttccgtagg tgaacctgcg gaaggatcat tacctagagt tgcgggctct gcctgccatc tcttacccat gtcttttgag taccttacgt ttcctcggcg ggtccgcccg ccgactggac aaacttaaac cacttgcagt tgaaatcagc gtctgaaaaa acttaatagt tacaactttc aacaacggat ctcttggttc tggcatcgat gaagaacgca gcgaaatgcg ataagtagtg tgaattgcag aattcagtga atcatcgaat ctttgaacgc acattgcgcc ccttggtatt ccatggggca tgcctgttcg agcgtcattt gtaccttcaa gccttgcttg gtgttgggtg tttgtctcgc ctctgcgcgc agactcgcct caaaacaatt ggcagccggc gtattgattt cggagcgcag tacatctcgc gctttgcact caccacggcg gcgtccaaaa gtacattttt acactcttga cctcggatca ggtagggata cccgctgaac ttaa
```

FIG. 19B

FUNGAL ISOLATES AND BIOLOGICAL CONTROL COMPOSITIONS FOR THE CONTROL OF WEEDS

This is a Continuation-in-Part Application of U.S. application Ser. No. 10/478,829 filed Apr. 9, 2004, which is a national phase application of PCT/CA02/00797 filed May 20, 2002, which claims priority to U.S. Application No. 60/294,475 filed on May 30, 2001.

FIELD OF INVENTION

The present invention relates to bioherbicides. More specifically, the present invention relates to fungal bioherbicides, compositions comprising fungal bioherbicides, as well as methods of screening fungal isolates to determine if they exhibit biocontrol activity.

BACKGROUND OF THE INVENTION

The use of pesticides to kill insects, weeds and other disease pests is common in agriculture. It has been estimated that Canadian farmers spend more than $750 million on pesticides, and U.S. and European estimates are likely to be several fold higher. On the Canadian prairies, 95% of the land seeded to wheat, barley, canola and flax is treated with one or more pesticides. However, despite extensive pesticide use, weeds continue to cause an estimated one billion dollars in crop losses in Canada alone every year.

Weeds are detrimental to agricultural crops because they are capable of out competing crop plants for space, sun and nutrients. Particularly troublesome weeds include Canada thistle (*Cirsium arvense*) and other members of the Aster family such as perennial sowthistle (*Sonchus arvense*), and dandelion (*Taraxacum officinale*).

Canada thistle (*Cirsium arvense* [L.] Scop.) is an aggressive perennial weed in field crops, pastures and roadsides, and is particularly prevalent in Western Canada where it occurs in about 50% of all fields. Canada thistle causes crop yield losses of about 15 to 60% in cereal, oilseed and pulse crops, depending on weed density. In cereal crops, densities of 6 to 20 Canada thistle plants per square meter result in an 18 to 30% loss in grain yield. In 1937, Canada thistle was designated as a noxious weed by the Canadian Federal Seeds Act.

Although weeds of the Aster family, for example Canada thistle and dandelion, can reproduce by flowering, they are difficult to eradicate because their extensive root system. The roots are quite brittle and fragment easily during tillage. This results in greater shoot emergence from stimulated buds. Further adding to the difficulties of control, the root fragments carry sufficient food reserves to survive long periods under adverse conditions.

Control of Canada thistle in field crops is currently achieved by pre-seeding, in-crop, and post-harvest chemical control with herbicides, applied at sufficient rates to suppress top growth, or kill the roots. For example, Glyphosate is used as a pre-seeding treatment to kill Canada thistle, or used in-crop on glyphosate tolerant crops. Clopyralid is used for in-crop control to achieve the same effect but has problems with residual activity for some crops in the following year. Other product combinations only provide top growth suppression such as thifensulfuron and tribenuron-methyl or fenoxy-prop and MCPA. Other control options include growing competitive crops and seeding early to get vigorous crop growth before Canada thistle emergence and shallow tilling of soil to reduce root fragmentation and new shoot growth. Also, mowing may be used to control weeds on roadsides, ditches, headlands and fence lines. Controlling patches instead of entire fields is often recommended to reduce costs.

There are a number of drawbacks associated with non-chemical control of Canada thistle in addition to those discussed above. First, there are very few crops which are able to out-compete weeds such as Canada thistle and many crops cannot be seeded early enough to provide the crop with a competitive advantage to Canada thistle. Further, seeding crops earlier than usual may be an inconvenience to farmers. Also, shallow tillage of soil and mowing weeds to kill weeds or prevent weed flowering are only temporary solutions and are at best marginally effective in controlling weeds such as Canada thistle.

There are also several drawbacks associated with the use of chemical herbicides to control weeds such as Canada thistle. Herbicides are expensive and may be too expensive to be used by some farmers. Further, if a farmer uses less than the required dosage of herbicide to kill the weeds, there is an increased risk that some weeds may develop herbicide resistance. There is also an increased risk of herbicide resistance due to overuse of an herbicide. In addition, herbicides are not available for all crops and all situations. For example, there are no effective herbicides available for crops such as peas and lentil whereas some in-crop chemical herbicides only suppress top growth of weeds without controlling root growth, which is a short-term strategy often used for crops such as wheat, barley and canola. Residual herbicidal activity may also limit crop rotation for some crops and some agronomic herbicide practices may increase weed densities. There are also concerns about the short and long term safety of herbicides, both to consumers and the environment.

Environmental issues in the agri-food industry have become a priority with federal and provincial governments, including the development of alternatives for chemical pest control products, with the ultimate goal of reducing chemical pesticide use. Rising economic, environmental and social costs associated with agricultural inputs, spray drift, pesticide residues, government legislation for reduced pesticide use, along with the development of herbicide resistance in weeds make biological control agents attractive strategies for weed control for both agricultural and domestic use.

Broad-leaved weeds in turf situations, such as lawns, parks, and golf courses, disrupt the desired visual uniformity (i.e. are unsightly), create problems in the maintenance of the turf due to clumping and growth habits of the weeds, compete with the turf for light, nutrients, and water. Weeds are also are irritants to humans when allergic reactions to their pollen or the chemicals applied for weed control occur. Important weeds in turfgrass belong to the Compositae (such as dandelion, sowthistle), Caryophyllaceae (such as chickweed), and Rubiaceae, and Convolvulaceae. Typically, control of weeds in turf has been with selective, nonselective, systemic, and contact herbicides applied at various times (pre-plant, pre-emergence, and post-emergence). Public pressure is mounting to prevent the use of chemical herbicides in public places such as parks and homeowner's lawns, for example, By-laws have recently passed in Calgary, Alberta, and Halifax, Nova Scotia, both in Canada, against their use. Chemical herbicides used in these areas leads to increased chemical exposure to susceptible groups in the population like children, pets, and the elderly.

A number of bacteria and fungi are natural pathogens of weeds and it has been suggested that bioherbicides, or weed killers made from biological agents rather than chemical agents, may provide an alternative to chemical pesticides. For example, U.S. Pat. No. 6,008,159 discloses controlling annual weeds using the fungus *Pyrenophora*. U.S. Pat. No's.

5,993,802 and 5,472,690 teach suppressing the growth of *Calmagrostis canadensis* using an isolate of a low temperature basidiomycete fungus, or a mycoherbicide (including at least one or both of *Fusarium nivalis* and *Colletotrichum calamagrostidis*), respectively. U.S. Pat. No's. 5,952,264 and 5,635,444 teach controlling crabgrass using the fungus *Cochliobolus intermedius*, or a fungus selected from the genus *Culvularia*, respectively. U.S. Pat. No. 5,747,029 teaches controlling sicklepod weeds with the fungus *Myrothecium verrucaria*. U.S. Pat. No. 5,698,491 and WO 98/08389 discloses controlling nutsedge weeds with the fungus *Dactylaria higginsii* (WO 98/08389 and U.S. Pat. No. 5,698,491). U.S. Pat. No. 4,606,751 teaches controlling Johnson grass and similar weeds with *Bipolaris sorghicola* spores. The spores are suspended in a solution of water and surfactant and sprayed onto a field onto which the weed is growing. U.S. Pat. No. 5,795,845 discloses a bioherbicidal composition comprising an invert emulsion carrier and a microorganism which is a weakly or non-pathogenic bacterium or fungus. The composition may be used to control pigweed, plumeless thistle, velvet leaf and ground cherry. U.S. Pat. No. 4,636,386 discloses an isolate of *Alternaria* for the control of Italian thistle. U.S. Pat. No. 5,994,27 discloses a composition comprising a bioherbicide which is an isolate of *Sclerotinia minor* which produces foliar wilt and rot in broadleaf weed species so as to inhibit their growth. The bioherbicide may be used to control the growth of broadleaf weeds such as dandelion, broadleaf plantain, ragweed, ivy, knotweed sow thistle and white clover.

Brebaum and Boland (1999, Plant Disease 83:2000) disclose *Phoma exigua* and *Phoma herbarum* as pathogens of dandelion (*Taraxacum officinale*), however, no weed controlling activity was reported using these species.

None of the identified references disclose fungal isolates derived from *Phoma macrostoma* as biocontrol compositions suitable for use to control Canada thistle, dandelion, or other weed species.

There is a need in the art for novel bioherbicides and biocontrol compositions for controlling weeds. Further there is a need in the art for novel bioherbicides and biocontrol compositions for controlling weed plants for example Canada thistle, perennial sowthistle, dandelion, prairie sunflower, field bindweed, wild buckwheat, and scentless chamomile, cleavers, and chickweed. Further, there is a need in the art for biocontrol compositions comprising a biological control agent and a growth medium for supporting the viability of the biological control agent when the biocontrol composition is employed to control weeds. Further there is a need in the art for methods of detecting fungal isolates that may be used as a suitable biocontrol agent.

SUMMARY OF THE INVENTION

The present invention relates to bioherbicides. More specifically, the present invention relates to fungal bioherbicides and compositions comprising fungal bioherbicides as well as methods for screening fungal isolates to determine if they exhibit biocontrol activity.

It is an object of the invention to provide improved fungal isolates and biological control compositions for the control of weeds According to the present invention there is provided a method (A) of controlling one or more broad leaf weeds comprising administering one or more than one isolate of *Phoma macrostoma*, an extract therefrom, an inoculated broth therefrom, or a combination thereof, to the one or more broad leaf weeds, or to soil where said weeds grow, the one or more than one *Phoma* cf *macrostoma* isolate, an extract therefrom, or an inoculated broth therefrom, exhibiting weed control activity.

The present invention is also directed to the method defined above wherein the *Phoma macrostoma* isolate originates from Canada thistle (*Cirsium arvense*).

The present invention is also directed to the method (A) defined above wherein the one or more broad leaf weeds is a species of a family selected from the group consisting of Compositae, Caryophyllaceae, Convolvulaceae, Plantaginaceae and Rubiaceae. Preferably, the one or more broad leaf weeds is selected from the group consisting of Canada thistle, perennial sowthistle, dandelion, scentless chamomile, false cleavers, chickweed, wild buckwheat, plantain, prairie sunflower and field bindweed.

The present invention also provides a biocontrol agent comprising one or more than one *Phoma macrostoma* isolate, an extract therefrom, an inoculated broth therefrom, or a combination thereof, said one or more than one *Phoma macrostoma* isolate, or an extract therefrom, or an inoculated broth therefrom, exhibiting weed control activity, growth enhancement activity, or both. The one or more than one *Phoma macrostoma* isolate is selected from the group consisting of:

a) 85-24B (IDAC 230201-1, deposited Feb. 23, 2001),
b) 89-25A (IDAC 110401-1, deposited Apr. 11, 2001),
c) 94-26 (IDAC 230201-2, deposited Feb. 23, 2001),
d) 94-44B (IDAC 230201-3, deposited Feb. 23, 2001)
e) 94-134 (IDAC 230201-4, deposited Feb. 23, 2001),
f) 94-359A (IDAC 110401-2, deposited Apr. 11, 2001),
g) 95-54A1 (IDAC 230201-5, deposited Feb. 23, 2001),
h) 95-268B (IDAC 110401-3, deposited Apr. 11, 2001),
i) 97-12B (IDAC 230201-6, deposited Feb. 23, 2001),
j) 97-15B2 (IDAC 110401-4, deposited Apr. 11, 2001), and a combination thereof. The *Phoma* cf. *macrostoma* isolates are deposited at the International Depositary Authority of Canada (IDAC), Bureau of Microbiology, Health Canada, 1015 Arlington Street, Winnipeg, Manitoba, R3E 3R2 Canada.

The present invention further provides a biocontrol composition comprising the biocontrol agent of the present invention and a medium for supporting viability of the one or more than one *Phoma macrostoma* isolate. The medium is preferably selected from the group consisting of Agar, pesta, peat prill, vermiculite, clay, starches, potato dextrose broth, vegetable juice broth, cereal grain and legume grain.

This invention pertains to the above method (A) wherein the extract is selected from the group consisting of heat killed barley inoculum, a chloroform extract of the *Phoma macrostoma* isolate, a methanol extract of the *Phoma macrostoma* isolate, and a ethyl-acetate extract of the *Phoma macrostoma* isolate, and the inoculated broth is selected from the group consisting of a crude inoculated broth, a filtered inoculated broth, or a centrifuged inoculated broth.

The present invention also pertains to a method (B) of controlling weed development during crop growth comprising:

a) adding an effective amount of a biocontrol agent comprising one or more than one *Phoma* cf *macrostoma* isolate, an extract therefrom, an inoculated broth therefrom, or combination thereof to soil to produce treated soil, the one or more than one *Phoma* cf *macrostoma* isolate, an extract therefrom, or an inoculated broth therefrom, exhibiting weed control activity;

b) planting the crops in the treated soil; and c) growing the crop.

According to the present invention there is also provided a method (C) of controlling weed development during crop growth comprising:

a) planting the crop, b) adding an effective amount of a biocontrol agent comprising one or more than one *Phoma* cf *macrostoma* isolate, an extract therefrom, an inoculated broth therefrom, or a combination therefrom, to soil where the crop is planted, the one or more than one *Phoma* cf *macrostoma* isolate, extract therefrom, or inoculated broth therefrom, exhibiting weed control activity;

c) growing the crop.

The present invention is also directed to a method (D) of controlling weed development during crop growth comprising:

a) adding an effective amount of a biocontrol agent comprising one or more than one *Phoma* cf *macrostoma* isolate, an extract therefrom, an inoculated broth therefrom, or a combination thereof, to a crop seed to produce treated crop seed, the one or more than one *Phoma* cf *macrostoma* isolate, extract therefrom, or inoculated broth therefrom, exhibiting weed control activity;

b) planting the treated crop seed; and c) growing the crop.

Also included in this invention is the method (either B, C or D) as just defined wherein the treated crop seed is grass seed, including domestic and specialty turf grass seed, animal pasture or hay seed mixes comprising one or more of timothy, fescue, blue grass, perennial rye grass, bromegrass, canary grass, red top and orchard grass seed.

The present invention also provides a method (E) of controlling weed development during established crop growth comprising:

a) adding an effective amount of a biocontrol agent comprising one or more than one *Phoma* cf *macrostoma* isolate, an extract therefrom, an inoculated broth therefrom, or a combination thereof, to the established crop, the one or more than one *Phoma* cf *macrostoma* isolate, an extract therefrom, or an inoculated broth therefrom, exhibiting weed control activity, and (b growing the crop.

Also included in this invention is the method (E) as just defined wherein the established crop is grass, including domestic and specialty turf grasses, animal pasture or hay mixes comprising one or more of timothy, fescue, blue grass, perennial rye grass, bromegrass, canarygrass, red top and orchard grass.

The present invention also provides a method (F) of controlling weed development comprising applying an effective amount of a biocontrol agent comprising one or more than one *Phoma* cf *macrostoma* isolate, an extract therefrom, an inoculated broth therefrom, or a combination thereof, to the soil where the weed grows, the one or more than one *Phoma* cf *macrostoma* isolate, an extract therefrom, or an inoculated broth therefrom, exhibiting weed control activity. The biocontrol agent is preferably an extract from said one or more than one *Phoma macrostoma* isolate.

The present invention further provides a method (G) of controlling weed development comprising applying an effective amount of a biocontrol agent comprising one or more than one *Phoma* cf *macrostoma* isolate, an extract therefrom, an inoculated broth therefrom, or a combination thereof, to said weed, the one or more than one *Phoma* cf *macrostoma* isolate, an extract therefrom, or an inoculated broth therefrom, exhibiting weed control activity.

The present invention also provides a method (H) of controlling weed development during growth of a lawn of grass, the method comprising:

a) adding an effective amount of a biocontrol agent comprising one or more than one *Phoma* cf *macrostoma* isolate, an extract therefrom, an inoculated broth therefrom, or combination thereof to soil to produce treated soil, the one or more than one *Phoma* cf *macrostoma* isolate, an extract therefrom, or an inoculated broth therefrom, exhibiting weed control activity, b) planting grass seed in said treated soil, and c) growing said lawn from said grass seed.

The present invention also provides a method (I) of controlling weed development during growth of a lawn of grass, the method comprising:

a) planting grass seed, b) adding an effective amount of a biocontrol agent comprising one or more than one *Phoma* cf *macrostoma* isolate, an extract therefrom, an inoculated broth therefrom, or a combination therefrom, to soil where the grass is planted, the one or more than one *Phoma* cf *macrostoma* isolate, extract therefrom, or inoculated broth therefrom, exhibiting weed control activity; and c) growing said lawn from said grass seed.

The present invention also provides a method (J) of controlling weed development during growth of a lawn of grass comprising:

a) adding an effective amount of a biocontrol agent comprising one or more than one *Phoma* cf *macrostoma* isolate, an extract therefrom, an inoculated broth therefrom, or a combination thereof, to grass seed to produce treated grass seed, the one or more than one *Phoma* cf *macrostoma* isolate, extract therefrom, or inoculated broth therefrom, exhibiting weed control activity;

b) planting said treated grass seed; and c) growing said lawn from said treated grass seed.

The present invention also provides a method (K) of controlling weed development during growth of an established lawn of grass, the method comprising:

a) adding an effective amount of a biocontrol agent comprising one or more than one *Phoma* cf *macrostoma* isolate, an extract therefrom, an inoculated broth therefrom, or a combination thereof to the established lawn, the one or more than one *Phoma* cf *macrostoma* isolate, extract therefrom, or inoculated broth therefrom, exhibiting weed control activity; and b) growing the lawn.

The present invention also provides a method (L) of enhancing the growth of a crop, the method comprising:

a) adding an effective amount of a biocontrol agent comprising one or more than one *Phoma* cf *macrostoma* isolate, an extract therefrom, an inoculated broth therefrom, or a combination thereof to soil to produce a treated soil, the one or more than one *Phoma* cf *macrostoma* isolate, an extract therefrom, or an inoculated broth therefrom, exhibiting weed control activity;

b) planting the crop in said treated soil, and c) growing said crop.

The present invention also provides a method (M) of enhancing the growth of a crop, the method comprising:

a) planting said crop in soil;

b) adding an effective amount of a biocontrol agent comprising one or more than one *Phoma* cf *macrostoma* isolate, an extract therefrom, an inoculated broth therefrom, or a combination thereof to the soil where said crop is planted, the one or more than one *Phoma* cf *macrostoma* isolate, an extract therefrom, or an inoculated broth therefrom, exhibiting weed control activity; and c) growing said crop.

The present invention further provides a method (N) of enhancing the growth of an established crop, the method comprising:

a) adding an effective amount of a biocontrol agent comprising one or more than one *Phoma* cf *macrostoma* isolate, an extract therefrom, an inoculated broth therefrom, or a combination thereof to the established crop, the one or more than one *Phoma* cf *macrostoma* isolate, an extract therefrom, or an inoculated broth therefrom, exhibiting weed control activity; and b) growing the crop.

Also included in this invention is the methods (either L, M or N) as just defined wherein the crop is grass, including domestic and specialty turf grasses, animal pasture or hay mixes comprising one or more of timothy, fescue, blue grass, perennial rye grass, bromegrass, canarygrass, red top and orchard grass.

The present invention is also directed to a method (O) of enhancing the growth of a crop, the method comprising:

a) adding an effective amount of a biocontrol agent comprising one or more than one *Phoma* cf *macrostoma* isolate, an extract therefrom, an inoculated broth therefrom, or a combination thereof, to a crop seed to produce treated crop seed, the one or more than one *Phoma* cf *macrostoma* isolate, an extract therefrom, or an inoculated broth therefrom, exhibiting weed control activity;

b) planting the treated crop seed; and c) growing the crop.

Also included in this invention is the method (O) as just defined wherein the treated crop seed is grass seed, including domestic and specialty turf grass seed, animal pasture or hay seed mixes comprising one or more of timothy, fescue, blue grass, perennial rye grass, bromegrass, canary grass, red top and orchard grass seed.

The methods of the present invention also relate to the use of a biocontrol composition comprising one or more than one *Phoma* cf *macrostoma* isolate, an extract therefrom, an inoculated broth therefrom, or a combination thereof, the one or more than one *Phoma* cf *macrostoma* isolate, an extract therefrom, or an inoculated broth therefrom, exhibiting weed control activity; and a medium for supporting viability of the one or more than one *Phoma* cf *macrostoma* isolate.

The methods of the present invention are preferably used to control weed development during growth of a perennial crop. Preferably, the perennial crop is selected from the group consisting of a turf, a perennial grass, and a winter cereal.

The present invention also provides for any of the above methods wherein the biocontrol agent or composition is applied to the soil before or after emergence of the weed, preferably before emergence.

The present invention also provides for any of the above methods wherein the biocontrol agent or composition is applied by dusting, rubbing, spreading, drilling, banding, broadcasting, spraying, liquid injection, pouring or soil drenching.

The present invention also provides for any of the above methods wherein the one or more than one *Phoma macrostoma* isolate originates from Canada thistle.

The present invention also provides for any of the above methods wherein the one or more than one *Phoma macrostoma* isolate is selected from the group consisting of:

a) 85-24B (IDAC 230201-1, deposited Feb. 23, 2001),
b) 89-25A (IDAC 110401-1, deposited Apr. 11, 2001),
c) 94-26 (IDAC 230201-2, deposited Feb. 23, 2001),
d) 94-44B (IDAC 230201-3, deposited Feb. 23, 2001)
e) 94-134 (IDAC 230201-4, deposited Feb. 23, 2001),
f) 94-359A (IDAC 110401-2, deposited Apr. 11, 2001),
g) 95-54A1 (IDAC 230201-5, deposited Feb. 23, 2001),
h) 95-268B (IDAC 110401-3, deposited Apr. 11, 2001),
i) 97-12B (IDAC 230201-6, deposited Feb. 23, 2001),
j) 97-15B2 (IDAC 110401-4, deposited Apr. 11, 2001), and a combination thereof. The *Phoma* cf. *macrostoma* isolates are deposited at the International Depositary Authority of Canada (IDAC), Bureau of Microbiology, Health Canada, 1015 Arlington Street, Winnipeg, Manitoba, R3E 3R2 Canada.

The present invention embraces a coated crop seed comprising one or more *Phoma macrostoma* isolates and a binder. The invention also includes a coated crop seed comprising an extract obtained from one or more *Phoma macrostoma* isolates and a binder. The one or more *Phoma macrostoma* isolate is preferably selected from the group consisting of:

a) 85-24B (IDAC 230201-1, deposited Feb. 23, 2001),
b) 89-25A (IDAC 110401-1, deposited Apr. 11, 2001),
c) 94-26 (IDAC 230201-2, deposited Feb. 23, 2001),
d) 94-44B (IDAC 230201-3, deposited Feb. 23, 2001)
e) 94-134 (IDAC 230201-4, deposited Feb. 23, 2001),
f) 94-359A (IDAC 110401-2, deposited Apr. 11, 2001),
g) 95-54A1 (IDAC 230201-5, deposited Feb. 23, 2001),
h) 95-268B (IDAC 110401-3, deposited Apr. 11, 2001),
i) 97-12B (IDAC 230201-6, deposited Feb. 23, 2001),
j) 97-15B2 (IDAC 110401-4, deposited Apr. 11, 2001), and a combination thereof. The *Phoma* cf. *macrostoma* isolates are deposited at the International Depositary Authority of Canada (IDAC), Bureau of Microbiology, Health Canada, 1015 Arlington Street, Winnipeg, Manitoba, R3E 3R2 Canada.

The present invention also provides that the coated crop seed is grass seed, including domestic and specialty turf grass seed, animal pasture or hay seed mixes comprising one or more of timothy, fescue, blue grass, perennial rye grass, bromegrass, canary grass, red top and orchard grass seed.

The present invention also provides a probe for detecting one or more than one isolate of *Phoma macrostoma* that exhibits weed control activity, the probe comprising SEQ. ID. NO: 1.

The present invention also provides a method (P) of detecting one or more than one isolate of *Phoma macrostoma* that exhibits weed control activity using the probe of the present invention. The method preferably comprises mixing nucleic acid from the one or more than one *Phoma macrostoma* isolate with the probe of the present invention under hybridization conditions, wherein hybridization of the nucleic acid from the one or more than one isolate to the probe indicates that the isolate exhibits weed control activity. The nucleic acid of the *Phoma macrostoma* isolate is preferably genomic DNA.

The present invention also provides a primer pair for detecting one or more than one isolate of *Phoma macrostoma* that exhibits weed control activity, said primer pair comprising SEQ. ID. NO: 2 and SEQ. ID. NO: 3.

The present invention further provides a method (Q) of detecting one or more than one isolate of *Phoma macrostoma* that exhibits weed control activity using the primer pair of the present invention. The method preferably comprises amplifying nucleic acid from the one or more than one *Phoma macrostoma* isolate with the primer pair of the present invention, wherein the presence of an amplified nucleic acid fragment indicates that the isolate exhibits weed control activity. The nucleic acid of the *Phoma macrostoma* isolate is preferably genomic DNA.

This invention pertains to the above method (Q) wherein genomic DNA from the one or more than one *Phoma macrostoma* isolate is amplified using Polymerase Chain Reaction (PCR) and the resulting PCR product(s) is separated by electrophoresis, wherein the presence of an amplified DNA fragment of between 0.8 and 1.2 kb indicates that the isolate exhibits weed control activity.

The present invention also provides a method (R) of screening one or more than one isolate of *Phoma macrostoma* using random amplified polymorphic DNA (RAPD) fingerprinting to determine if the one or more than one isolate exhibits weed control activity, the method comprising:

a) amplifying chromosomal DNA from the one or more than one *Phoma macrostoma* isolate known to exhibit weed control activity using a primer selected from the group consisting of SEQ. ID. NO: 4; SEQ. ID NO: 5; SEQ. ID. NO: 6; SEQ. ID. NO: 7; and a combination thereof, to obtain a RAPD fragment pattern of the isolate;

b) amplifying chromosomal DNA from the one or more than one *Phoma macrostoma* isolate being screened, under the same, or substantially the same conditions as (a), to obtain a RAPD fragment pattern of the isolate;

c) comparing the RAPD fragment pattern obtained in step (a) to the RAPD fragment pattern obtained in step (b), wherein similarities between the RAPD fragment patterns indicate that the one or more than one isolate of *Phoma macrostoma* being screened exhibits weed control activity.

The present invention also provides a method (S) of screening one or more than one isolate of *Phoma macrostoma* using amplified fragment length polymorphisms (AFLP) to determine if the one or more than one isolate exhibits weed control activity, the method comprising:

a) digesting chromosomal DNA from one or more than one *Phoma macrostoma* isolate known to exhibit weed control activity using restriction enzymes EcoRI and MseI, to obtain a plurality of DNA fragments;

b) ligating double stranded oligonucleotide EcoRI and MseI adaptors to the EcoRI and MseI restriction sites of the DNA fragments obtained in step (a);

c) amplifying the ligated DNA fragments obtained in step (b) with a primer pair selected from the group consisting of:
(i) SEQ. ID. NO: 10 and SEQ. ID. NO: 11;
(ii) SEQ. ID. NO: 10 and SEQ. ID. NO: 12;
(iii) SEQ. ID. NO: 13 and SEQ. ID. NO: 11;
(iv) SEQ. ID. NO: 13 and SEQ. ID. NO: 12;
(v) SEQ. ID. NO: 14 and SEQ. ID. NO: 11;
(vi) SEQ. ID. NO: 14 and SEQ. ID. NO: 12; and
a combination thereof; to obtain a set of amplified DNA fragments of the isolate;

d) repeating steps (a) to (c) for chromosomal DNA from the one or more than one *Phoma macrostoma* isolate being screened, to obtain a set of amplified DNA fragments of the isolate;

e) comparing the set of amplified DNA fragments obtained from the one or more than one *Phoma macrostoma* isolate known to exhibit weed control activity to the set of amplified DNA fragments obtained from the one or more than one *Phoma macrostoma* isolate being screened, wherein similarities between the amplified DNA fragments indicate that the one or more than one isolate of *Phoma macrostoma* being screened exhibits weed control activity.

This invention pertains to the above methods (P, Q, R or S) of screening wherein the one or more than one isolate of *Phoma macrostoma* known to exhibit weed control activity in step (a) is selected from the group consisting of:
a) 85-24B (IDAC 230201-1, deposited Feb. 23, 2001),
b) 89-25A (IDAC 110401-1, deposited Apr. 11, 2001),
c) 94-26 (IDAC 230201-2, deposited Feb. 23, 2001),
d) 94-44B (IDAC 230201-3, deposited Feb. 23, 2001)
e) 94-134 (IDAC 230201-4, deposited Feb. 23, 2001),
f) 94-359A (IDAC 110401-2, deposited Apr. 11, 2001),
g) 95-54A1 (IDAC 230201-5, deposited Feb. 23, 2001),
h) 95-268B (IDAC 110401-3, deposited Apr. 11, 2001),
i) 97-12B (IDAC 230201-6, deposited Feb. 23, 2001),
j) 97-15B2 (IDAC 110401-4, deposited Apr. 11, 2001);

or a combination thereof. The *Phoma* cf. *macrostoma* isolates are deposited at the International Depositary Authority of Canada (IDAC), Bureau of Microbiology, Health Canada, 1015 Arlington Street, Winnipeg, Manitoba, R3E 3R2 Canada.

The present invention provides a *phoma macrostoma* isolate characterized as having an amplified fragment length polymorphism (AFLP) as disclosed in FIG. 21, lanes 22, 44-46, and 48-53 using primer pairs:
(i) SEQ. ID. NO: 10 and SEQ. ID. NO: 11;
(ii) SEQ. ID. NO: 10 and SEQ. ID. NO: 12;
(iii) SEQ. ID. NO: 13 and SEQ. ID. NO: 11;
(iv) SEQ. ID. NO: 13 and SEQ. ID. NO: 12;
(v) SEQ. ID. NO: 14 and SEQ. ID. NO: 11;
(vi) SEQ. ID. NO: 14 and SEQ. ID. NO: 12; and
a combination thereof;

This summary of the invention does not necessarily describe all features of the invention.

BRIEF DESCRIPTION OF THE DRAWINGS

These and other features of the invention will become more apparent from the following description in which reference is made to the appended drawings wherein.

FIG. 9 shows the DNA sequence data for the generated probe; SEQ. ID. NO:1.

FIG. 10 shows the base sequence positions of Left primer; SEQ. ID. NO: 2 (>>>) and Right primer; SEQ. ID. NO: 3 (<<<) designed for the probe (SEQ. ID. NO: 1).

Figure 11:
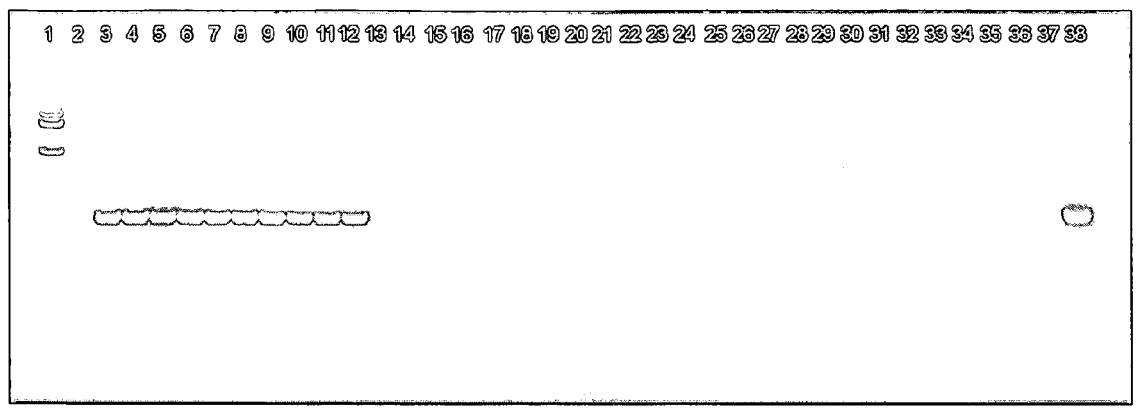

FIG. 11 shows the specificity of PCR primer pair (SEQ. ID. NO: 2; SEQ. ID. NO: 3) to *P. macrostoma*. Lane 1: GeneRuler™ 1 kb Ladder, Lane 2: water control, Lane 3-12: *Phoma macrostoma* biocontrol isolates 85-24B, 89-25A2, 94-26, 94-44B, 94-134, 94-359A, 95-54A1, 95-268B, 97-12B, and 97-15B2, Lane 13: *P. dennisii* var. *dennisii* CBS135.96, Lanes 14-17: *P. macrostoma* var. *macrostoma* isolates CBS154.83, CBS482.95, CBS488.94, and CBS837.84, Lane 18: *P. macrostoma* var. *incolorata* CBS389.84, Lanes 19-21: *P. lingam* Leroy, Peace-3, and P186-12, Lanes 22-24: *P. herbarum* AI, AIV, and G5/2, Lanes 25-26: *P. chrysanthemicola* 90-64 and 91-271, Lanes 27-30: *P. exigua* 92-180-1, *P. medicaginis* 94-335A1, *P. nebulosa* 92-74, and *P. pomorum* 91-177, Lanes 31-37: *Cochliobolus sativus* 2715, *Epicoccum purpurascens* 98-SD85-18, *Fusarium oxysporum* 91-121B, *Penicillium* sp. 02-10, *Pythium* sp. 94-123-B1, *Sclerotinia sclerotiorum* SS-321, and *Septoria cirsii* 98-11B2, Lane 38: pBluescript KSII 1-6 (+ve control).

Figure 12:
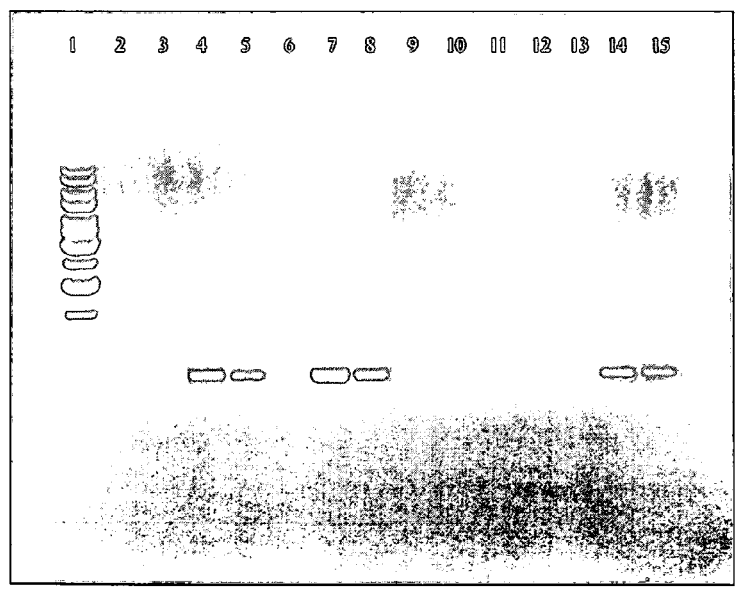

FIG. 12 shows the sensitivity of PCR primer pair (SEQ. ID. NO: 2; SEQ. ID. NO: 3) to *P. macrostoma* 94-44B in soil and plant tissues under greenhouse conditions. The inoculum was applied at various doses to pots containing field soil. Lane1: GeneRuler™ 1 kb Ladder, Lane 2-8: DNA extracted from soil in pots applied with 0, 4, 8, 16, 31, 64, and 125 g of inoculum/m², respectively, Lanes 9-15: DNA extracted from plant roots in pots applied with 0, 4, 8, 16, 31, 64, and 125 g of inoculum/m², respectively.

FIG. 13 shows PCR detection of biocontrol strains of *Phoma macrostoma* using strain-specific primers SEQ. ID. NO: 2 and SEQ. ID. NO: 3. Isolates that amplified are given in bold type. FIG. 13A shows lane 1, Low Mass Ladder (Invitrogen); lane 2, empty; lane 3-29, SRC95-54A2, SRC97-15B2*, SRC94-359A, SRC94-134, SRC85-24B*, SRC95-268B, SRC95-54A1*, SRC89-25A2, SRC97-12B, SRC02-2A, SRC94-26, SRC94-26Avir, SRC94-44B, CBS154.83, CBS837.84, CBS488.94, CBS839.84, CBS482.95, CBS483.66, CBS560.70, CBS598.94, DAOM175135, DAOM175940†, DAOM175951, ICMP2325, ICMP2715, ICMP3173. *These three SRC isolates failed to amplify, but were expected to be positive. Hence, all three isolates were re-analysed as indicated in FIG. 13C. †Isolate DAOM175940 was the only other isolate to yield a positive response. FIG. 13B shows lane 30, Low Mass Ladder; lane 31-54, ICMP6603, ICMP6628, ICMP6803, ICMP6814, ICMP7033, ICMP10843, ICMP10963, ICMP11186, ICMP12948, IMI118020, IMI175661*, IMI299239, IMI336757, IMI336761, WAC7881, CCM-F322, CCM-F323, ATCC24524, ATCC46580, CBS112.36, CBS115.12, CBS185.25, CBS198.69, CBS297.36. *This isolate returned a faintly positive response for unknown reason, although it was expected to be yield a negative response. This isolate and one isolate on either side were re-analysed as indicated in FIG. 13C. FIG. 13C shows lane 1, Low Mass Ladder; lane 2-26, SRC95-54A2, SRC97-15B2*, SRC94-359A, SRC94-134, SRC85-24B, SRC95-268B, SRC95-54A1, SRC89-25A2, SRC97-12B, SRC02-2A, SRC94-26, SRC94-26A, SRC94-44B, SRC85-24B, SRC95-54A1, SRC94-26, SRC94-44B, SRC94-26Avir, DAOM175940, IMI118020, IMI175661, IMI299239, SRC85-24B, SRC95-54A1, lane 26, blank. *Isolates SRC97-15B2 still failed to amplify despite being expected to yield a positive response. Morphological examination suggested the culture was contaminated so SRC97-15B2 was resuscitated from stock cultures and DNA extracted for re-analysis as indicated in FIG. 13D. Other SRC isolates that failed previously returned positive responses following an adjustment in DNA concentration. FIG. 13D shows lane 1, Low Mass Ladder; Lanes 2-23, MA1908B, PFC2705, CBS300.36, olrim779, PFC3313, olrim776, WAC7788, CBS297.36, CBS371.61, CBS529.66A, SRC97-15B2*, CBS529.66B, MA3312, MA1908R, CBS223.69, IMI192267, PD68/1014A, DAOM179750, CBS109173, SRC03-1A8, IMI192268, PD68/1014B, CBS345.97; Lanes 25-30, Controls, +ve SRC94-44B, –ve ATCC24524, +ve SRC95-54A2, –ve ATCC46580, +ve SRC02-2A, –ve CBS1 12.36. *Positive responses were reported for SRC97-15B2 following re-cultivation and re-extraction. Other isolates not previously tested were included: *P. macrostoma* type cultures SRC03-1A8, CBS223.69 and CBS529.66 (Table 5), and several other isolates that were not part of the *P. macrostoma* collection presented in Table 5.

Figure 14:
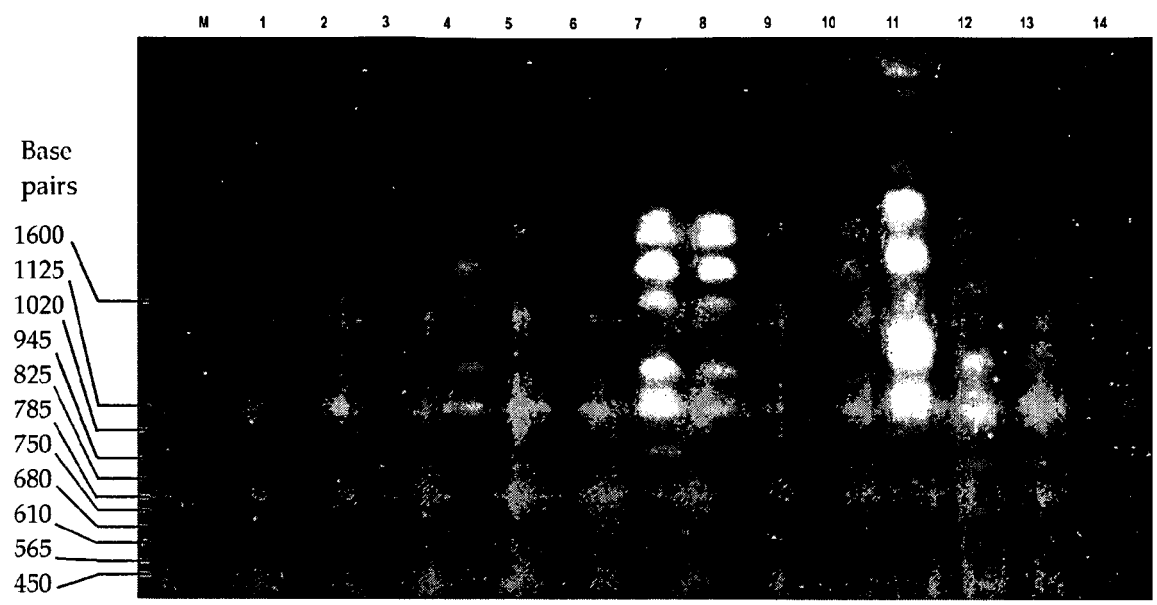

FIG. 14 shows electrokaryotypes of *P. macrostoma* and several other *Phoma* isolates separated by pulsed field gel electrophoresis. Lane M: *Saccaromyces cerevisiae* marker; Lanes 1-10: *P. macrostoma* isolates 85-24B, 89-25A2, 94-26, 94-44B, 94-134, 94-359A, 95-54A1, 95-268B, 97-12B, and 97-15B2, respectively; Lane 11: *P. medicaginis* 94-335 A1; Lanes 12-14: *P. herbarum* isolates AI, AIV and G5/5/2, respectively.

Figure 15:
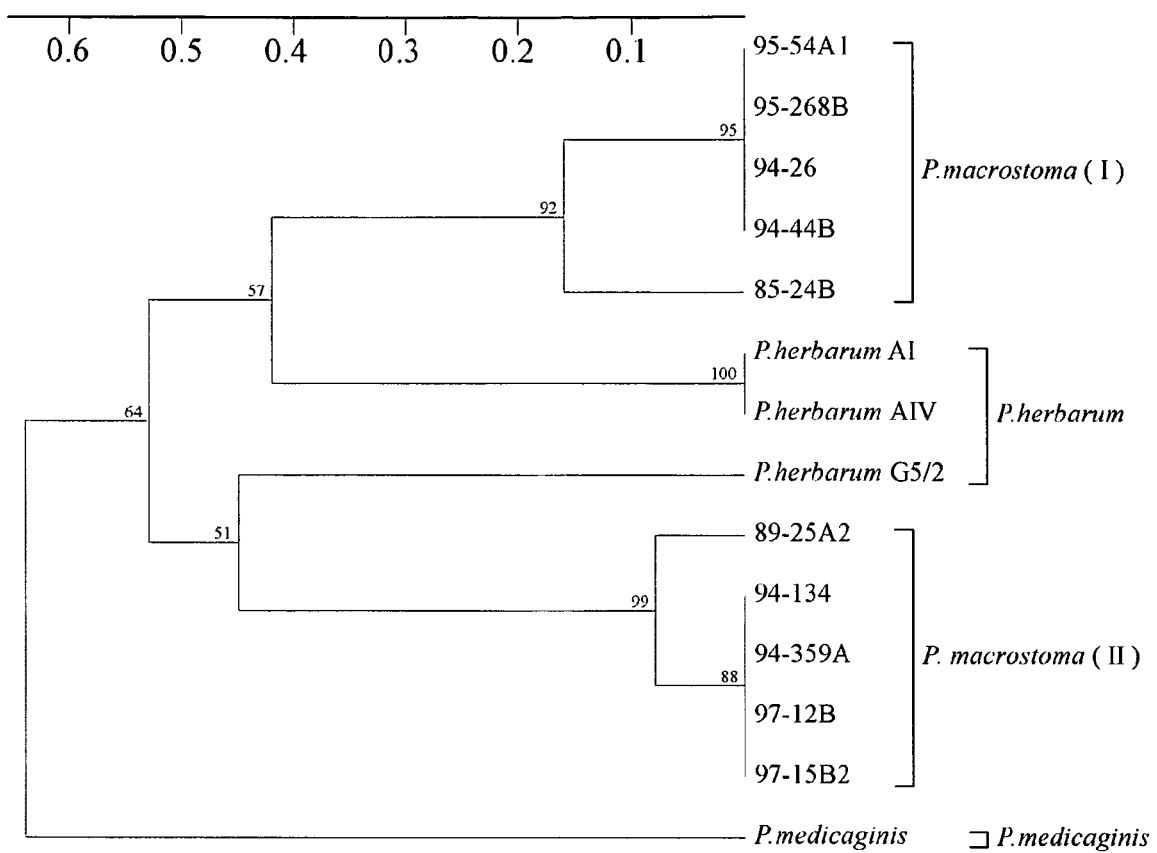
Figure 16A:
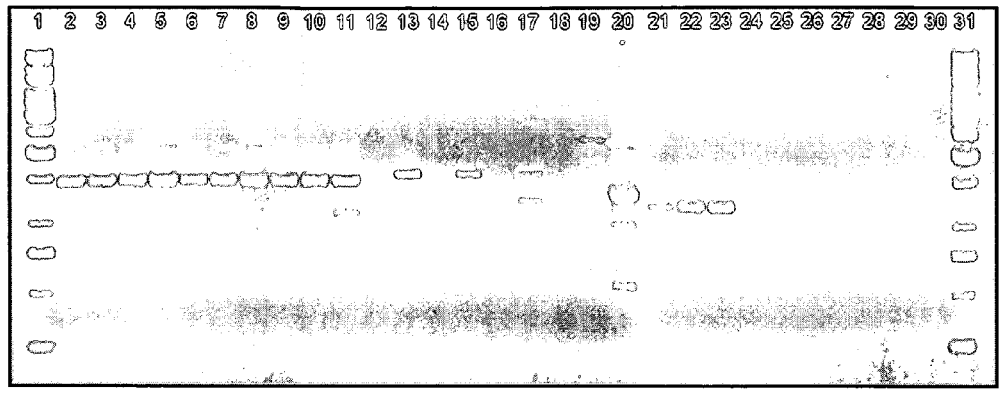
Figure 16B:
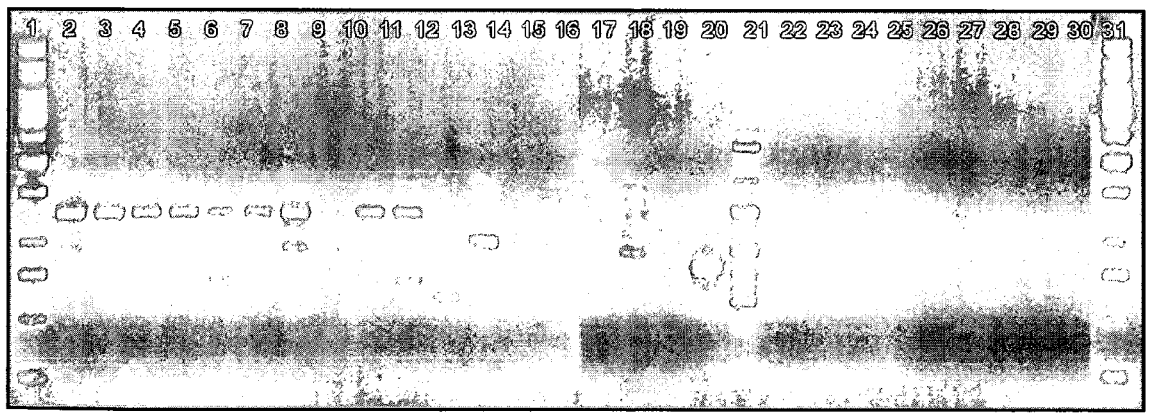
Figure 16C:
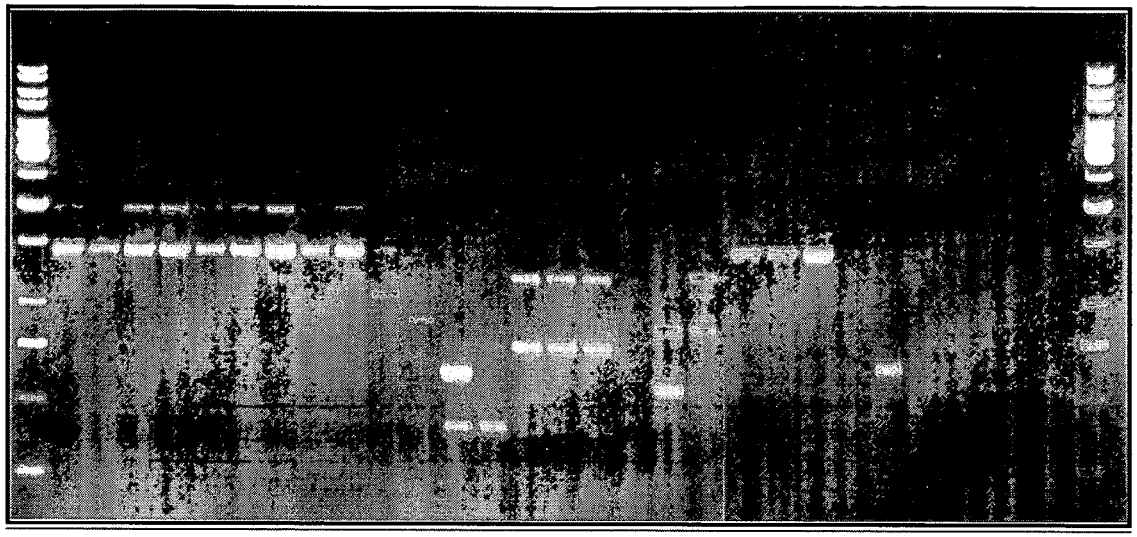
Figure 16D:
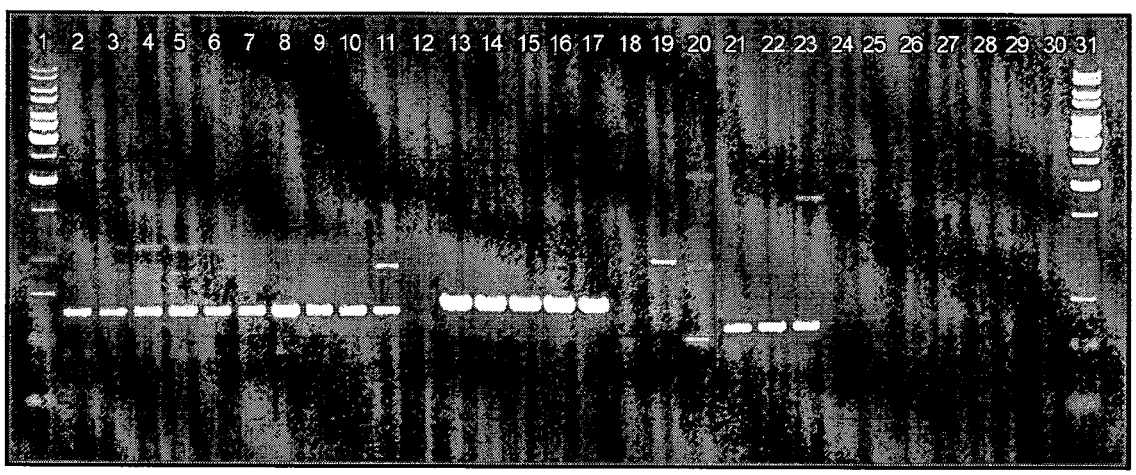

FIG. 15 shows the phylogenetic relationship among several *Phoma* isolates revealed by CHEF profiles. Two distinct subgroups were evident, within which limited variation was found. Biocontrol isolates 94-44B, 85-24B, 94-26, 95-268B and 95-54A1 were clustered in subgroup I (Type I profile), while isolates 89-25A2, 94-134, 94-359A, 97-12B, and 97-15B2 in subgroup II (Type II profile). The evolutionary distance scale (placed on the top of the figure) and bootstrap values (presented on nodes of the tree) were calculated using Treecon® for Windows software. All main clusters were strongly supported by bootstrap replications.

FIG. 16 shows Random Amplified Polymorphic DNA (RAPD) analyses of genetic variations among *Phoma* isolates. FIG. 16A shows RAPD analyses of genetic variations among *Phoma* isolates with oligonucleotide primer UBC 308. Lanes 1 and 31, GeneRuler™ 1 kb DNA Ladder (MBI Fermentas); Lanes 2-11, *Phoma macrostoma* isolates 85-24B, 89-25A2, 94-26, 94-44B, 94-134, 94-359A, 95-54A1, 95-268B, 97-12B, and 97-15B2; Lane 12, *P. dennisii* var. *dennisii* CBS135.96; Lanes 13-16, *P. macrostoma* var. *macrostoma* isolates CBS154.83, CBS482.95, CBS488.94 and CBS837.84; Lane 17, *P. macrostoma* var. *incolorata* CBS839.84; Lanes 18-20, *P. lingam* isolates Leroy, Peace-3 and P186-12; Lanes 21-23, *P. herbarum* isolates AI, AIV and G/5/2; Lanes 24-25, *P. chrysanthemicola* 90-64 and 91-27I; Lanes 26-29, *P. exigua* 92-180-1, *P. medicaginis* 94-335A1, *P. nebulosa* 92-74, and *P. pomorum* 91-177; Lane 30, Blank. FIG. 16B shows RAPD analyses of genetic variation among *Phoma* isolates with oligonucleotide primer UBC 356. Lanes 1 and 31, GeneRuler™ 1 kb DNA Ladder (MBI Fermentas); Lanes 2-11, *Phoma macrostoma* isolates 85-24B, 89-25A2, 94-26, 94-44B, 94-134, 94-359A, 95-54A1, 95-268B, 97-12B, and 97-15B2; Lane 12, *P. den-* nisii var. dennisii CBS135.96; Lanes 13-16, *P. macrostoma* var. *macrostoma* isolates CBS154.83, CBS482.95, CBS488.94 and CBS837.84; Lane 17, *P. macrostoma* var. *incolorata* CBS839.84; Lanes 18-20, *P. lingam* isolates Leroy, Peace-3 and P186-12; Lanes 21-23, *P. herbarum* isolates AI, AIV and G/5/2; Lanes 24-25, *P. chrysanthemicola* 90-64 and 91-27I; Lanes 26-29, *P. exigua* 92-180-1, *P. medicaginis* 94-335A1, *P. nebulosa* 92-74, and *P. pomorum* 91-177; Lane 30, Blank. FIG. 16C shows RAPD analyses of genetic variation among *Phoma* isolates with oligonucleotide primer UBC 734. Lanes 1 and 31, GeneRuler™ 1 kb DNA Ladder (MBI Fermentas); Lanes 2-11, *Phoma macrostoma* isolates 85-24B, 89-25A2, 94-26, 94-44B, 94-134, 94-359A, 95-54A1, 95-268B, 97-12B, and 97-15B2; Lane 12, *P. dennisii* var. *dennisii* CBS135.96; Lanes 13-16, *P. macrostoma* var. *macrostoma* isolates CBS154.83, CBS482.95, CBS488.94 and CBS837.84; Lane 17, *P. macrostoma* var. *incolorata* CBS839.84; Lanes 18-20, *P. lingam* isolates Leroy, Peace-3 and P186-12; Lanes 21-23, *P. herbarum* isolates AI, AIV and G/5/2; Lanes 24-25, *P. chrysanthemicola* 90-64 and 91-27I; Lanes 26-29, *P. exigua* 92-180-1, *P. medicaginis* 94-335A1, *P. nebulosa* 92-74, and *P. pomorum* 91-177; Lane 30, Blank. FIG. 16D shows RAPD analyses of genetic variation among *Phoma* isolates with oligonucleotide primer UBC 736. Lanes 1 and 31, GeneRuler™ 1 kb DNA Ladder (MBI Fermentas); Lanes 2-11, *Phoma macrostoma* isolates 85-24B, 89-25A2, 94-26, 94-44B, 94-134, 94-359A, 95-54A1, 95-268B, 97-12B, and 97-15B2; Lane 12, *P. dennisii* var. *dennisii* CBS135.96; Lanes 13-16, *P. macrostoma* var. *macrostoma* isolates CBS154.83, CBS482.95, CBS488.94 and CBS837.84; Lane 17, *P. macrostoma* var. *incolorata* CBS839.84; Lanes 18-20, *P. lingam* isolates Leroy, Peace-3 and P186-12; Lanes 21-23, *P. herbarum* isolates AI, AIV and G/5/2; Lanes 24-25, *P. chrysanthemicola* 90-64 and 91-271; Lanes 26-29, *P. exigua* 92-180-1, *P. medicaginis* 94-335A1, *P. nebulosa* 92-74, and *P. pomorum* 91-177; Lane 30, Blank.

Figure 17:
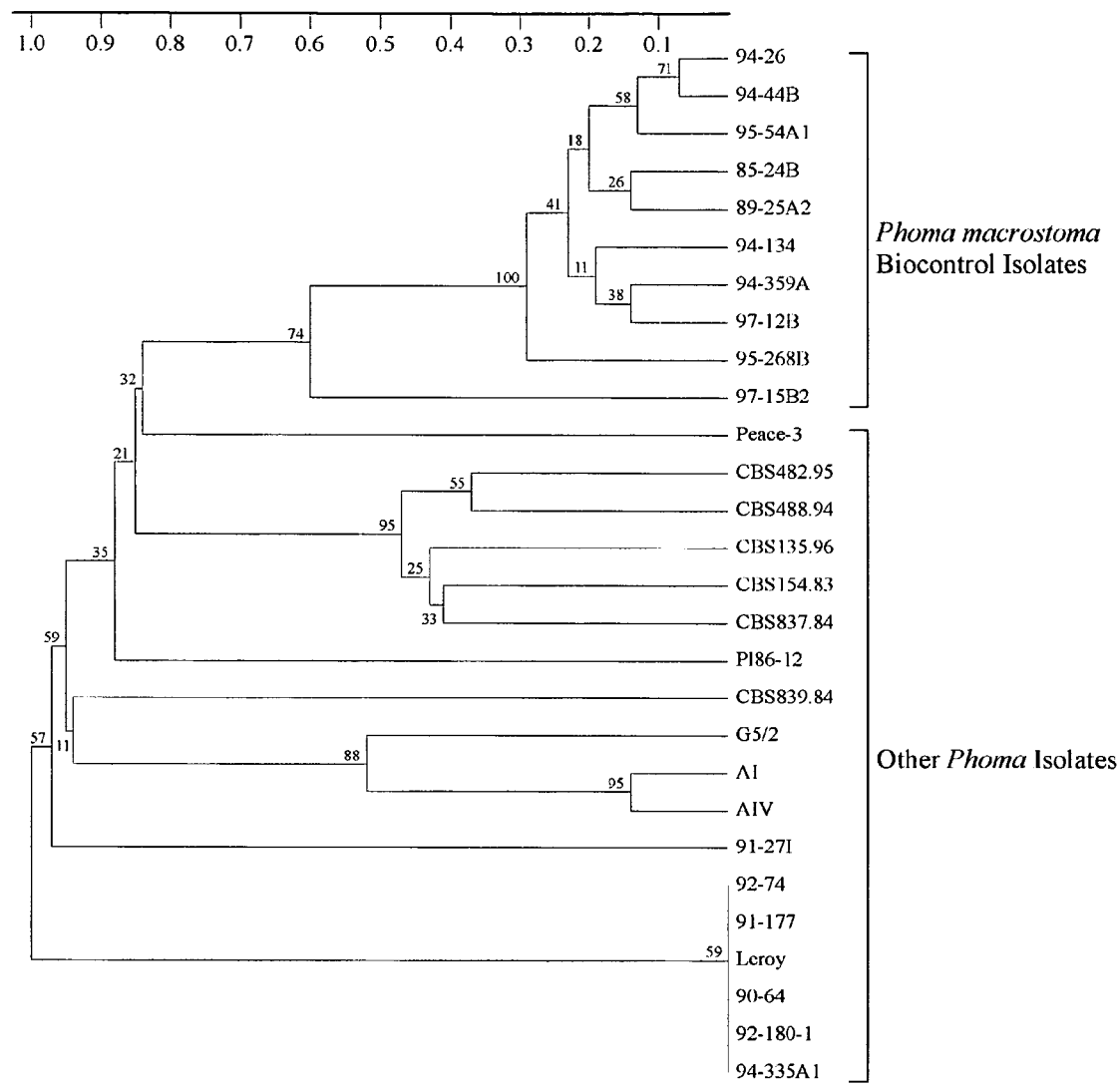

FIG. 17 shows the phylogenetic relationship among biocontrol isolates of *Phoma macrostoma* and 18 reference isolates from other genera of *Phoma* generated by Treecon® for Windows with the RAPD data. The biocontrol isolates were clustered together and genetically distinct from the reference isolates. Within the cluster of biocontrol isolates, the isolates originating from two different Canadian ecozones were randomly scattered. The evolutionary distance scale was placed at top of figure and a bootstrap value was presented on each node of the tree. With the exception of a small group basal to the tree, which was only supported by 59% of bootstrap replicates, strong statistical support was evident for all major clusters.

FIG. 18 shows internal transcribed spacer (ITS) PCR amplification using universal fungal primers ITS4 and ITS5. FIG. 18A shows Lane 1, Low Mass Ladder, Lanes 2-30, ATCC24524, ATCC46580, CBS112.36, CBS115.12, CBS154.83, CBS185.25, CBS198.69, CBS297.36, CBS482.95, CBS483.66, CBS488.94, CBS560.70, CBS598.94, CBS837.84, CBS839.84, DAOM175135, DAOM175940, DAOM175951, CCM-F322, CCMF-323, ICMP2325, ICMP2715, ICMP3173*, ICMP6603. ICMP6628, ICMP6803, ICMP6814, ICMP7033, ICMP10843. *ICMP3173 failed to amplify, and was re-analysed as shown in FIG. 18C. FIG. 18B shows Lane 31, Low Mass Ladder, Lanes 32-53, ICMP10963, ICMP11186, ICMP12948, IMI118020, IMI175661, IMI299239, IMI336757, IMI336761, WAC7881, SRC85-24B, SRC89-25A2*, SRC94-26, SRC94-26AVIR, SRC94-44B, SRC94-134, SRC94-359A, SRC95-54A1, SRC95-54A2, SRC95-268B, SRC97-12B, SRC97-15B2†, SRC02-2A; Lane 54, empty. *SRC89-25A2 failed to amplify, and was re-analysed as shown in FIG. 18C. †The culture of SRC97-15B2 was found to be contaminated and so it was resuscitated from stock cultures and the DNA extracted for re-analysis as indicated below (FIG. 18D). FIG. 18C shows Lane 1, Low Mass Ladder, Lanes 2-29; ICMP10963, ICMP11186, ICMP12948, IMI118020, IMI175661, IMI299239, IMI336757, IMI336761, WAC7881, SRC85-24B, SRC89-25A2*, SRC94-26, SRC94-26AVIR, SRC94-44B, SRC94-134, SRC94-359A, SRC95-54A1, SRC95-54A2, SRC95-268B, SRC97-12B, SRC97-15B2†, SRC02-2A, ICMP3173*, SRC89-25A2*, ICMP3173*, SRC89-25A2*, ICMP3173*, SRC89-25A2*; Lane 30, empty. *All re-amplified cultures that failed in previous analyses returned positive responses. ICMP3173 and SRC89-25A2 appear in multiples at the right of the gel under differing DNA concentrations. It can be seen in Lanes 26 and 27 that lower DNA concentrations failed to amplify the product of interest. †The source of DNA for isolate SRC97-15B2 is the same as that outlined in FIG. 18B. FIG. 18D shows DNA from the resuscitated isolate. FIG. 18D shows Lane 1, Low Mass Ladder, Lanes 2-24, MA1908B, PFC2705, CBS300.36, olrim779, PFC3313, olrim776, WAC7788, CBS297.36, CBS371.61, CBS529.66A, SRC97-15B2*, CBS529.66B, MA3312, MA1908R, CBS223.69, IMI192267, PD68/1014A, DAOM179750, CBS109173†, SRC03-1A8, IMI192268, PD68/1014B, CBS345.97; Lane 25, empty. *Sequence analysis of DNA from SRC97-15B2 following re-cultivation and re-extraction yielded a sequence identical to the other isolates from Canada thistle. One new isolate collected in 2003, SRC03-1A8, was also included in the analysis, along with the type cultures CBS223.69 and CBS529.66 and several other isolates.

Figure 19A-2:
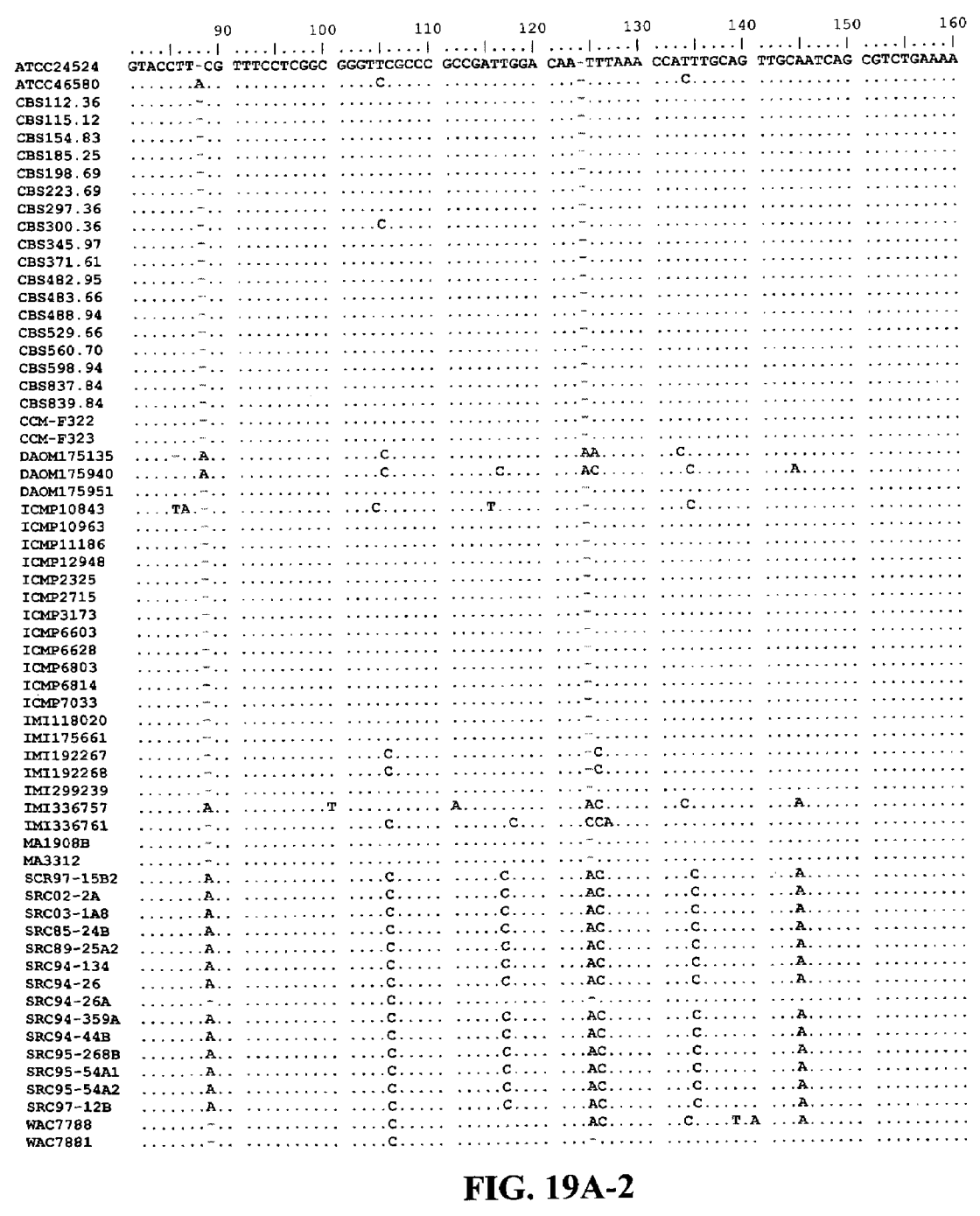

FIG. 19 shows ribosomal DNA ITS sequences for various *Phoma macrostoma* isolates. FIG. 19A shows sequence alignments of ITS sequences of *Phoma macrostoma* isolates in Table 5 taken from various hosts and geographic locations. FIG. 19B shows a non-limiting example of an ITS sequence for a *Phoma macrostoma* isolate that exhibits weed control activity, the nucleotide sequence for isolate SCR970-15B2 is shown in this example (SEQ ID NO:15).

Figure 20:
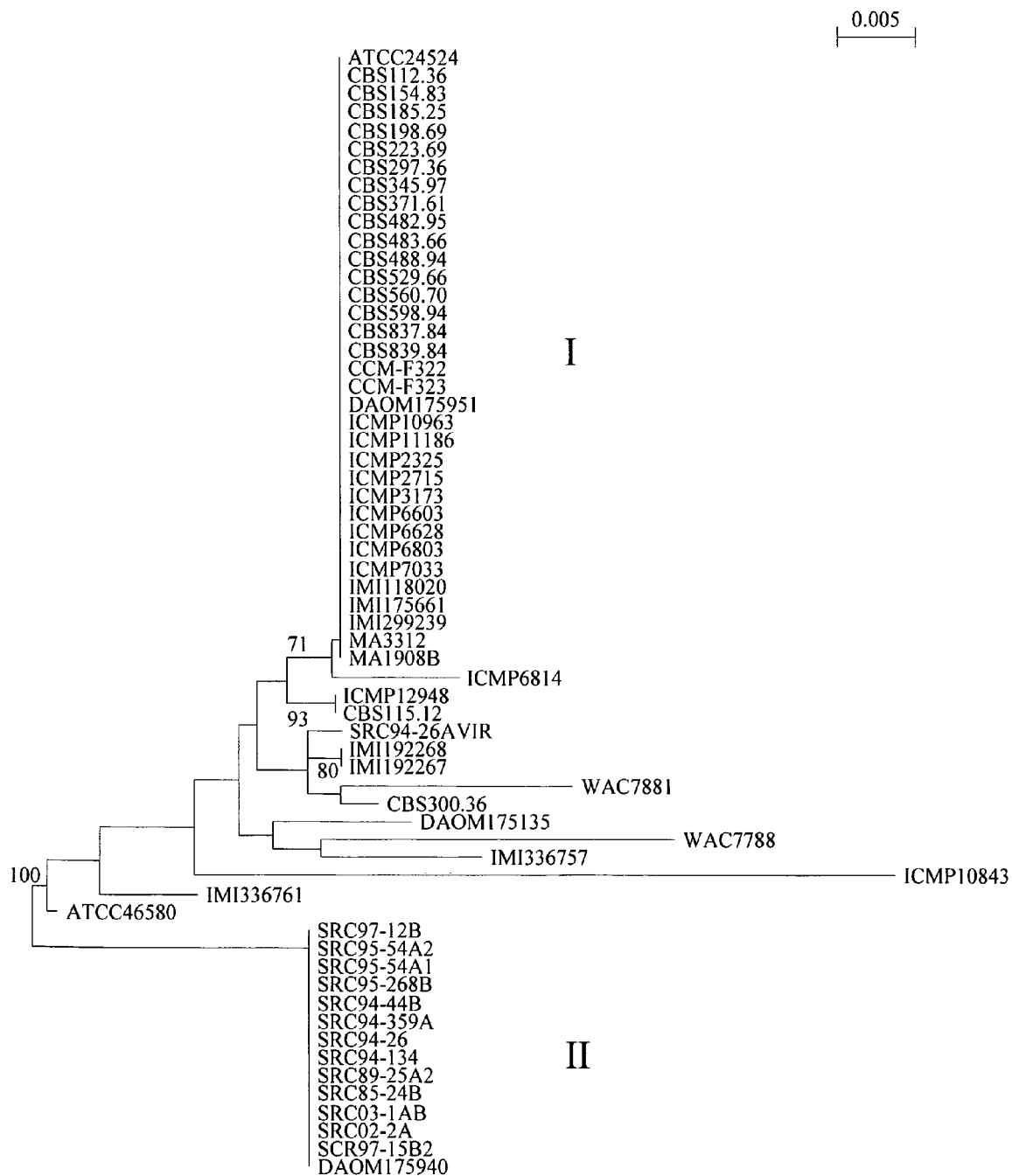

FIG. 20 shows a neighbour-joining tree of ribosomal DNA ITS sequences of *Phoma macrostoma* from Table 5 taken from various hosts and geographic locations. Bootstrap values of 70 or greater (percentage of 1000 replicates) are indicated, rounded to the nearest integer. Branch lengths are proportional to genetic distance, which is indicated by a bar at the upper right.

Figure 21:
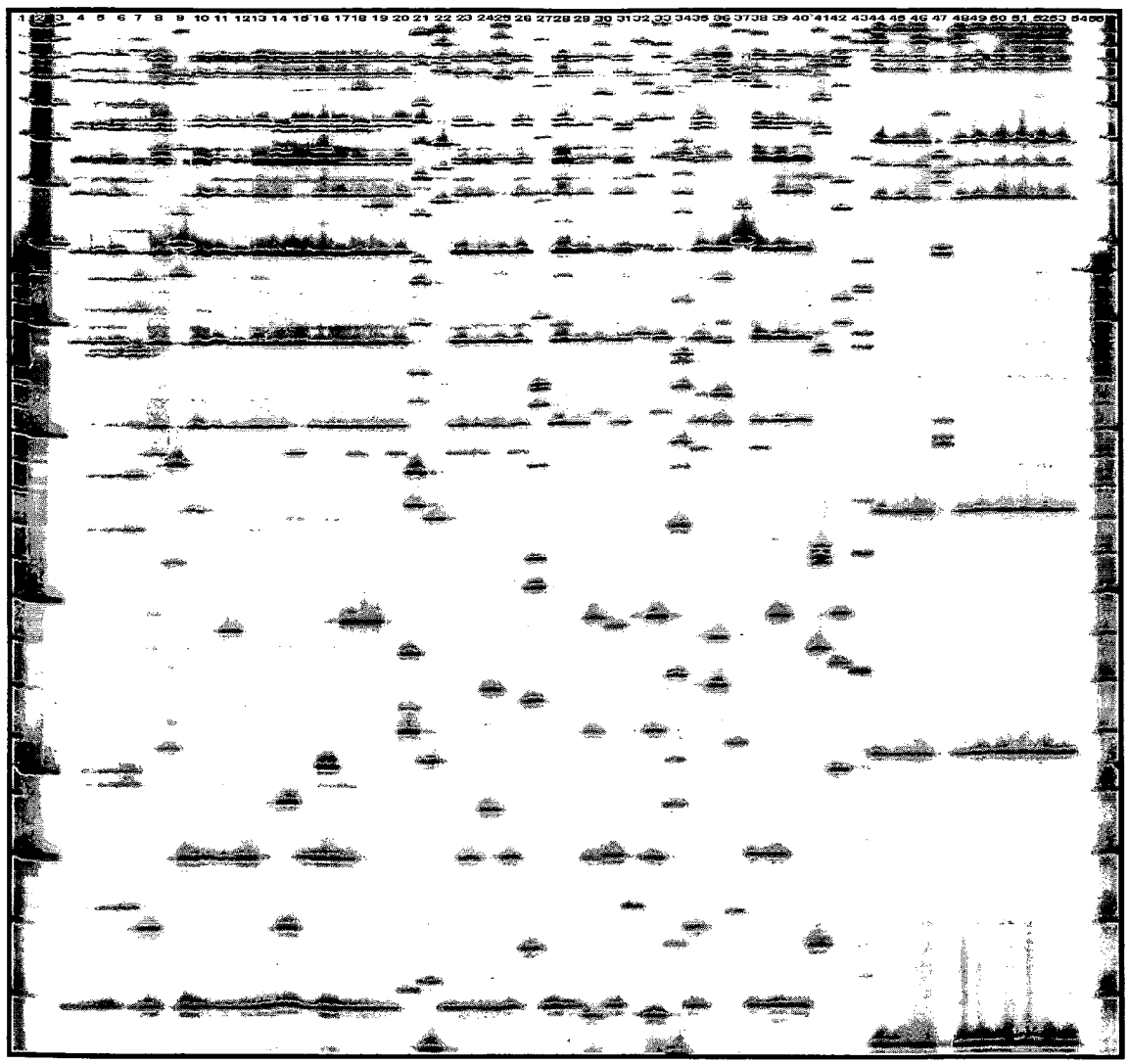

FIG. 21 shows an amplified fragment length polymorphisms (AFLP) gel of primer combination E-AC and M-CA showing unique patterns of isolates from Canada thistle (lanes 22, 44-53). Lane 1, 10 bp ladder (Invitrogen); Lane 2, 50 bp ladder (Invitrogen); Lanes 3-5, empty (seepage from other lanes). Lanes 6-53, ATCC24524, ATCC46580, CBS112.36, CBS115.12, CBS154.83, CBS185.25, CBS198.69, CBS297.36, CBS482.95, CBS483.66, CBS488.94, CBS560.70, CBS598.94, CBS837.84, CBS839.84, DAOM175135, DAOM175940*, DAOM175951, CCM-F322, CCMF-323, ICMP2325, ICMP2715, ICMP3173, ICMP6603. ICMP6628, ICMP6803, ICMP6814, ICMP7033, ICMP10843, ICMP10963, ICMP11186, ICMP12948, IMI118020, IMI175661, IMI299239, IMI336757, IMI336761, WAC7881, SRC85-24B, SRC89-25A2, SRC94-26, SRC94-26AVIR, SRC94-44B, SRC94-134, SRC94-359A, SRC95-54A1, SRC95-54A2, SRC95-268B; Lane 54, empty, Lane 55, 10 bp ladder; Lane 56 (not marked), 50 bp ladder. *Note:

DAOM175940 (lane 22), possesses an identical genetic fingerprint to other isolates from Canada thistle. Gel image does not include isolates WAC7788, IMI192267, IMI192268, CBS300.36, MA1908B, CBS223.69, CBS345.97, CBS371.61, CBS529.66, MA3312, SRC97-12B, SRC97-15B2, SRC02-2A and SRC03-1A8 that were separated on another gel.

Figure 22:
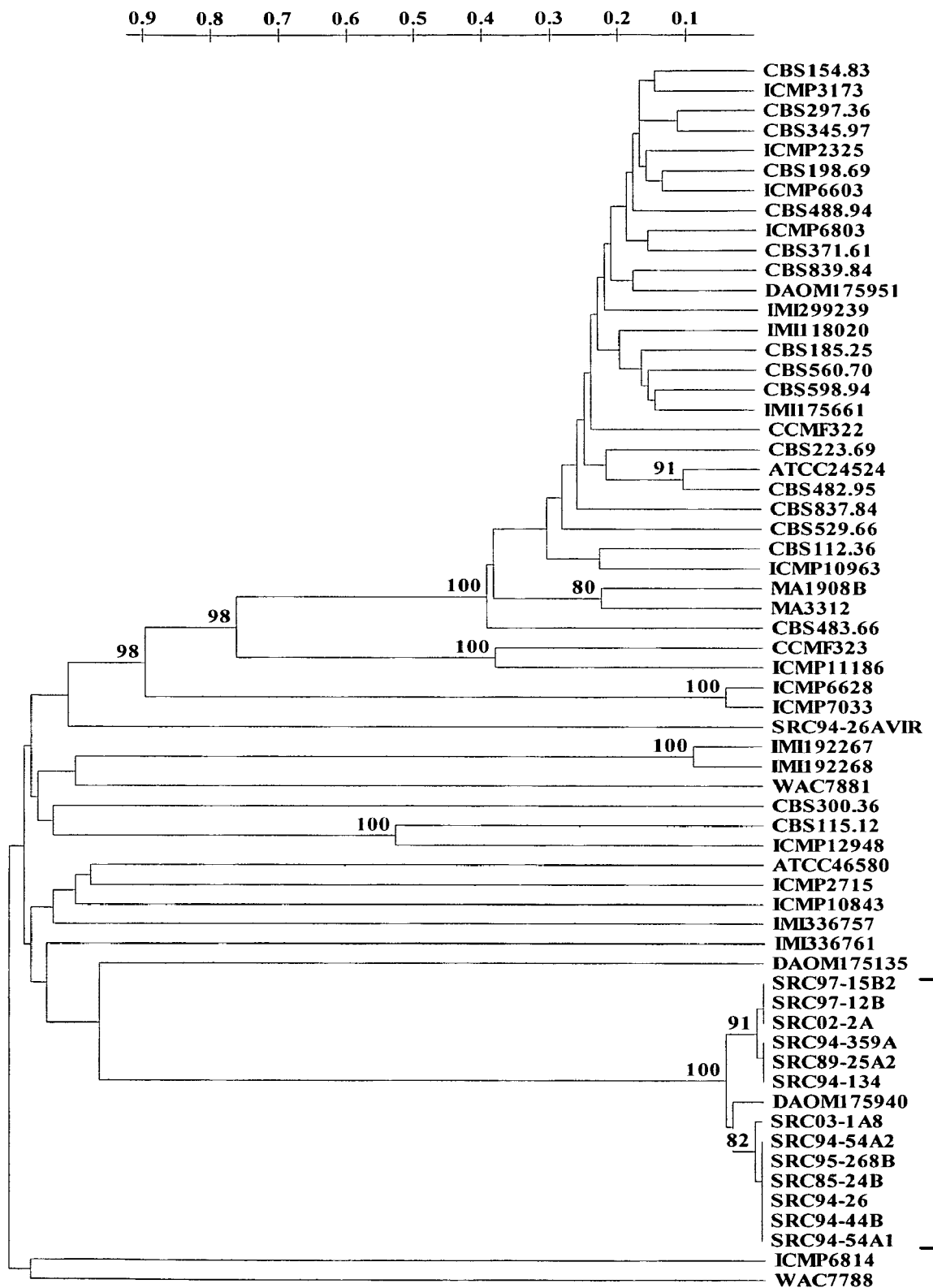

FIG. 22 shows an UPGMA dendrogram of AFLP products of *Phoma macrostoma* isolates collected from various hosts and geographic locations. Isolates possessing bioherbicidal activity and collected from Canada thistle form a monophyletic cluster shown by a border to the right. Bootstrap values of 70 or greater (percentage of 1000 replicates) are indicated, rounded to the nearest integer. Branch lengths are proportional to genetic distance, which is indicated by a bar at the top of the figure.

DETAILED DESCRIPTION

The present invention relates to bioherbicides. More specifically, the present invention relates to fungal bioherbicides and compositions comprising fungal bioherbicides as well as method for detecting fungal bioherbicides.

The following description is of a preferred embodiment.

By the term "controlling weed growth", or "weed control activity" it is meant that one or more fungal isolates, an extract therefrom, an inoculated broth therefrom, or a combination thereof, when applied on or near a weed interferes with the normal growth and development of a weed. Examples of weed growth control activity include, but are not limited to, inhibition of root growth, inhibition of shoot growth, inhibition of shoot emergence, reduction of weed biomass inhibition of seed production, or the ability to induce chlorosis, or reduce competitiveness of a weed for water, nutrients, or a combination thereof, that would otherwise be utilized by a crop plant. Alternatively, the fungal isolate may be capable of controlling weeds by killing them. It is preferred that a fungal isolate selectively controls weed growth, and does not have any substantial effect on a plant for which growth is desired, for example a non-target plant such as an agriculturally important plant, or a residential or commercial grass.

Fungal isolates that control weed growth or the exhibit weed control activity may be characterized as having a Weed Control Index (WCI) of between about 20% to 100% (the higher the WCI, the more efficacious the fungal isolate). The WCI includes either an annual WCI (WCIA) or a perennial WCI (WCIP) as defined below. Preferably, fungal isolates are characterized as having a WCI of between about 50% to 100%. More preferably, the fungal isolates have a WCI of between about 70% to 100%. However, it is to be understood that a fungal isolate with a low WCI may still prove effective to help control weed growth and provide a non-target plant a competitive advantage over one or more weeds. Furthermore, it may be desirable to use one or more fungal isolates that exhibit a low WCI in order to ensure that a non-target plant is not affected by the bioherbicide.

The weed control Index is determined using either WCIA for evaluation of annual weeds, or WCIP, for evaluation of perennial weeds, as follows:

$$WCIA=\{[(100-FFW)+(\% M)+(\% IOC)]/300\}\times 100\%$$

$$WCIP=\{[(100-RW)+(100-FFW)+(\% M)+(\% IOC)]/400\}\times 100\%$$

where RW - is root weight
FFW—is foliar fresh weight;
M—is mortality; and
IOC—is incidence of chlorosis, as determined by number of plants with a rating of 3-6, where, 1=healthy, dark green foliage; 2=slightly yellow-green foliage; 3=leaves primarily yellow, some yellow-green; 4=leaves primarily white, a few yellow-green; 5=plants completely white; and 6=plants dead.

By "fungal isolate" or "biocontrol agent" it is meant a biologically active *Phoma macrostoma* isolate (may also be refered to as *Phoma* cf. *macrostoma*), or a biologically active fragment, component, obtained or isolated from *Phoma macrostoma*. By fragment or component of a fungal isolate, it is meant a fragment of the mycelium, or one or more spores, pycnidia, conidia, chlamydospores or a combination thereof, obtained from the fungi. Fungal isolates may be obtained from small chlorotic and necrotic lesions on leaf and stem tissues of a desired weed, for example but not limited to Canada thistle and assayed for weed growth control activity, as described herein or using standard methods as would be known to one of skill in the art. The fungal isolates of the present invention which exhibit weed control activity are strains of *Phoma macrostoma*. Examples of *Phoma macrostoma* isolates, which may be used according to the present invention, and which are not to be considered as limiting in any manner, include:

85-24B (IDAC 230201-1, deposited Feb. 23, 2001),
89-25A (IDAC 110401-1, deposited Apr. 11, 2001),
94-26 (IDAC 230201-2, deposited Feb. 23, 2001),
94-44B (IDAC 230201-3, deposited Feb. 23, 2001)
94-134 (IDAC 230201-4, deposited Feb. 23, 2001),
94-359A (IDAC 110401-2, deposited Apr. 11, 2001),
95-54A1 (IDAC 230201-5, deposited Feb. 23, 2001),
95-268B (IDAC 110401-3, deposited Apr. 11, 2001),
97-12B (IDAC 230201-6, deposited Feb. 23, 2001),
97-15B2 (IDAC 110401-4, deposited Apr. 11, 2001), or a combination thereof. The *Phoma* cf. *macrostoma* isolates are deposited at the International Depositary Authority of Canada (IDAC), Bureau of Microbiology, Health Canada, 1015 Arlington Street, Winnipeg, Manitoba, R3E 3R2 Canada. These isolates originate from Canada thistle (*Cirsium arvense*) and are shown to exhibit biocontrol activity (see Example 2). The present invention therefore provides that the *Phoma macrostoma* isolate of the present invention originates from Canada thistle (*Cirsium arvense*). *Phoma macrostoma* isolates originating from sources other than Canada thistle may also exhibit biocontrol activity, for example, isolate SRC02-2A, which originates from *Lens culinaris* (see Table 5) and exhibits weed control activity (see Example 2). Therefore, the present invention further provides that the *Phoma* cf *macrostoma* isolate, an extract therefrom, or an inoculated broth therefrom may be obtained from other plant sources, providing that the isolate exhibits weed control activity.

By "extract", it is meant an aqueous or solvent extract, crude or in a more purified state, comprising one or more active compounds obtained from a fungal isolate, that in the proximity of, or when applied onto, a weed is capable of controlling weed growth.

By an "inoculated broth", it is meant the broth obtained from a culture of one or more than one *Phoma* isolates (see Example 5) as defined herein, that comprise one or more active compounds capable of controlling weed growth. An inoculated broth may be concentrated using methods known in the art, for example, but not limited to evaporation, rotoevaporation or freeze drying.

By "saturation" it is meant the maximum retention capacity of a soil, and is defined as occurring when the soil pores in the upper part of the soil are filled with water. By "field capacity" or "field moisture capacity", it is meant the percentage of water remaining in a soil two or three days after having been saturated and after free drainage has essentially ceased.

By "permanent wilting point" it is meant the critical moisture of soil at which plants wilt and fail to recover turgidity when placed in a dark and humid atmosphere.

In a preferred embodiment, the *Phoma macrostoma* isolate is formulated in a biocontrol composition comprising one or more *Phoma macrostoma* isolates, one or more extracts obtained from a *Phoma macrostoma* isolate, an inoculated broth, or a combination thereof. The biocontrol composition is preferably added to soil, added to compost, added to peat-type pellets, added to or used to coat a planting medium, for example but not limited to wood chips, used to coat or treat plant seed in the presence of a binder, for example but not limited to methylcellulose, starch, clay, sugar or a combination thereof, or applied to a plant, for example but not limited to, spraying or rubbing on a plant, to control weeds. Furthermore, liquid injection may be used to apply one or more isolates, for example, spores or mycelia, extracts obtained from fungal isolates, inoculated broth, or a combination thereof, to soil. Liquid injection may used for perennial applications, for example but not limited to turf grass management.

By the term "biocontrol composition", it is meant a composition comprising one or more than one biocontrol agent of the present invention within a suitable medium. A biocontrol agent consists of one or more *Phoma macrostoma* isolates as defined above, an inoculated broth therefrom, an extract therefrom, or a combination thereof. For example, if the biocontrol composition comprises a *Phoma macrostoma* isolate, then the suitable medium may comprise a growth medium to maintain the viability of the *Phoma macrostoma* isolate before, and after application of the biocontrol composition to the soil. If an extract of a *Phoma macrostoma* isolate, one or more *Phoma macrostoma* isolates, or a combination thereof, is used for administration to a weed or soil, then the suitable medium may comprise stabilizing agents, surfactants and the like as would be known to one of skill in the art. For example, which is not to be considered limiting in any manner, media may include supplemented Agar, pesta, peat prills, vermiculite, clay, starches, potato dextrose broth (PDB), V8® (vegetable) juice broth, whole grain or grain fragments of, for example but not limited to, legume grains including lentil or chickpea, or cereal grain for example, wheat or barley, or corn, or any combination or variant thereof, provided that the medium allows the *Phoma macrostoma* isolate to remain viable.

Pesta is a term for a granular product made from cereal grain flour and a biocontrol agent. The process encapsulates biocontrol agents in pasta-like products called pesta (Connick et al., 1991, which is incorporated herein by reference). Bacteria formulated in such media may exhibit extended shelf and field-life (e.g. Connick et al., 1996; Connick et al., 1998). These characteristics are desired in a product which may be stored prior to use or shipped over long-distances prior to being used for weed control in a field. Therefore, the biocontrol compositions comprising *Phoma macrostoma* isolates of the present invention may be formulated in a suitable medium for example, but not limited to, pesta.

If the suitable medium is a growth medium, then the growth medium may comprise any liquid, semi-liquid or solid medium which allows the *Phoma macrostoma* isolates of the present invention to grow or remain viable. Any growth medium known in the art which is capable of supporting the fungal isolate may be employed. Examples of suitable growth media, which are not to be considered limiting in any manner, include potato dextrose agar, potato dextrose broth, V8® (vegetable) juice broth and the like. Preferably, the growth medium is a solid medium, for example but not limited to grain, for example whole grain or fragments thereof, for example but not limited to, legume grains including lentil or chickpea, or cereal grain for example, wheat or barley, or corn (see Example 3). The growth medium should also permit an effective amount of the *Phoma macrostoma* isolate to remain viable after being applied to the soil of a crop for a suitable period of time, for example but not limited to, up to about 7 days to about 18 months after application. Preferably, the isolate remains viable from about 14 days to about 12 months, and more preferred, from about 14 days to about 90 days. For soil application, spores, mycelia (growing on grain), or spores and mycelia growing on grain may be mixed together and either applied onto, or mixed with, soil. Furthermore, liquid injection may be used to apply one or more isolates, for example, spores or mycelia, extracts obtained from fungal isolates, or a combination thereof, to soil. Typical application rates for a fungal isolate that was grown on the preferred growth medium include, but are not limited to, 0.001 kg/m$^2$ to 5 kg/m$^2$ using a particle size between 49-840 microns and particle viability of 60-100%. The preferred rate of application is 0.1 kg/m$^2$ to 1.0 kg/m$^2$. However, any application rate that results in weed control activity may be employed.

When one or more *Phoma macrostoma* isolates are applied using a solid medium, for example hulless barley, the infested barley grain prepared as described in Example 3 may be ground prior to application to soil. Any suitable granule size may be used, for example, from about 50 µ to about 1 mm. The preferred viability of the particles used for application is about 60-100%. As shown in Table 25 (Example 3), with smaller granule size, a lower application dose rate (g/m$^2$) will achieve a similar, or better, weed control activity.

It is also contemplated by the present invention that more than one *Phoma macrostoma* isolate may be used to control weeds. Similarly, a biocontrol control agent or biocontrol composition of the present invention may comprise more than one *Phoma macrostoma* isolate. Multiple *Phoma macrostoma* isolates capable of controlling a specific weed may be used or multiple *Phoma macrostoma* isolates, each of which is capable of controlling a distinct type of weed may be mixed and used as described herein. It is also preferred that the biocontrol agent or biocontrol composition exhibit host selectivity, in that weed control activity is observed in one or more target weeds, while no weed control activity is observed on non-target plants. Examples of non-target plants include agriculturally important plants, and domestic or commercial grasses (Gramineae).

By weed, it is meant any undesired plant. Preferably, a weed is a broad-leaf (dicot) weed, for example but not limited to members of the Compositae, Caryophyllaceae, Polygonaceae, Convolvulaceae, Plantaginaceae and Rubiaceae. More preferably, a weed is selected from the group consisting of:

Compositae (Composite family): including dandelion [*Taraxacum officinale* L.], ox-eye daisy [*Chrysanthemum leucanthemum*], burdocks for example common burdock [*Arctium minus*], goat's beards [e.g. *Tragopogon dubius*], cockleburs [e.g. *Xanthium strumarium*], ragweeds for example common ragweed [*Ambrosia artemisiifolia*] or giant ragweed [*Ambrosia trifolia*], scentless chamomile [*Matricaria perforata* Mérat.], sow-thistles, for example perennial sowthistle [*Sonchus arvensis* L.], and thistles, for example Canada thistle [*Cirsium arvense* L.(Scop.)];

Caryophyllaceae (Pink Family): including chickweed [*Stellaria media* (L.)Vill.];

Polygonaceae (Buckwheat Family): including wild buckwheat [*Polygonum convolvulus* L.];

Convolvulaceae (Morning Glory Family): including field bindweed [*Convolvulus arvensis* L.];

Plantaginaceae (Plantain Family): including plantain [*Plantago lanceolata*]; or Rubiaceae (Rubus family): including false cleavers (*Gallium spurium*)

The biocontrol agent, biocontrol composition, or both, of the present invention may be added to the soil where the seed either grows or may grow. The soil may be mixed so that one or more biocontrol agent are in close proximity to the root system or root fragments of the weeds. It is also preferable that the biocontrol agent be in close proximity to weed seeds when such seeds are present. Alternatively, the biocontrol agent, biocontrol composition, or both, of the present invention may be added directly to the weed.

The biocontrol agent and biocontrol compositions of the present invention may be applied to soil or weed by any method known in the art such as, but not limited to dusting, rubbing, spreading, drilling, banding, broadcasting (with or without incorporation), spraying, liquid injection, pouring or soil drenching. The biocontrol agent and biocontrol compositions may also be applied at any suitable time, for example but not limited to, during or after soil tillage. Preferably, the biocontrol agent and biocontrol composition is applied during the spring, or early summer. Solid preparation of the biocontrol agent, or biocontrol composition for example but not limited to infested barley grain, is added to soil in the amount of about 0.1 kg/m$^2$ to about 5 kg/m$^2$. Liquid suspensions of about $10^3$ to about $10^9$ cfu/mL, may be applied at a rate of about 1 L/m$^2$ to about 5 L/m$^2$. However, any amount that results in weed controlling activity may be applied.

It is also within the scope of the present invention, that extracts obtained from one or more *Phoma macrostoma* isolates may be formulated and applied to the soil or weed as a liquid, for example as a spray, injection, drench, rubbing, dusting, or as a solid, including autoclaved infested barley granules dusting or rubbing of suitably formulated extracts. As one of skill will be able to determine, appropriate dosages will depend upon the concentration of active components within the extract or solid. Preferably, the extract is derived from either a 4 week old crude broth concentrated about 100× the original volume, or from an extract obtained from a 3:1 ratio of extracted mycelium to methanol. An example, which is not to be considered limiting, of an application rate of such extracts is from about 0.1 to about 2.5 L/m$^2$, depending upon the concentration of active ingredients. However, any amount that results in weed controlling activity may be applied.

A biocontrol agent, or a biocontrol composition, of the present invention comprising one or more *Phoma macrostoma* isolates, one or more extracts obtained from a fungal isolate, an inoculated broth, or a combination thereof may be added to a planting medium, for example compost, or it may be added to or used to coat alternate planting media, for example but not limited to wood chips, landscaping cloth, vermiculite and the like, as would be evident to one of skill in the art. Furthermore, the biocontrol agent or biocontrol composition as described herein may be used to coat or treat plant seed. Coated seed may involve the use of a binder, for example but not limited to methylcellulose, starch, clay, sugar or a combination thereof.

Therefore, according to the present invention, there is provided a method of controlling a range of weeds with a bioherbicide comprising one or more *Phoma macrostoma* isolates, a biocontrol agent, or a biocontrol composition comprising one or more *Phoma macrostoma* isolates, an extract obtained from one or more *Phoma macrostoma* isolates, an inoculated broth, or a combination thereof. *Phoma macrostoma* isolates, or a combination thereof, which may be employed to control weed growth include, but are not limited to those listed in Table 1 below.

TABLE 1

Fungal Isolates Information and Target Weeds Affected

| Fungal isolate | Target Weed | Deposit information |
| --- | --- | --- |
| 95-54A1 | Canada thistle, Scentless chamomile, False cleavers, Chickweed, Field bindweed, Dandelion, Plantain, Prairie sunflower, | IDAC 230201-5* |
| 97-12B | Canada thistle, Dandelion, Scentless Chamomile, False cleavers, Perennial sowthistle, Chickweed | IDAC 230201-6* |
| 97-15B2 | Canada thistle, Scentless chamomile, False cleavers, Chickweed, Wild buckwheat, Prairie sunflower | IDAC 110401-4** |
| 94-359A | Scentless chamomile, Canada thistle, Dandelion | IDAC 110401-2** |
| 89-25A | Canada thistle, scentless chamomile, dandelion, Prairie sunflower | IDAC 110401-1** |
| 85-24B | Canada thistle, Dandelion, Scentless chamomile, False cleavers, Prairie Sunflower, chickweed, Plantain, wild buckwheat | IDAC 230201-1* |
| 94-26 | Canada thistle, Dandelion, Scentless chamomile, False cleavers, Perennial sowthistle, Chickweed, Plantain, wild buckwheat | IDAC 230201-2* |
| 94-44B | Canada thistle, Dandelion, Scentless chamomile, False cleavers, Perennial sowthistle, Chickweed, Wild buckwheat, Plantain, Prairie sunflower | IDAC 230201-3* |
| 94-134 | Canada thistle, Chickweed, Wild buckwheat, Scentless chamomile, Plantain, False cleavers, | IDAC 230201-4* |
| 95-268B | False cleavers, Chickweed, Wild buckwheat, Scentless chamomile, Canada thistle, dandelion | IDAC 110401-3** |

*deposited Feb. 23, 2001 at the International Deposit Authority of Canada (IDAC), Bureau of Microbiology, Health Canada, 1015 Arlington Street, Winnipeg, Manitoba, R3E 3R2 Canada.
**deposited Apr. 11, 2001 at the International Deposit Authority of Canada (IDAC), Bureau of Microbiology, Health Canada, 1015 Arlington Street, Winnipeg, Manitoba, R3E 3R2 Canada.

Referring now to Table 2 (and see Example 2 for associated protocols) there is shown, as an example, weed control activity, as indicated by a reduction of foliar fresh weight, reduction in root weight, chlorosis, or mortality, in Canada thistle by a range of fungal isolates.

TABLE 2

Effect of fungal isolates on foliar fresh weight (FFW), root weight (RW), mortality (M) and incidence of Chlorosis (IOC) on Canada Thistle plants, and associated Weed Control Index (WCIP)

| Isolates | % FFW* | % RW* | % M | % IOC | WCIP** |
|---|---|---|---|---|---|
| Control | 100 ± 4 | 100 ± 5 | 1 ± 1 | 0 | 0 |
| 85-24B | 22 ± 6 | 25 ± 4 | 57 ± 7 | 86 ± 6 | 74 |
| 94-26 | 23 ± 7 | 26 ± 6 | 72 ± 7 | 83 ± 6 | 76 |
| 94-44B | 8 ± 3 | 15 ± 2 | 80 ± 5 | 96 ± 2 | 88 |
| 94-134 | 20 ± 8 | 26 ± 5 | 59 ± 11 | 74 ± 9 | 72 |
| 95-54A1 | 20 ± 10 | 23 ± 8 | 79 ± 8 | 82 ± 8 | 79 |
| 97-12B | 59 ± 13 | 53 ± 11 | 39 ± 11 | 61 ± 11 | 47 |
| 89-25A | 76 ± 13 | 63 ± 11 | 23 ± 8 | 36 ± 10 | 30 |
| 94-359A | 69 ± 13 | 63 ± 10 | 18 ± 9 | 43 ± 13 | 32 |
| 95-268B | 31 ± 7 | 32 ± 6 | 58 ± 8 | 75 ± 7 | 68 |
| 97-15B2 | 17 ± 4 | 17 ± 4 | 81 ± 8 | 89 ± 6 | 85 |

*% of control
**WCIP = {[(100 − RW) + (100 − FFW) + (% M) + (% IOC]/400} × 100%.

From Table 2, it can be noted that several fungal strains, for example but not limited to, 85-24B, 94-26, 94-44B, 94-134, 95-54A1, 97-12B, 95-268B and 97-15B2 are capable of reducing foliar fresh weight in Canada thistle from about 40% to about 92%, and of suppressing root weight by about 47% to about 85%, compared to the uninoculated control. These fungal isolates are characterized as having a WCIP from about 47 to 88% and they are effective in controlling weed growth which is supported by the observation that up to about 80% of the plants are killed by the treatment. Fungal isolates 89-25A and 94-359A are also effective at suppressing foliar fresh weight, root weight, and exhibit a WCIP of about 30-32%.

Therefore, the present invention is directed to a bioherbicide comprising fungal isolates 85-24B, 94-26, 94-44B, 94-134, 95-54A1, 97-12B, 89-25A, 94-359A, 95-268B, 97-15B2, or a combination thereof for the control of Canada thistle.

Figure 1:
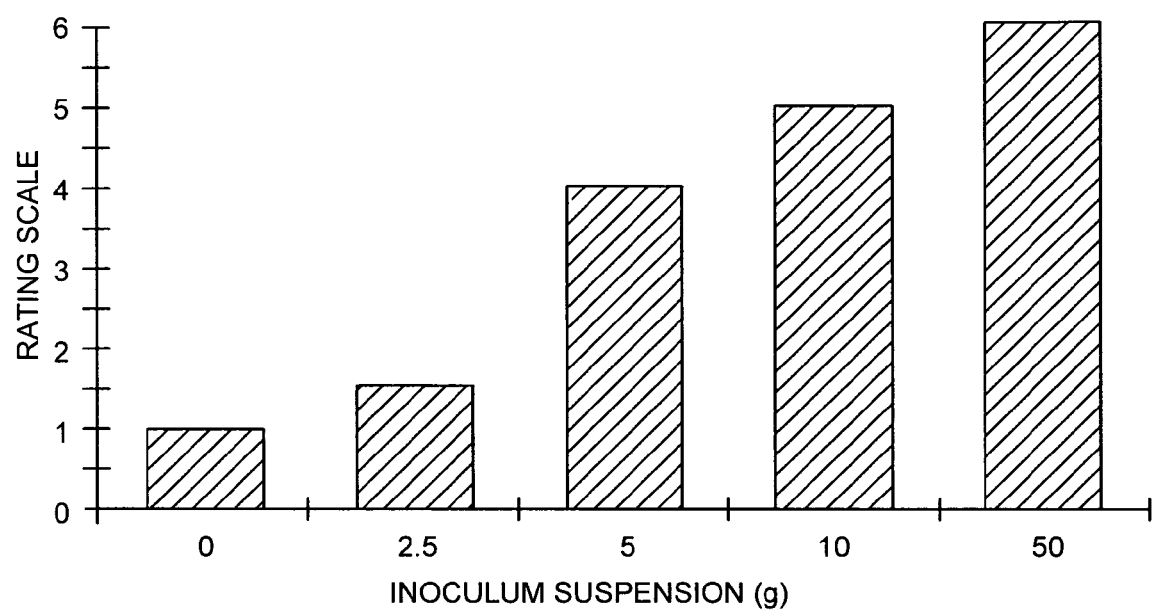
FIG. 1 shows the effect of different amounts of inoculum suspension 85-24B on Canada thistle plants. The Rating scale is: 1=healthy, dark green foliage; 2=slightly yellow-green foliage; 3=leaves primarily yellow, some yellow-green; 4=leaves primarily white, a few yellow-green; 5=plants completely white; and 6=plants dead.

Referring now to FIG. 1, there is shown the effect of an inoculum suspension comprising fungal isolate 85-24B on Canada thistle. FIG. 1 demonstrates that damage to Canada thistle was greater at higher inoculum levels. A dose in the range of about 5 g/0.01 m² to about 50 g/0.01 m² or higher is capable of controlling Canada thistle. Similar results were also observed by applying granules of infested barley grain to the soil.

Without wishing to be bound by theory, the *Phoma macrostoma* isolates as described herein may have the ability to weaken Canada thistle, or a range of other perennial or annual weeds, as described below, by affecting processes involved in plant growth and development, for example photosynthesis, the accumulation of storage products in the roots, reducing shoot emergence, reducing root growth, inducing symptoms of chlorosis (yellowing of plant leaves).

Characterization of the weed control activity of several *Phoma macrostoma* isolates of the present invention indicates that weed control activity of a *Phoma macrostoma* isolate may last about one growing season, depending upon the time of application of the fungal isolate to the soil or plant. With reference to Table 22 (Example 3), it is shown that spring or summer application of a fungal isolate exhibits weed control activity over one or more growth seasons. Fall application results in no observed weed control activity. Furthermore, as shown in Table 24 (Example 3), weed control activity increases with higher soil moisture content.

A number of *Phoma macrostoma* isolates were also tested to determine their efficacy at controlling weeds other than Canada thistle, for example, members of the Aster family including *Sonchus arvense* (perennial sowthistle), *Helianthus* (prairie sunflower), *Taraxacum officinale* (dandelion), *Matricaria perforata* (scentless chamomile), and other plants, including chickweed (*Stellaria media*), wild oats, green foxtail, and false cleavers (*Gallium spurium*).

Figure 2:
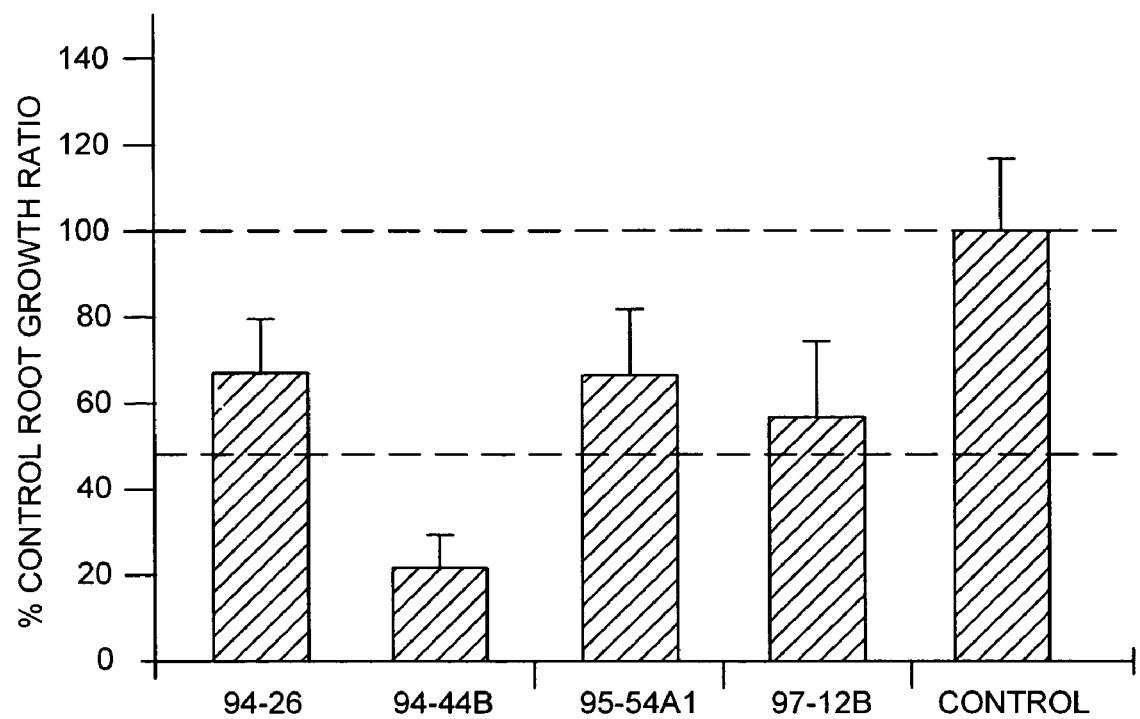
FIG. 2 shows the effect of fungal isolates 94-44B, 94-26, 95-54A1 and 97-12B on the root growth ratio of perennial sowthistle.
Figure 3:
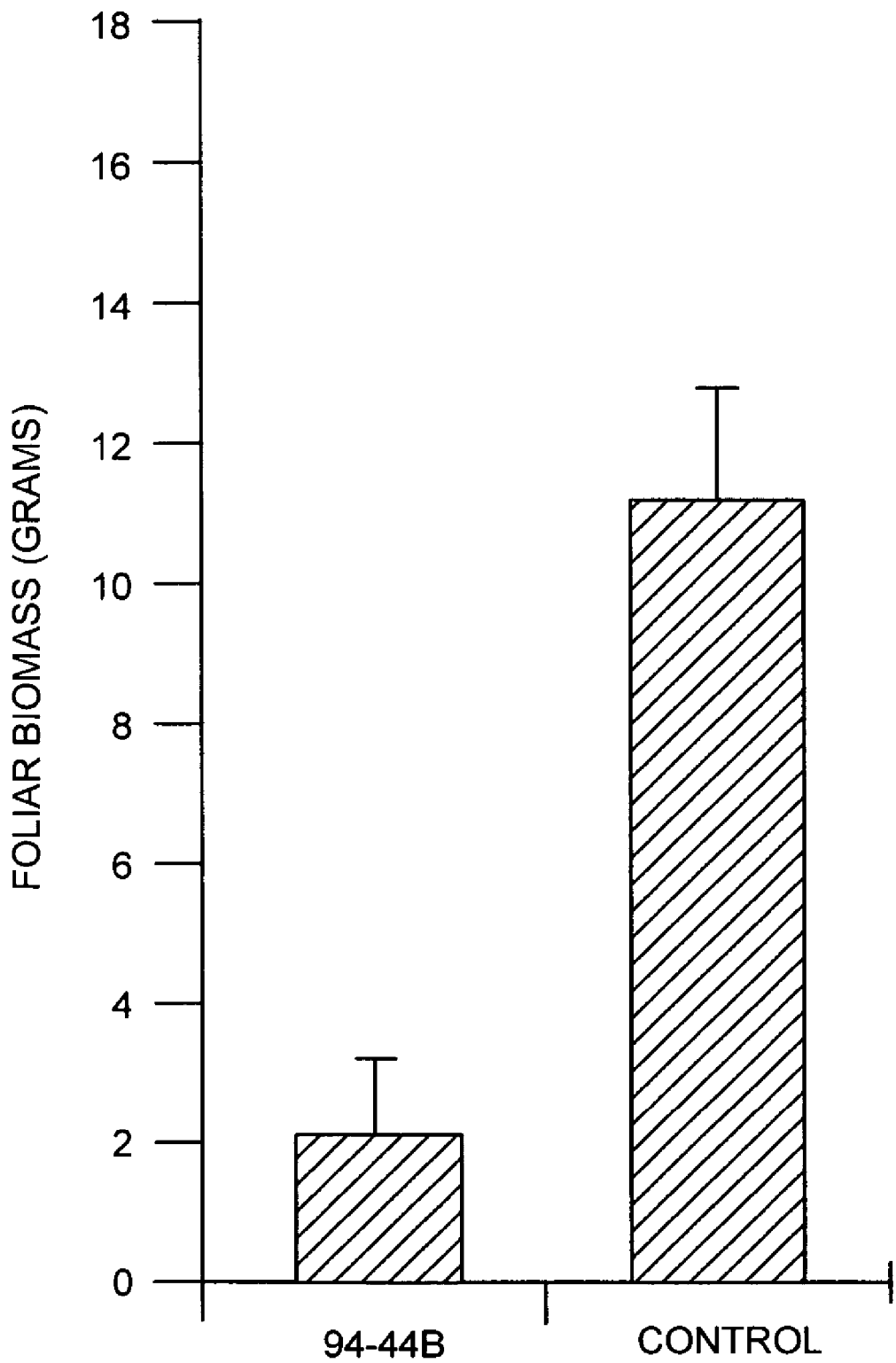
FIG. 3 shows the effect of fungal isolate 94-44B on foliar biomass of perennial sowthistle.
Figure 4:
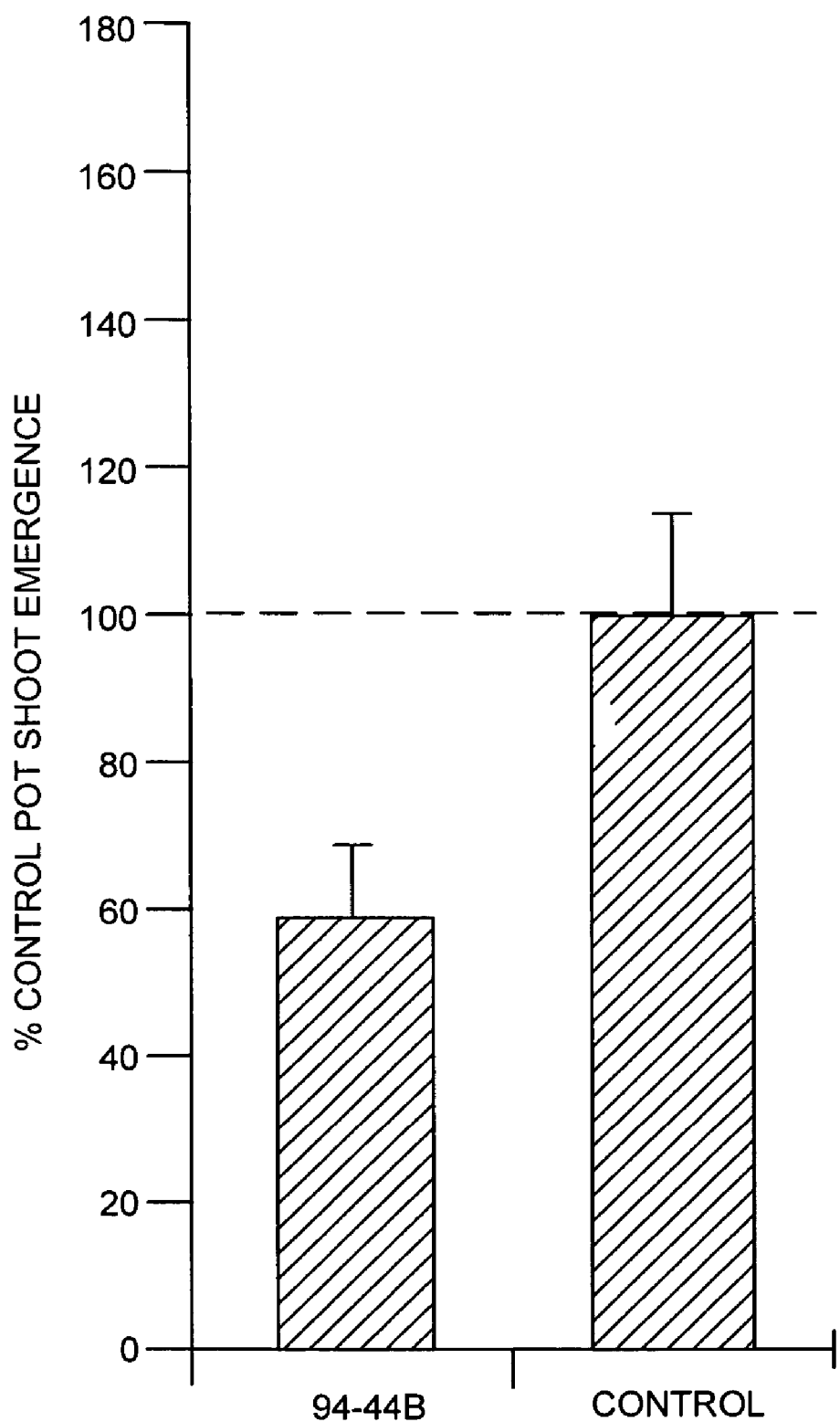
FIG. 4 shows the effect of fungal isolate 94-44B on shoot emergence of perennial sowthistle.
Figure 5:
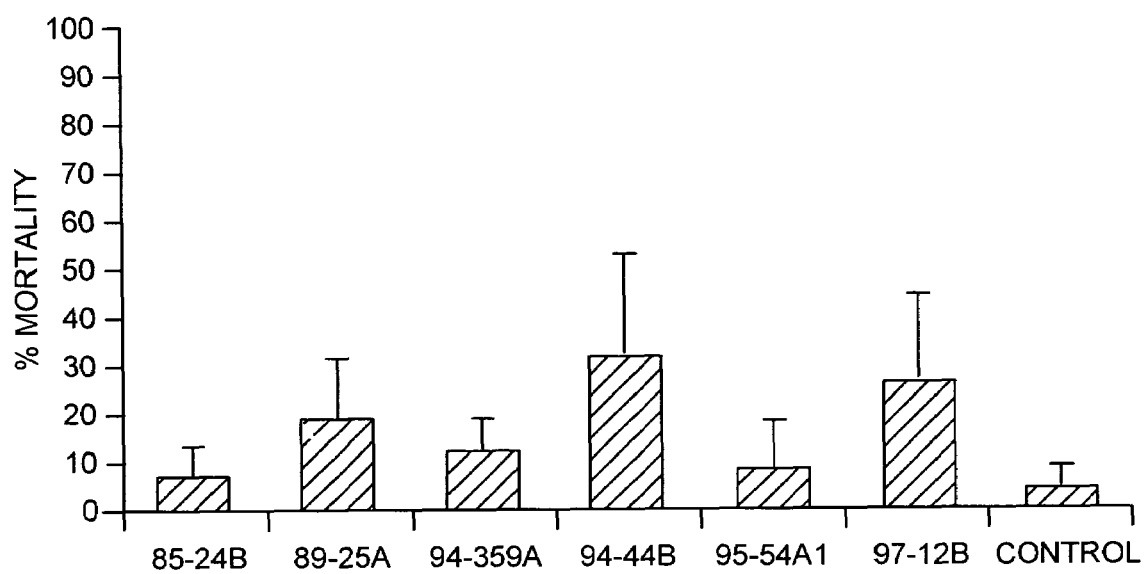
FIG. 5 shows a graphical representation of weed mortality following application of fungal isolate 94-44B, 89-25A and 97-12B to perennial sowthistle.

Fungal isolates 85-24B, 89-25A, 94-26, 94-359A, 94-44B, 94-134, 95-54A1, 95-268B, 97-15B2 and 97-12B were applied to perennial sowthistle using the inoculum mat bioassay described in Example 2. As shown in FIG. 2, fungal isolates 94-44B, 94-26, 95-54A1 and 97-12B reduced the weight of roots compared to the uninoculated control in greenhouse trials. A similar reduction in root weight was also observed with most of the other fungal isolates as indicated in Table 10 of Example 2. Further, fungal isolate 94-44B significantly reduced foliar biomass (FIG. 3) and reduced shoot emergence (FIG. 4) relative to the control. Three isolates (94-44B, 89-25A, and 97-12B) increased the mortality of the weed as shown in FIG. 5 and Table 10.

Therefore, fungal isolates 94-44B, 89-25A, 94-26, 95-54A1 and 97-12B, may be used to control perennial sowthistle (*Sonchus arvensis*). In a preferred embodiment, a biocontrol agent, or a biocontrol composition comprising 94-44B is used to control perennial sowthistle.

Similar results have been observed of the effect of these fungal isolates on other weeds, both perennial and annual weeds, as demonstrated by determining the WCI's for a range of weed species, for example as shown in Table 3 (also see Example 2).

TABLE 3

Weed control index (WCI) of fungal isolates on scentless chamomile (SC), false cleavers (FC), prairie sunflower (SF), chickweed (CH), wild buckwheat (WB), field bindweed (FB), perennial sow thistle (PST), dandelion (DA), and Canada thistle (CT).

| Isolate | SC* | FC* | SF* | CH* | WB* | FB* | PST** | DA** | CT** |
|---|---|---|---|---|---|---|---|---|---|
| No fungus | 7 | 4 | 0 | 0 | 0 | 3 | 0.1 | 0 | 0 |
| 85-24B | 79 | 30 | 84 | 76 | 92 | nd | 7 | 62 | 74 |
| 94-26 | 27 | 48 | nd | 91 | 39 | nd | 24 | 47 | 76 |
| 94-44B | 82 | 64 | 69 | 99 | 96 | nd | 58 | 59 | 88 |
| 94-134 | 82 | 54 | 6 | 59 | 85 | nd | 8 | 15 | 72 |
| 95-54A1 | 98 | 54 | 72 | 59 | 85 | nd | 8 | 15 | 72 |

TABLE 3-continued

Weed control index (WCI) of fungal isolates on scentless chamomile (SC), false cleavers (FC), prairie sunflower (SF), chickweed (CH), wild buckwheat (WB), field bindweed (FB), perennial sow thistle (PST), dandelion (DA), and Canada thistle (CT).

| Isolate | SC* | FC* | SF* | CH* | WB* | FB* | PST** | DA** | CT** |
|---|---|---|---|---|---|---|---|---|---|
| 97-12B | 93 | 43 | 9 | 57 | 15 | nd | 34 | 61 | 47 |
| 89-25A | 71 | 13 | 70 | nd | 13 | nd | 15 | 43 | 30 |
| 94-359A | 50 | 18 | 3 | nd | 17 | 13 | 6 | 25 | 32 |
| 95-268B | 72 | 92 | 0 | 97 | 81 | nd | 0 | 45 | 68 |
| 97-15B2 | 91 | 72 | 53 | 65 | 55 | nd | 7 | 9 | 85 | nd = not determined
*WCIA(%) = {[(100 − FFW) + (% M) + (% IOC)] ÷ 300} × 100%.
**WCIP (%) = {[(100 − RW) + (100 − FFW) + (% M) + (% IOC)] ÷ 400} × 100%.

Therefore, the present invention is also directed to a bioherbicide comprising fungal isolates 85-24B, 94-26, 94-44B, 94-134, 95-54A1, 97-12B, 89-25A, 94-359A, 95-268B, 97-15B2, or a combination thereof, for the control of any susceptible weed, both annual and perennial. Preferably the weed is a broad leaf weed. More preferably, the broad leaf weed is from Compositae, Caryophyllaceae, Polygonaceae, Plantaginaceae, Rubiaceae, or Convolvulaceae, for example but not limited to, scentless chamomile, false cleavers, chickweed, wild buckwheat, field bindweed, perennial sow thistle, dandelion, and Canada thistle.

Using the inoculum mat bioassay (method outlined in Example 2), a number of fungal isolates were tested for their ability to control sunflower (*Helianthus*) weeds. Germination of seed was affected by fungal isolate 85-24B, which reduced sunflower seed germination by about 10%. Five fungal isolates (85-24B, 94-44B, 89-25A, 95-54A1, 97-15B2) reduced foliar biomass in prairie sunflower (see Table 13, Example 2). Thus, fungal isolates 85-24B, 94-44B, 89-25A, 95-54A1, 97-15B2 may be used to control prairie sunflower.

It has also been observed that these biocontrol agents and biocontrol compositions comprising the fungal isolates of the present invention are specific for a target group of weed plants, for example, those of the Aster (Compositae) family. Generally, the fungal isolates of the present invention were not effective in controlling growth of grasses, for example, wild oats, and green foxtail (see Table 15 and 16, respectively). However, 94-44B exhibits weed control activity in wild oats, and 85-24B and 95-359A exhibits weed control activity in green foxtail (see Table 21, Example 2 for summary of WCI's).

The fungal isolates of the present invention also exhibit selectivity in that, even under high inoculum loads (significantly higher than that used under field conditions), isolates can be identified that induce negligible, or no, disease symptoms in crop plants (see Tables 30A - 30D, Example 4). Example of crop plants tested include:

1) Cereal and other monocots

Wheat—cvs. Katepwa, AC Domain, AC Karma, Biggar, Kyle

Barley—cvs. Harrington, Silky

Oat—cvs. Derby or Walden

Millet—cvs. Minco or Prairie Gold

Canary seed—cv. Keet

2) Oilseed crops

Canola—cvs. AC Excel, AC Parkland

Mustard—cvs. Cutlas, Ochre

Flax—cv. Vimy

Sunflower—cvs. Cargill SF270 or IS7111

Safflower—cv. Lethbridge

3) Pulse crops

Lentil—cvs. Laird, Eston

Field pea—cv. Express

Chickpea—cv. Sanford

Faba bean—cv. CDC Fatima

4) Forage crops

Clovers—yellow clover cv. Norgold, white clover cvs. Polara and Sonja, common clover, red clover cvs. Altaswede or Florex Birdsfoot trefoil—cv. Cree Alfalfa—cv. Beaver For example, which is not to be considered limiting in any manner, 94-44B is suitable for use with cereal crops, as even under high inoculum loads no disease symptoms are observed. However, the use of 94-44B under high inoculum loads may not be desired for use on pulse crops, as pulse crops exhibit some disease symptoms under these conditions. If lower inoculum loads of 94-44B are used, then the disease symptoms in pulse are minimized and this fungal isolate may be used with pulse crops. At reduced inoculum loads, these isolates still exhibit weed control activity. One of skill in the art may manipulate the dosage to optimize the balance between obtaining weed control activity and avoiding disease symptoms in a non-target crop, agriculturally or commercially important plant.

Also contemplated by the present invention is the use of an inoculated broth, or an extract from one or more of the *Phoma macrostoma* isolates of the present invention as a weed control agent. As described in Example 5, an inoculated broth (including a concentrated inoculated broth), aqueous or solvent extracts, obtained from one or more *Phoma macrostoma* isolates as described herein, and reconstituted in an appropriate medium, for example, but not limited to water or methanol, may be applied to the soil or leaf of a plant and exhibit weed control activity. It is also contemplated that an inoculated broth, or an extract of the present invention may be combined with a chemical herbicide, or a fungal isolate, including non-*Phoma* isolates as a weed control agent.

Also contemplated by the present invention is a method using one or more than one *Phoma* cf *macrostoma* isolate, an extract therefrom, an inoculated broth therefrom, or a combination thereof for controlling weed development during growth of an establishing or established crop, for example, as listed above, and including, but not limited to a grass, such as, but not limited to domestic and specialty turf grasses, animal pasture or hay mixes comprising one or more of timothy, fescue, blue grass, perennial rye grass, bromegrass, canary grass, red top and orchard grass, as illustrated, for example, in Table 23 (Example 3).

The present invention further contemplates a method using one or more than one *Phoma* cf *macrostoma* isolate, an extract therefrom, an inoculated broth therefrom, or a combination thereof for enhancing the growth (e.g. increasing biomass) of an establishing or established crop, for example, as listed above, and including, but not limited to a grass, such as, but not limited to domestic and specialty turf grasses, animal pasture or hay mixes comprising one or more of timothy, fescue, blue grass, perennial rye grass, bromegrass, canary grass, red top and orchard grass, as illustrated, for example, in Tables 23 (Example 3), 28 and 29 (Example 3). Without wishing to be bound by theory, enhancement of growth may be a result of an increase in the rate of germination.

Also contemplated by the present invention is a method using one or more than one *Phoma* cf *macrostoma* isolate, an extract therefrom, an inoculated broth therefrom, or a combination thereof for controlling weed development during growth of an establishing or established crop by foliar spray application before or after emergence of the weed. The crop can be, for example, one of the crops listed above, and including, but not limited to a grass, such as, but not limited to domestic and specialty turf grasses, animal pasture or hay mixes comprising one or more of timothy, fescue, blue grass, perennial rye grass, bromegrass, canary grass, red top and orchard grass, as illustrated, for example in Table 29 (Example 3).

The application of an inoculated broth, or an extract of the present invention, when combined with an fungal isolate, exerts weed controlling activity in a rapid manner, when compared to applying an isolate on its own. Without wishing to be bound by theory, the inoculated broth, or extract is able to function in a more rapid manner, since there is no requirement for growth of the fungal isolate, and associated production of the one or more compounds from the growing fungal isolate prior to noting weed controlling activity. Such a combined application provides a rapid and more consistent weed controlling activity during the period of exposure of a plant to the extract-isolate, or inoculated broth-isolate mixture.

The present invention also contemplates the use of a fungal isolate or any combination of fungal isolates with one or more chemical herbicides. Further, the present invention contemplates biocontrol compositions comprising a fungal isolate of the present invention, or a plurality of fungal isolates with one or more chemical herbicides and a growth medium for supporting the viability of the fungal isolates. The present invention also encompasses the use of a fungal isolate or any combination of fungal isolates with one or more non-*Phoma* fungal strains. Further, the present invention contemplates biocontrol compositions comprising a fungal isolate of the present invention, or a plurality of non-*Phoma* fungal isolates with one or more herbicides and a growth medium for supporting the viability of the fungal isolates.

Also contemplated by the present invention is a probe for use in detecting one or more than one isolate of *Phoma macrostoma* that exhibits weed control activity. The probe may comprise SEQ. ID. NO: 1 (FIG. 9) or a fragment thereof or SEQ. ID. NO:15 (FIG. 19B) or a fragment thereof.

The probe may be prepared by digesting genomic DNA of fungal isolates of the present invention known to exhibit weed control activity, with restriction enzymes SacI and KpnI to create several 1-2 kb length fragments as set out in Example 6. The fragments were cloned into *E. coli* DH5α with the plasmid pBluescript KSII (Stratagene). Using Southern hybridization, one fragment from isolate 85-25B was found to bind to genomic DNA of 94-44B, 95-54A1, and 85-24B (see FIG. 7). This fragment was used as a probe for a Southern hybridization to chromosomal DNA from 7 other isolates of *P. macrostoma* that had demonstrated weed control activity (FIG. 8), plus one isolate of *P. medicaginis* and 3 isolates of *P. herbarum* to confirm that the isolated probe could be used to detect isolates that exhibit weed control activity. Plasmid DNA (pbluescript KSII containing the probe) was isolated using the QIAGEN® Spin Miniprep Kit. The probe (SacI-KpnI insert) was sequenced and the nucleotide sequence of the probe (SEQ. ID. NO: 1) is presented in FIG. 9.

The present invention also provides a method of detecting one or more than one isolate of *Phoma macrostoma* that exhibits weed control activity using the probe of the present invention. The method preferably comprises mixing nucleic acid from the one or more than one *Phoma macrostoma* isolate with a probe of the present invention under hybridization conditions, wherein hybridization of the nucleic acid from the one or more than one *Phoma macrostoma* isolate to the probe indicates that the isolate exhibits weed control activity. The nucleic acid of the *Phoma macrostoma* isolate is preferably genomic DNA. Non-limiting examples of a probe that may be used for this assay include SEQ ID NO:1, or a fragment thereof (FIGS. 9, 10), and SEQ ID NO15, or a fragment thereof (FIG. 19B).

The present invention also contemplates a primer pair for detecting one or more than one isolate of *Phoma macrostoma* that exhibits weed control activity. The primer pair may comprise SEQ. ID. NO: 2 and SEQ. ID. NO: 3 (FIG. 10). However, other primer pairs may be usd to amplify a region of the nucleotide sequence of SEQ ID NO: 1. Preferably, each primer of the primer pair is of about 13 to about 50 nucleotides in length. Furthermore, alternate primer pairs comprising for example but not limited to, nucleotides 40-60 and 450-470 of FIG. 19B may also be used. Additional primer pairs may be selected based upon the comparison of ITS sequences presented in FIG. 19A, so that regions of the ITS sequence that are unique to isolates exhibiting weed control activity are selected for use as primers for PCR or other methods that distinguish nucleic acid polymorphisms. Such regions include those residing within nucleotides 41-59, 340-350, 370-390, or 450-470 of FIG. 19A. As would be evident to one of skill in the art, other primer pairs may also be used to amplify a region of the nucleotide sequence of SEQ ID NO:1, or SEQ ID NO:15. Preferably, each primer of the primer pair is from about 13 to about 50 nucleotides in length, or any length therebetween.

The primer pair (SEQ. ID. NO: 2 and SEQ. ID. NO: 3) were designed based on the sequence of the probe (SEQ. ID. NO: 1). Additonal primer pairs may also be designed based on the nucleotide sequence of SEQ ID NO:1. Any of these primer pairs, for example, but not limited to a primer pair A, comprising nucleotides 541-561 and nucleotides 1240-1260 (of FIG. 10), primer pair B, comprising nucleotides 520-540 and nucleotides 1320-1340 (of FIG. 10), or any other primer pair of about 13-30 nucleotides in length selected from between nucleotide 1 and 1371 of FIG. 10, may be used to screen one or more fungal isolates to determine if the isolate exhibits weed control activity. For example, the primer pair may be used to amplify genomic DNA extracted from fungal isolates, by polymerase chain reaction (PCR) as set out in Example 6. The PCR products may be separated by electrophoresis and the presence of a DNA fragment produced using a primer pair comprising SEQ ID NO:2 and SEQ ID NO:3, that migrates between the 0.8 and 1.2 kb length markers, or a fragment of about 700 to about 1,200 base pairs in length or any amount therebetween, for example about 853 bps, indicates that the isolate exhibits weed control activity. An example of such an analysis is shown in FIG. 13. Similar amplification may be carried out using primer pairs derived from the ITS nucleotide sequence as shown in FIG. 19B (SEQ ID NO:15).

The present invention further provides a method of detecting one or more than one isolate of *Phoma macrostoma* that exhibits weed control activity using primer pairs derived from SEQ ID NO:1, for example but not limited to primer pairs defined by SEQ ID NO2 and SE ID NO:3. Alternate primer pairs may also be designed based on the nucleotide sequence of SEQ ID NO:1, for example, but not limited to a primer pair A, comprising nucleotides 541-561 and nucleotides 1240-1260 (of FIG. 10), primer pair B, comprising nucleotides 520-540 and nucleotides 1320-1340 (of FIG. 10), or any other primer pair of about 13-50 nucleotides in length selectred from between nucleotide 1 and 1371 of FIG. 10. The method preferably comprises amplifying nucleic acid from the one or more than one *Phoma macrostoma* isolate with a primer pair, wherein the presence of an amplified nucleic acid fragment indicates that the isolate exhibits weed control activity. The nucleic acid of the *Phoma macrostoma* isolate is preferably genomic DNA.

This invention pertains to the above method wherein genomic DNA from the one or more than one *Phoma macrostoma* isolate is amplified using Polymerase Chain Reaction (PCR), using a primer pair comprising SEQ ID NO:2 and SEQ ID NO:3 and the resulting PCR product(s) is separated by electrophoresis, wherein the presence of an amplified DNA fragment of between 0.8 and 1.2 kb, or a fragment of about 700 to about 1,200 base pairs in length or any amount therebetween, for example about 853 bps, indicates that the isolate exhibits weed control activity.

A method of screening one or more than one isolate of *Phoma macrostoma* using random amplified polymorphic DNA (RAPD) fingerprinting is given in Example 8. In this example, which is in not meant to be limiting in any way, the primers given in Table 37 were used to amplify DNA from a number of different *Phoma* isolates using PCR. The PCR products were resolved by electrophoresis. The DNA banding pattern for isolates known to exhibit weed control activity was found to be uniquely different from the banding pattern of other *Phoma* isolates and therefore RAPD fingerprinting provides a useful tool for screening *Phoma* isolates to determine if they exhibit weed control activity.

The present invention therefore contemplates a method of screening one or more than one isolate of *Phoma macrostoma* using random amplified polymorphic DNA (RAPD) fingerprinting to determine if the one or more than one isolate exhibits weed control activity, the method comprising:
 a) amplifying chromosomal DNA from the one or more than one *Phoma macrostoma* isolate known to exhibit weed control activity using a primer selected from the group consisting of SEQ. ID. NO: 4; SEQ. ID NO: 5; SEQ. ID.
NO: 6; SEQ. ID. NO: 7; and a combination thereof, to obtain a RAPD fragment pattern of the known isolate;
 b) repeating step (a) for chromosomal DNA from the one or more than one *Phoma macrostoma* isolate being screened, to obtain a RAPD fragment pattern of the isolate being screened;
 c) comparing the RAPD fragment pattern obtained in step (a) to the RAPD fragment pattern obtained in step (b), wherein similarities between the RAPD fragment patterns indicate that the one or more than one isolate of *Phoma macrostoma* being screened exhibits weed control activity.

A method of screening one or more than one isolate of *Phoma macrostoma* using amplified fragment length polymorphisms (AFLP) is given in Example 10. In this example, which is in not meant to be limiting in anyway, chromosomal DNA from *Phoma macrostoma* isolates is digested using restriction enzymes EcoRI and MseI, to obtain a plurality of DNA fragments. The DNA fragments are ligated using double stranded oligonucleotide EcoRI and MseI adaptors to the EcoRI and MseI restriction sites. The ligated fragments are then amplified by PCR using the primer pairs given in Table 38. The PCR products were separated by electrophoresis (see FIG. 21). The DNA banding pattern for isolates known to exhibit weed control activity was found to be uniquely different from the banding pattern of other *Phoma* isolates and therefore AFLP fingerprinting provides a useful tool for screening *Phoma* isolates to determine if they exhibit weed control activity.

The present invention therefore contemplates a method of screening one or more than one isolate of *Phoma macrostoma* using amplified fragment length polymorphisms (AFLP) fingerprinting to determine if the one or more than one isolate exhibits weed control activity. For example, which is not to be considered limiting, the method may comprise:
 a) digesting chromosomal DNA from one or more than one *Phoma macrostoma* isolate known to exhibit weed control activity using restriction enzymes EcoRI and MseI, to obtain a plurality of DNA fragments;
 b) ligating double stranded oligonucleotide EcoRI and MseI adaptors to the EcoRI and MseI restriction sites of the DNA fragments obtained in step (a);
 c) amplifying the ligated DNA fragments obtained in step (b) with a primer pair selected from the group consisting of:
  (i) SEQ. ID. NO: 10 and SEQ. ID. NO: 11;
  (ii) SEQ. ID. NO: 10 and SEQ. ID. NO: 12;
  (iii) SEQ. ID. NO: 13 and SEQ. ID. NO: 11;
  (iv) SEQ. ID. NO: 13 and SEQ. ID. NO: 12;
  (v) SEQ. ID. NO: 14 and SEQ. ID. NO: 11;
  (vi) SEQ. ID. NO: 14 and SEQ. ID. NO: 12; and
 a combination thereof; to obtain a set of amplified DNA fragments of the isolate;
 d) repeating steps (a) to (c) for chromosomal DNA from the one or more than one *Phoma macrostoma* isolate being screened, to obtain a set of amplified DNA fragments of the isolate;
 e) comparing the set of amplified DNA fragments obtained from the one or more than one *Phoma macrostoma* isolate known to exhibit weed control activity to the set of amplified DNA fragments obtained from the one or more than one *Phoma macrostoma* isolate being screened, wherein similarities between the amplified DNA fragments indicate that the one or more than one isolate of *Phoma macrostoma* being screened exhibits weed control activity.

However, other restriction enzyme—primer pair combinations may be used as described above to identify one or more than one isolate of *Phoma macrostoma* that exhibit weed control activity.

With reference to FIG. 21, a group of isolates comprising DAOM175940, SRC85-24B, SRC89-25A2, SRC94-26, SRC94-44B, SRC94-134, SRC94-359A, SRC95-54A1, SRC95-54A2 and SRC95-268B (corresponding to lanes 22, 44-46, 48-53) and that also include isolates SRC97-12B, SRC97-15B, SRC02-2A and SRC03-1A8 which are not shown on this gel but exhibit a similar band-profile, may be redially identified. These isolates exhibit a specific banding pattern as is evident from FIG. 21, furthermore, these isolates exhbit weed control actitviy. This analysis may be used to screen, select or identify one or more than one *Phoma macrostoma* isolate that exhibit weed control activity.

Therefore, the present invention also provides for a *phoma macrostoma* isolate characterized as having an amplified fragment length polymorphism (AFLP) as disclosed in FIG. 21, lanes 22, 44-46, and 48-53, obtaining using primer pairs
- (i) SEQ. ID. NO: 10 and SEQ. ID. NO: 11;
- (ii) SEQ. ID. NO: 10 and SEQ. ID. NO: 12;
- (iii) SEQ. ID. NO: 13 and SEQ. ID. NO: 11;
- (iv) SEQ. ID. NO: 13 and SEQ. ID. NO: 12;
- (v) SEQ. ID. NO: 14 and SEQ. ID. NO: 11;
- (vi) SEQ. ID. NO: 14 and SEQ. ID. NO: 12; and a combination thereof;

The present invention is also directed to *Phoma macrostoma* isolates that have been identified using the methods described above, including, RAPD, AFLP, PCR, or hybridization using the nucleotide sequence of SEQ ID NO:1 or a fragment thereof, or nucleotide sequence SEQ ID NO:15 or a fragment thereof, that exhbit weed control activity The present invention will be further illustrated in the following examples.

EXAMPLE 1

Isolation, Storage and Growth of Fungal Isolates

1.1 Fungal Isolates

Fungal strains were isolated from small chlorotic and necrotic lesions on leaf and stem tissues of Canada thistle plants collected from fields, pastures, and roadsides. Purified fungi isolated from the plant tissues were verified to cause the disease symptoms using Koch's postulates.

TABLE 4

Information on fungi isolated from Canada thistle

| Name | Location | Habitat | Host Growth Stage | Original symptoms |
|---|---|---|---|---|
| 85-24B | Erwood, SK | not recorded | flowering | leaf spots, chlorosis |
| 94-26 | Chatham, ON | roadside | vegetative | chlorosis |
| 94-44B | Melfort, SK | roadside | bolting | chlorosis |
| 94-134 | St. Quentin, NB | waste field | bolting | chlorosis |
| 95-54A1 | Coldbrook, NS | pasture | bolting, flowering | foliar necrosis |
| 97-12B | Valleyview, AB | fallow field | flowering | stem lesion |
| 89-25A | Ituna, SK | field crop | vegetative | leaf spots |
| 94-359A | RM 157, SK | barley field | seed setting | leaf spot, stem lesion |
| 95-268B | Rosthern, SK | filed crop | flowering | leaf spot |
| 97-15B2 | Westlock, AB | pasture | flowering | stem lesion, top dieback |

1.2 Isolation of Fungal Isolates

Fungal isolates, obtained as outlined above are surface sterilized for 2 minutes in 0.5% sodium hypochlorite, rinsed in sterile distilled water, and placed on Difco PDA (Potato Dextrose Agar) plates at 24° C. with 12 hours light, for 3-7 days. Fungi growing from the tissues are individually transferred to fresh media and allowed to grow to maturity. Isolates are screened for pathogenicity using Koch's postulates with a detached leaf bioassay. Freshly cut leaves from Canada thistle are surface sterilized and placed on a moist Whatman #3 filter paper in a glass petrie dish. An agar plug from the purified fungal culture is placed on the center of each leaf, the dish is sealed to prevent moisture loss, and incubated as described above. The development of disease symptoms is observed. Multiple copies of the purified pathogenic cultures are placed in cyropreservation storage as outlined below.

Purified fungal cultures are stored by cryopreservation of spores and mycelia at −78° C. using a 1:1 mixture of 10% skim milk (w/v) to 40% glycerol (v/v) solutions.

The following 10 fungal cultures were identified by CBS, The Netherlands as *Phoma macrostoma* Montagne, and were deposited within the International Deposit Authority of Canada (IDAC), Bureau of Microbiology, Health Canada, 1015 Arlington Street, Winnipeg, Manitoba, R3E 3R2 as follows:

85-24B (IDAC 230201-1, deposited Feb. 23, 2001);
89-25A (IDAC 110401-1, deposited Apr. 11, 2001);
94-26 (IDAC 230201-2, deposited Feb. 23, 2001);
94-44B (IDAC 230201-3, deposited Feb. 23, 2001);
94-134 (IDAC 230201-4, deposited Feb. 23, 2001);
94-359A (IDAC, 110401-2, deposited Apr. 11, 2001);
95-54A1 (IDAC 230201-5, deposited Feb. 23, 2001);
95-268B (IDAC, 110401-3, deposited Apr. 11, 2001);
97-12B (IDAC 230201-6, deposited Feb. 23, 2001); and
97-15B2 (IDAC, 110401-4, deposited Apr. 11, 2001).

1.3 Culturing and Storing Fungal Isolates

Flasks containing 125 mL of Potato Dextrose Broth (PDB) or V8® juice broth (Dhingra, O. D., and Sinclair, J. B. 1995. Basic Plant Pathology Methods, Second Edition, CRC Press Inc., Boca Raton, Fla.) were inoculated with $1 \times 10^5$ conida/L and incubated on a shaker (150 rpm) under ambient room conditions (20° C.) for a minimum of 7-14 days, but more preferably for 14-28 days. The contents of each flask are then vacuum filtered to separate spores and mycelium. Conidial concentration and fresh weight of mycelium are measured.

Fungi may be grown on solid or liquid media. For solid media culture, all fungal isolates are grown on Difco Potato Dextrose Agar (PDA; prepared as per manufacturer's directions) augmented with 3 ml 85% lactic acid per liter of media. A vial of fungal culture taken from cyropreservation is thawed to room temperature and the contents are aseptically distributed by pouring or pipetting the contents onto three or more prepared plates. The inoculum is spread over the surface of each plate using a sterile glass hockey stick. Agar plates are incubated either on a lab bench at ambient room temperature or in an incubator at 23/18° C. with 12 hours light (20 W cool white fluorescent bulbs) for one to two weeks.

For liquid media culture, 125 ml of Difco PDB is placed in a in a 500 ml Erlenmeyer. The flask is inoculated with either a spore suspension or agar plugs. For the spore suspension, an mature Difco PDA plate is flooded with sterile distilled water and the spores are gently dislodged with a sterile glass hockey stick. The spore suspension is diluted to a concentration of $1 \times 10^6$ spores/ml and then 1 ml of the diluted spore solution is added to each flask of liquid medium. To inoculate the liquid medium with agar plugs, 5-8 mm diameter agar plugs are taken from a mature culture on a Difco PDA plate. The inoculated flasks are incubated on a bench top shaker at 150 rpm for 2 weeks at ambient light and temperature conditions.

Mycelia (10 g) from the liquid cultures is placed in 20 mL of 5% skim milk: 20% glycerol cryo-preservation solution and homogenized. The samples are frozen and stored at −18° C. and −73° C. for 30 days and compared to a control prepared immediately after homogenization. Following storage for 30 days, viability is determined by spreading 500 L of the suspension on a plate of ½ strength PDA, incubating for 4 days, and assessing mycelial growth and conida production. As an example, there was no loss in viability of fungal isolate 85-24B grown in PDB or V8® juice broth after storage at −18° or −73° C. for a period of 1 month.

EXAMPLE 2

Control of Weed Growth Using Fungal Isolates 2.1 Effect of Dose on Weed Control

Fungal isolates are grown on PDA and lactic acid for 10 to 14 days. The agar plates cultured with fungus are weighed into doses of 50 g (equivalent to an entire agar plate), 10 g, 5 g, 2.5 g, and 0 g (control), then macerated with sterile distilled water and each dose of the inoculum suspension is brought to a final volume of 50 mL. As an example, 85-24B is tested.

Roots are cut into appropriate lengths, for example roots of Canada thistle are 10 cm long, weighed and placed in 10 cm square pots filled with soil. A dose of the inoculum suspension is poured over the surface of the roots, covered with 1 cm soil, watered to saturation and placed in a greenhouse (20° C. day, 15° C. night; 16 hr daylight) with 6 replicates. Plants are rated for shoot emergence, chlorosis and death at 2, 4, and 6 weeks. At 6 weeks, roots are harvested and weighed. Results from this study using isolate 85-24B are presented in FIG. 1 (the Rating scale is 1=healthy, dark green foliage; 2=slightly yellow-green foliage; 3=leaves primarily yellow, some yellow-green; 4=leaves primarily white, a few yellow-green; 5=plants completely white; and 6=plants dead).

These results demonstrate that fungal isolates of the present invention can control weed growth, and that this effect is more prominent with increased amounts of inoculum administered to the roots.

Inoculum Mat Bioassay

Roots are washed for 1 hour under running tap water to remove excess soil, and cut into 10 cm lengths each length with at least one bud. The weight of 2-10 cm root lengths, keeping similar root weights for all pots used in a replicate, is recorded A two week old inoculated agar plate is inverted over the root pieces. The control is an agar plate that was not inoculated with a fungus. The agar plate and roots are covered with 2-3 cm of soil mix, and the pots placed in a greenhouse at 20/15° C. and natural light. The total number of shoots or plants, number of shoots or plants that died, total number of shoots or plants with symptoms (i.e. chlorosis, necrosis, lesions) at 2, 4 and 6 weeks after root inoculation is recorded. After six weeks, foliar biomass and root weight were taken. Data analyzed for several parameters:

i) % root growth: [final root weight of treatment/start root weight of treatment]÷[final root weight of control/start root weight of control]×100);

ii) foliar biomass;

iii) shoot emergence as % of control; and iv) % shoots with symptoms.

2.2 Comparison of Fungal Isolates of the Present Invention to Other *Phoma macrostoma* Isolates Isolates of *Phoma macrostoma* were obtained from various world collections and compared to the isolates of the present invention for their ability to control weeds using the inoculum mat bioassay on dandelion. The isolates tested are given in Table 5

TABLE 5

Differential set of *Phoma macrostoma* isolates obtained from world collections.

| Isolate[a] | Genus/species | Host genus/species | Geographic origin and Canadian ecozone [ ][d] | Date of Isolation |
|---|---|---|---|---|
| ATCC24524 | Phoma macrostoma | Rubus idaeus | Germany | —[b] |
| ATCC46580 | Phoma macrostoma | Soil | Japan | 1981 |
| CBS112.36 | Phoma macrostoma var. incolorata | Fraxinus excelsior | Germany | 1936 |
| CBS115.12 | Phoma macrostoma var. macrostoma | Malus sylvestris | USA | 1912 |
| CBS154.83 | Phoma macrostoma var. macrostoma | Philadelphus coronarius | Baarn, The Netherlands | 1983 |
| CBS185.25 | Phoma macrostoma var. incolorata | Malus sylvestris | —[b] | 1925 |
| CBS198.69 | Phoma macrostoma var. macrostoma | Heracleum sphondylium | The Netherlands | 1969 |
| CBS223.69 | Phoma macrostoma var. incolorata | Acer pseudoplatanus | Brunnen, Switzerland | 1968 |
| CBS297.36 | Phoma macrostoma var. macrostoma | Rosa multiflora cv. cathayensis | Germany | 1926 |
| CBS300.36 | Phoma macrostoma var. incolorata | Robinia psuedo-acacia | Germany | 1936 |
| CBS345.97 | Phoma macrostoma | Ginkgo biloba | The Netherlands | 1997 |
| CBS371.61 | Phoma macrostoma var. macrostoma | Ulmus sp. | The Netherlands | 1961 |
| CBS482.95 | Phoma macrostoma var. macrostoma | Larix decidua | Munchen, Germany | 1995 |
| CBS483.66 | Phoma macrostoma var. incolorata | Syringa chinensis | Norway | 1966 |
| CBS488.94 | Phoma macrostoma var. macrostoma | Forsythia sp. | Baarn, The Netherlands | 1994 |
| CBS529.66 | Phoma macrostoma var. macrostoma | Malus sylvestris | Wageningen, The Netherlands | 1966 |
| CBS560.70 | Phoma macrostoma var. macrostoma | Hedera helix | The Netherlands | 1970 |
| CBS598.94 | Phoma macrostoma var. macrostoma | Sambucus nigra | The Netherlands | 1994 |
| CBS837.84 | Phoma macrostoma var. macrostoma | Triticum aestivum | Monheim, Germany | 1984 |
| CBS839.84 | Phoma macrostoma var. incolorata | Hordeum vulgare | Monheim, Germany | 1984 |
| CCM-F322 | Phoma macrostoma var. macrostoma | Viburnum carlesii | The Netherlands | 1969 |
| CCM-F323 | Phoma macrostoma var. incolorata | Trifolium pratense | The Netherlands | 1970 |
| DAOM175135 | Phoma macrostoma | Lens esculenta | Alberta, Canada [3] | 1979 |
| DAOM175940 | Phoma macrostoma | Cirsium arvense | Quebec, Canada [4] | 1979 |
| DAOM175951 | Phoma macrostoma | Ulmus sp. | Flevo Polder, The Netherlands | 1977 |
| ICMP2325 | Phoma macrostoma var. macrostoma | Malus X domestica | Levin, New Zealand | 1968 |
| ICMP2715 | Phoma macrostoma var. incolorata | Actinidia deliciosa | Te Puke, New Zealand | 1969 |
| ICMP3173 | Phoma macrostoma var. macrostoma | Prunus cerasus | The Netherlands | —[b] |
| ICMP6603 | Phoma macrostoma var. macrostoma | Actinidia deliciosa | Auckland, New Zealand | 1979 |
| ICMP6628 | Phoma macrostoma var. incolorata | Medicago sativa | Ruakura, New Zealand | 1977 |
| ICMP6803 | Phoma macrostoma var. macrostoma | Lolium perenne | Ruakura, New Zealand | 1979 |
| ICMP6814 | Phoma macrostoma var. incolorata | Lolium perenne | Ruakura, New Zealand | 1980 |

TABLE 5-continued

Differential set of *Phoma macrostoma* isolates obtained from world collections.

| Isolate[a] | Genus/species | Host genus/species | Geographic origin and Canadian ecozone [ ][d] | Date of Isolation |
|---|---|---|---|---|
| ICMP7033 | *Phoma macrostoma* var. *incolorata* | *Trifolium fragiferum* | Palmerston North, New Zealand | 1978 |
| ICMP10843 | *Phoma macrostoma* | *Prunus persica* | Levin, New Zealand | 1981 |
| ICMP10963 | *Phoma macrostoma* | *Lycopersicon esculentum* | Stratford, New Zealand | 1977 |
| ICMP11186 | *Phoma macrostoma* | *Narcissus* sp. | Kimbolton, New Zealand | 1977 |
| ICMP12948 | *Phoma macrostoma* | Rubber | New Zealand | —[b] |
| IMI118020 | *Phoma macrostoma* | *Malus pumila* | The Netherlands | 1966 |
| IMI175661 | *Phoma macrostoma* | *Rubus fruticosus* | UK | 1973 |
| IMI192267 | *Phoma macrostoma* | *Triticum* sp. | Ethiopia | 1975 |
| IMI192268 | *Phoma macrostoma* | *Triticale* | Ethiopia | 1975 |
| IMI299239 | *Phoma macrostoma* | *Humulus lupulus* | UK | 1986 |
| IMI336757 | *Phoma macrostoma* | *Acacia albida* | Tanzania | 1990 |
| IMI336761 | *Phoma macrostoma* | *Acacia lebbeck* | Tanzania | 1990 |
| MA1908B | *Phoma macrostoma* | rock surface | Vienna, Austria | 1999 |
| MA3312 | *Phoma macrostoma* | rock surface | Vienna, Austria | 1999 |
| SRC85-24B | *Phoma macrostoma* | *Cirsium arvense* | Saskatchewan, Canada [3] | 1985 |
| SRC89-25A2 | *Phoma macrostoma* | *Cirsium arvense* | Saskatchewan, Canada [3] | 1989 |
| SRC94-26 | *Phoma macrostoma* | *Cirsium arvense* | Ontario, Canada [4] | 1994 |
| SRC94-26Avir | *Phoma macrostoma* | *Cirsium arvense* | Not applicable [—[c]] | 1994 |
| SRC94-44B | *Phoma macrostoma* | *Cirsium arvense* | Saskatchewan, Canada [3] | 1994 |
| SRC94-134 | *Phoma macrostoma* | *Cirsium arvense* | New Brunswick, Canada [4] | 1994 |
| SRC94-359A | *Phoma macrostoma* | *Cirsium arvense* | Saskatchewan, Canada [3] | 1994 |
| SRC95-54A1 | *Phoma macrostoma* | *Cirsium arvense* | Nova Scotia, Canada [4] | 1995 |
| SRC95-54A2 | *Phoma macrostoma* | *Cirsium arvense* | Nova Scotia, Canada [4] | 1995 |
| SRC95-268B | *Phoma macrostoma* | *Cirsium arvense* | Saskatchewan, Canada [3] | 1995 |
| SRC97-12B | *Phoma macrostoma* | *Cirsium arvense* | Alberta, Canada [3] | 1997 |
| SRC97-15B2 | *Phoma macrostoma* | *Cirsium arvense* | Alberta, Canada [3] | 1997 |
| SRC02-2A | *Phoma macrostoma* | *Lens culinaris* | Saskatchewan, Canada [3] | 2002 |
| SRC03-1A8 | *Phoma macrostoma* | *Cirsium arvense* | Saskatchewan, Canada [3] | 2003 |
| WAC7788 | *Phoma macrostoma* | *Lupinus angustifolius* | Australia | 1972 |
| WAC7881 | *Phoma macrostoma* | *Rheum rhabarbarum* | Australia | 1976 |

Figure 6:
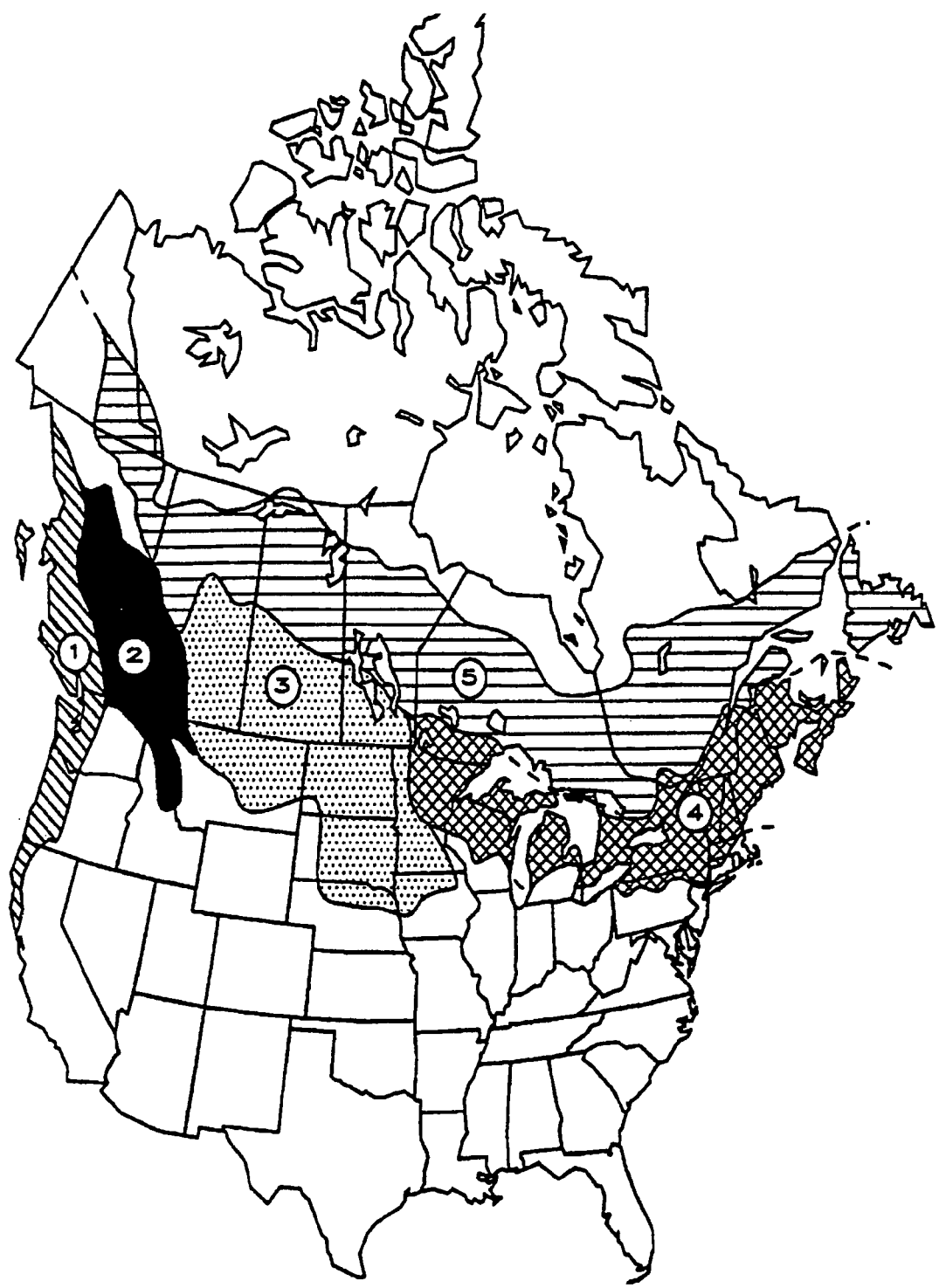
FIG. 6 shows the five microbial pesticide ecozones of Canada (Source: Pest Management Regulartory Agency, 2001).

[a]ATCC, American Type Culture Collection; CBS, Centraal Bureau voor Schimmelcultures; DAOM, Canadian Collection of Fungal Cultures (CCFC); CCM, Czech Collection of Microorganisms; ICMP, International Collection of Microorganisms from Plants; IMI, CABI Bioscience Genetic Resources Centre (formerly, International Mycological Institute (IMI)); WAC, Department of Agriculture Western Australia; MA isolates supplied by K. Sterflinger, University of Natural Resources and Applied Life Science, Vienna, Austria.
[b]unknown
[c]Avirulent isolate created in the laboratory (not isolated from nature).
[d]Canadian ecozones shown in FIG. 6

The effects of the *Phoma macrostoma* isolates on dandelion growth and development are shown in Table 6. The results show mean % weed reduction from 2 trials each with 5 replications. Mean % weed reduction and standard error of mean for the uninoculated agar control was 15.4%±3.7 S.E. and for the untreated control was 8.3%±1.6 S.E.

TABLE 6

Effect of root inoculation of Phoma isolates on disease development of dandelion using the inoculum mat bioassay. Isolates showing greater than 50% weed reduction have a high degree of bioherbicidal activity (in bold).

| Isolate | % weed reduction | Std. Error |
|---|---|---|
| SRC 94-44B | 99.5 | 0.5 |
| SRC 02-2A | 99.5 | 0.5 |
| SRC 95-268B | 95.5 | 1.5 |
| SRC 94-134 | 89.0 | 3.7 |
| SRC 94-359A | 89.0 | 4.2 |
| SRC 95-54A1 | 81.2 | 6.1 |
| SRC 94-26 | 76.1 | 7.7 |
| SRC 97-12B | 71.7 | 5.6 |
| SRC 85-24B | 68.2 | 5.7 |
| SRC 95-54A2 | 66.7 | 13.0 |
| DAOM 175940 | 59.9 | 11.8 |
| SRC 03-1A8 | 58.6 | 6.2 |
| SRC 89-25A2 | 57.6 | 5.8 |
| CBS 297-36 | 36.5 | 10.1 |
| ICMP 10963 | 31.6 | 9.7 |
| CBS 837.84 | 28.2 | 7.0 |
| CBS 483.66 | 23.1 | 7.8 |
| CBS 198.69 | 23.0 | 6.5 |
| CBS 223.69 | 22.1 | 9.1 |
| CBS 115.12 | 21.4 | 5.83 |
| DAOM 179750 | 20.2 | 6.2 |
| CBS 185.25 | 19.7 | 7.1 |
| CBS 482.95 | 19.6 | 5.4 |
| CBS 154.83 | 19.5 | 6.2 |
| ICMP 11186 | 19.5 | 5.3 |
| ICMP 3173 | 19.2 | 6.2 |
| IMI 118020 | 19.0 | 4.3 |
| IMI 192268 | 18.0 | 6.1 |
| CBS 839.84 | 17.7 | 6.5 |
| CBS 529.66 | 17.1 | 9.0 |
| ICMP 6628 | 16.5 | 4.3 |
| ICMP 7033 | 16.4 | 7.9 |
| IMI 175661 | 16.1 | 6.7 |
| MA 1908B | 16.1 | 4.1 |
| CBS 560.70 | 15.0 | 4.5 |
| IMI 336761 | 14.2 | 8.3 |
| CBS 371.61 | 13.8 | 5.5 |
| ICMP 6814 | 12.5 | 5.2 |
| WAC 7788 | 12.2 | 6.3 |

TABLE 6-continued

Effect of root inoculation of Phoma isolates on disease development of dandelion using the inoculum mat bioassay. Isolates showing greater than 50% weed reduction have a high degree of bioherbicidal activity (in bold).

| Isolate | % weed reduction | Std. Error |
|---|---|---|
| ATCC 24524 | 11.8 | 5.5 |
| CCMF 323 | 11.7 | 5.2 |
| CCMF 322 | 10.3 | 4.2 |
| IMI 299239 | 9.9 | 3.2 |
| CBS 598.94 | 9.8 | 2.9 |
| DAOM 175951 | 9.2 | 3.7 |
| ICMP 6803 | 8.7 | 3.5 |
| CBS 345.971 | 8.6 | 4.5 |
| ATCC 46580 | 8.5 | 3.4 |
| ICMP 2715 | 8.5 | 2.5 |
| WAC 7881 | 8.0 | 3.5 |
| ICMP 2325 | 7.9 | 5.0 |
| CBS 112-36 | 7.2 | 3.5 |
| MA 3312 | 6.8 | 4.0 |
| IMI 192267 | 6.6 | 4.5 |
| 94-26 Avir | 6.5 | 2.9 |
| CBS 488.94 | 6.3 | 3.4 |
| IMI 336757 | 6.3 | 2.8 |
| ICMP 6603 | 4.5 | 2.4 |
| ICMP 12948 | 4.1 | 1.9 |
| DAOM 175135 | 3.1 | 2.3 |
| CBS 300.36 | 0 | 0 |
| SRC 97-15B* | Not tested | Not tested |

*The culture of SRC 97-15B was found to be contaminated and a fresh culture was not retested.

Thirteen isolates demonstrated weed reductions greater than 50% (shown in bold in Table 6). The majority of isolates (48) showed little or no weed control activity with weed reductions less than 25% (Table 6). Isolates originating on Canada thistle (*Cirsium arvense*), including the isolates of the present invention, demonstrated weed control activity for dandelions. Also isolate SRC02-2A originating from *lens culinaris* demonstrated weed control activity (99.5% weed reduction) for dandelions. Isolate 97-15B has also weed control activity.

2.3 Effect of Fungal Isolates of the Present Invention on Canada Thistle Growth and Development The effects of several fungal isolates of the present invention on Canada thistle growth and development are shown in Table 7.

TABLE 7

Effect of root inoculation of *Phoma* isolates on disease development of Canada thistle, assayed using inoculum mat bioassay.

| | Root Zone Application | | |
|---|---|---|---|
| Isolate | Chlorosis (scale 1-6)$^z$ | Foliar fresh wt (g) | RW (% of control)* |
| Experiment A | | | |
| Control | 1 a$^y$ | 0.67 a | 100 a |
| 95-54A1 | 5 b | 0.24 b | 66 a |
| Experiment B | | | |
| Control | 1 a | 2.6 a | 100 a |
| 97-12B | 6 b | 0.0 b | 14 b |
| Experiment C | | | |
| Control | 1 a | 49.1 a | 100 a |
| 89-25A | 4 c | 17.0 c | 29 c |
| 94-359A | 1 a | 44.8 ab | 70 b |
| 97-15B2 | 3 b | 35.8 ab | 47 bc |

*RW - root weight;

$^z$Rating scale of increasing chlorosis starting from 1 = green, healthy to 6 = white, dead.

$^y$Different letters within a column for each experiment indicate significant differences at P < 0.05 using Duncan's Multiple Range Test.

The results in Table 7 demonstrate that the isolates were effective in weed control activity, for example controlling Canada thistle growth and development, when applied to soil.

2.4 Comparison of Fungal Strains for Canada Thistle Control

Using the inoculum mat bioassay, a range of fungal isolates were tested for weed control activity using Canada thistle as a weed.

The results using the above bioassay, on the effect of several fungal isolates on Canada thistle growth and development are shown in Table 8.

TABLE 8

Comparison of fungal isolates and untreated control for reduction in root weight, foliar biomass, mortality, and expression of disease symptoms in Canada thistle conducted in six greenhouse experiments.

| | Control | 85-24B | 94-26 | 94-44B | 94-134 | 95-54A1 | 97-12B | 89-25A | 95-359A | 95-268B | 97-15B2 |
|---|---|---|---|---|---|---|---|---|---|---|---|
| | Root weight (% of control) | | | | | | | | | | |
| Expt 1 | 100a* | 41 b | 84 a | 18 b | nt** | nt | 68 ab | 73 a | 85 a | 51 ab | nt |
| Expt 2 | 100 a | 33 cd | 8 d | 11 d | nt | nt | 53 bc | 34 cd | 28 cd | 46 c | nt |
| Expt 3 | 100 a | 23 b | 19 b | 16 b | nt | nt | 37 b | 83 a | 77 a | 23 b | nt |
| Expt 4 | 100 a | 6 b | 10 b | 12 b | 28 b | 8 b | nt | nt | nt | 17 b | 14 b |
| Expt 5 | 100 a | 30 b | 24 b | 26 b | 32 b | 16 b | nt | nt | nt | 42 b | 20 b |
| Expt 6 | 100 a | 13 c | 12 c | 9 c | 17 c | 46 b | nt | nt | nt | 14 c | 17 c |
| Mean ± SE | ±100 ± 5 | 25 ± 4 | 26 ± 6 | 15 ± 2 | 26 ± 5 | 23 ± 8 | 53 ± 11 | 63 ± 11 | 63 ± 10 | 32 ± 6 | 17 ± 4 |
| | Foliar fresh wt (g) | | | | | | | | | | |
| Expt 1 | 5.2 ab | 2.2 c | 5.3 ab | 0.5 d | nt | nt | 4.7 ab | 4.1 b | 4.8 ab | 2.4 c | nt |
| Expt 2 | 4.1 a | 1.4 cde | 0.2 e | 0.1 e | nt | nt | 2.4 bc | 1.7 cde | 0.8 de | 1.8 cd | nt |
| Expt 3 | 3.0 a | 1.1 b | 0.4 b | 0.1 b | nt | nt | 0.9 b | 3.2 a | 2.8 a | 0.6 b | nt |

TABLE 8-continued

Comparison of fungal isolates and untreated control for reduction in root weight, foliar biomass, mortality, and expression of disease symptoms in Canada thistle conducted in six greenhouse experiments.

|  | Control | 85-24B | 94-26 | 94-44B | 94-134 | 95-54A1 | 97-12B | 89-25A | 95-359A | 95-268B | 97-15B2 |
|---|---|---|---|---|---|---|---|---|---|---|---|
| Expt 4 | 11.8 a | 0 c | 0 c | 0 c | 4.4 b | 0.2 c | nt | nt | nt | 2.3 bc | 1.4 bc |
| Expt 5 | 8.6 a | 0.7 b | 0.8 b | 2.4 b | 1.6 b | 0.3 b | nt | nt | nt | 3.5 b | 1.1 b |
| Expt 6 | 11.1 a | 0.5 c | 0.8 c | 0.7 c | 0.4 c | 5.9 b | nt | nt | nt | 1.8 c | 1.7 c |
| Mean ± SE | 7.2 ± 0.5 | 1.0 ± 0.2 | 1.3 ± 0.4 | 0.6 ± 0.3 | 2.1 ± 0.9 | 2.2 ± 1.1 | 2.7 ± 0.6 | 3.0 ± 0.5 | 2.8 ± 0.6 | 2.0 ± 0.6 | 1.4 ± 0.7 |
| | | | | | Mortality (%) | | | | | | |
| Expt 1 | 0 | 20 bc | 0 | 38 c | nt | nt | 7 ab | 8 ab | 10 ab | 27 bc | nt |
| Expt 2 | 5 a | 40 b | 95 c | 100 c | nt | nt | 39 b | 50 b | 45 b | 27 ab | nt |
| Expt 3 | 0 | 40 b | 78 c | 85 c | nt | nt | 39 b | 50 b | 45 b | 27 ab | nt |
| Expt 4 | 0 | 92 bc | 100 c | 100 c | 60 b | 92 bc | nt | nt | nt | 88 c | 87 bc |
| Expt 5 | 0 | 72 d | 78 d | 78 d | 40 bc | 90 d | nt | nt | nt | 64 cd | 73 d |
| Expt 6 | 2 a | 84 c | 82 c | 90 c | 77 c | 55 bc | nt | nt | nt | 80 c | 83 c |
| Mean ± SE | 1 ± 1 | 57 ± 7 | 72 ± 7 | 80 ± 5 | 59 ± 11 | 79 ± 8 | 39 ± 11 | 23 ± 8 | 18 ± 9 | 58 ± 8 | 81 ± 8 |
| | | | | Disease Symptoms (% shoots with chlorosis) | | | | | | | |
| Expt 1 | 0 | 87 b | 23 a | 100 b | nt | nt | 33 a | 32 a | 20 a | 70 b | nt |
| Expt 2 | 0 | 80 bc | 95 c | 100 c | nt | nt | 70 bc | 50 b | 100 c | 63 b | nt |
| Expt 3 | 0 | 67 b | 90 bc | 100 c | nt | nt | 80 bc | 25 a | 10 a | 85 bc | nt |
| Expt 4 | 0 | 100 c | 100 c | 100 c | 60 b | 96 c | nt | nt | nt | 88 c | 87 c |
| Expt 5 | 0 | 100 c | 88 bc | 78 bc | 73 bc | 100 c | nt | nt | nt | 68 b | 90 bc |
| Expt 6 | 0 | 88 c | 100 c | 100 c | 90 c | 49 b | nt | nt | nt | 80 c | 90 c |
| Mean ± SE | 0 ± 0 | 86 ± 6 | 83 ± 6 | 96 ± 2 | 74 ± 9 | 82 ± 8 | 61 ± 11 | 36 ± 10 | 43 ± 13 | 75 ± 7 | 89 ± 6 |

*For each experiment, different letters in a row indicate significant differences among the isolates and the control by Duncan's multiple range test at P < 0.1.
**nt—not tested.

These results demonstrate that a range of *Phoma* isolates have a negative impact on root weight, foliar fresh weight, chlorosis, and mortality in Canada thistle, and may be used to control the growth and development of Canada thistle.

The above results were averaged (Table 9). These results indicate that a range of fungal isolates exhibit weed control activity, in that the WCIP is greater than 20%.

TABLE 9

Comparison of 10 fungal strains for control of Canada thistle using the inoculum mat bioassay. Means and standard error calculated from data collected in 3-6 trials, each trial with 5 replicates.

| Treatment | RW* % of control | FFW % of control | Mortality % | IOC % | WCIP % |
|---|---|---|---|---|---|
| Control | 100 ± 5 | 100 ± 4 | 1 ± 1 | 0 ± 0 | 0 |
| 85-24B | 25 ± 4 | 22 ± 6 | 57 ± 7 | 86 ± 6 | 74 |
| 94-26 | 26 ± 6 | 23 ± 7 | 72 ± 7 | 83 ± 6 | 76 |
| 94-44B | 15 ± 2 | 8 ± 3 | 80 ± 5 | 96 ± 2 | 88 |
| 94-134 | 26 ± 5 | 20 ± 8 | 59 ± 11 | 74 ± 9 | 72 |
| 95-54A1 | 23 ± 8 | 20 ± 10 | 79 ± 8 | 82 ± 8 | 79 |
| 97-12B | 53 ± 11 | 59 ± 13 | 39 ± 11 | 61 ± 11 | 47 |
| 89-25A | 63 ± 11 | 76 ± 13 | 23 ± 8 | 36 ± 10 | 30 |
| 94-359A | 63 ± 10 | 69 ± 13 | 18 ± 9 | 43 ± 13 | 32 |
| 95-268B | 32 ± 6 | 31 ± 7 | 58 ± 8 | 75 ± 7 | 68 |
| 97-15B2 | 17 ± 4 | 13 ± 6 | 81 ± 8 | 89 ± 6 | 85 |

*RW—root weight; FFW—foliar fresh weight; IOC—incidence of chlorosis; WCIP—weed control index perennial (WCIP % = {[(100 − root weight) + (100 − foliar fresh weight) + (% mortality) + (% incidence of chlorosis)] ÷ 400} × 100%.)

2.5 Comparison of Weed Control Activity of Fungal Strains in a Range of Plants

The weed control activity of a range of fungal isolates on several annual and perennial weeds and other plants is examined using the mat bioassay. The plants tested are:
Perennial sow thistle Table 10
Dandelion Table 11
Scentless chamomile Table 12
Prairie Sunflower Table 13
False Cleavers Table 14
Wild Oats Table 15
Green Foxtail Table 16
Chickweed Table 17
Wild Buckwheat Table 18
Field Bindweed Table 19
Plantain Table 20
Summary of WCI's Table 21

In Tables 10-21, the following acronyms are used:
RW—root weight;
FFW—foliar fresh weight;
IOC—incidence of chlorosis;
WCIP—weed control index perennial (WCIP %={[(100—root weight)+(100—foliar fresh weight)+(% mortality)+(% incidence of chlorosis)]÷400}×100%.)
WCIA—weed control index annual (WCIA %={[(100—foliar fresh weight)+(% mortality)+(% incidence of chlorosis)]÷×300}×100%.) Pooled S.E.=Mean pooled standard error among isolates and control

TABLE 10

Comparison of fungal strains for control of perennial sow thistle.

| Isolate | RW (% of C) | FFW (% of C) | Mortality % | IOC % | WCIP % |
|---|---|---|---|---|---|
| Control (C) | 100 | 100 | 3 | 0 | 0.1 |
| 85-24B | 78 | 100 | 7 | 0 | 7 |
| 94-26 | 67 | 72 | 0 | 33 | 24 |
| 94-44B | 22 | 20 | 33 | 40 | 58 |
| 94-134 | 68 | 100 | 0 | 0 | 8 |
| 95-54A1 | 67 | 100 | 10 | 10 | 13 |
| 97-12B | 57 | 76 | 27 | 40 | 34 |
| 89-25A | 92 | 87 | 20 | 17 | 15 |
| 94-359A | 100 | 98 | 13 | 13 | 6 |
| 95-268B | 100 | 100 | 0 | 0 | 0 |
| 97-15B2 | 72 | 100 | 0 | 0 | 7 |
| Pooled S.E. | 12 | 14 | 4 | 6 | |

TABLE 11

Comparison of fungal strains for control of dandelion.

| Isolate | RW (% of C) | FFW (% of C) | Mortality % | IOC % | WCIP % |
|---|---|---|---|---|---|
| Control (C) | 100 | 100 | 0 | 0 | 0 |
| 85-24B | 55 | 17 | 19 | 100 | 62 |
| 94-26 | 63 | 50 | 12 | 90 | 47 |
| 94-44B | 63 | 24 | 24 | 97 | 59 |
| 94-134 | 88 | 80 | 7 | 21 | 15 |
| 95-54A1 | 47 | 35 | 45 | 80 | 61 |
| 97-12B | 48 | 21 | 35 | 78 | 61 |
| 89-25A | 70 | 31 | 13 | 74 | 43 |
| 94-359A | 73 | 66 | 15 | 38 | 25 |
| 95-268B | 57 | 37 | 10 | 75 | 45 |
| 97-15B2 | 79 | 96 | 4 | 12 | 9 |
| Pooled S.E. | 8 | 13 | 6 | 8 | |

TABLE 12

Comparison of fungal strains for control of scentless chamomile.

| Isolate | FFW (% of C) | Mortality % | IOC % | WCIA % |
|---|---|---|---|---|
| Control (C) | 100 | 12 | 8 | 7 |
| 85-24B | 28 | 83 | 83 | 79 |
| 94-26 | 66 | 27 | 19 | 27 |
| 94-44B | 15 | 86 | 75 | 82 |
| 94-134 | 16 | 83 | 80 | 82 |
| 95-54A1 | 0 | 100 | 94 | 98 |
| 97-12B | 5 | 93 | 91 | 93 |
| 89-25A | 26 | 81 | 60 | 71 |
| 94-359A | 45 | 49 | 46 | 50 |
| 95-268B | 18 | 67 | 67 | 72 |
| 97-15B2 | 14 | 91 | 95 | 91 |
| Pooled S.E. | 15 | 15 | 14 | |

TABLE 13

Comparison of fungal strains for control of Prairie Sunflower.

| Isolate | FFW (% of C) | Mortality % | IOC % | WCIA % |
|---|---|---|---|---|
| Control (C) | 100 | 0 | 0 | o |
| 85-24B | 19 | 85 | 88 | 84 |
| 94-26 | nd | 2 | 0 | nd |
| 94-44B | 32 | 65 | 74 | 69 |
| 94-134 | 85 | 0 | 4 | 6 |
| 95-54A1 | 21 | 51 | 86 | 72 |
| 97-12B | 100 | 11 | 15 | 9 |
| 89-25A | 27 | 62 | 75 | 70 |
| 94-359A | 100 | 0 | 8 | 3 |
| 95-268B | 100 | 0 | 0 | 0 |
| 97-15B2 | 44 | 60 | 44 | 53 |
| Pooled S.E. | 15 | 10 | 10 | |

TABLE 14

Comparison of fungal strains for control of false cleavers.

| Isolate | FFW (% of C) | Mortality % | IOC % | WCIA % |
|---|---|---|---|---|
| Control (C) | 100 | 12 | 0 | 4 |
| 85-24B | 66 | 33 | 24 | 30 |
| 94-26 | 43 | 45 | 42 | 48 |
| 94-44B | 35 | 65 | 63 | 64 |
| 94-134 | 42 | 63 | 40 | 54 |
| 95-54A1 | 41 | 78 | 76 | 71 |
| 97-12B | 48 | 45 | 31 | 43 |
| 89-25A | 97 | 23 | 13 | 13 |
| 94-359A | 90 | 29 | 14 | 18 |
| 95-268B | 6 | 93 | 89 | 92 |
| 97-15B2 | 29 | 72 | 74 | 72 |
| Pooled S.E. | 16 | 10 | 11 | |

TABLE 15

Comparison of fungal strains for control of wild oats.

| Isolate | FFW (% of C) | Mortality % | IOC % | WCIA % |
|---|---|---|---|---|
| Control (C) | 100 | 0 | 0 | 0 |
| 85-24B | 100 | 0 | 0 | 0 |
| 94-26 | na | 4 | 0 | nd |
| 94-44B | 100 | 3 | 61 | 21 |
| 94-134 | 94 | 0 | 0 | 2 |
| 95-54A1 | 100 | 0 | 0 | 0 |
| 97-12B | 100 | 0 | 0 | 0 |
| 89-25A | 100 | 0 | 0 | 0 |
| 94-359A | 100 | 0 | 0 | 0 |
| 95-268B | 96 | 13 | 0 | 17 |
| 97-15B2 | 96 | 0 | 0 | 4 |
| Pooled S.E. | 18 | 1 | 1 | |

TABLE 16

Comparison of fungal strains for control of green foxtail.

| Isolate | FFW (% of C) | Mortality % | IOC % | WCIA % |
|---|---|---|---|---|
| Control (C) | 100 | 3 | 0 | 1 |
| 85-24B | 48 | 37 | 39 | 43 |
| 94-26 | na | 52 | 0 | nd |
| 94-44B | 72 | 0 | 3 | 10 |
| 94-134 | 100 | 0 | 0 | 0 |
| 95-54A1 | 100 | 6 | 0 | 2 |
| 97-12B | 95 | 18 | 0 | 8 |
| 89-25A | 100 | 3 | 0 | 3 |
| 94-359A | 50 | 36 | 43 | 43 |
| 95-268B | 100 | 0 | 0 | 0 |
| 97-15B2 | 100 | 0 | 0 | 0 |
| Pooled S.E. | 20 | 4 | 2 | |

TABLE 17

Effect of fungal isolates on control of chickweed.

| | Emergence % | Chlorosis % | FFW % | Mortality % | WCIA % |
|---|---|---|---|---|---|
| Control (C) | 57 | 0 | 100 | 3 | 0 |
| 85-24B | 55 | 73 | 15 | 70 | 76 |
| 94-134[Z] | 65 | 34 | 29 | 70 | 91 |
| 94-26 | 45 | 87 | 1 | 88 | 99 |
| 94-44B | 35 | 100 | 0 | 96 | 59 |
| 95-54A1 | 60 | 3 | 3 | 82 | 84 |
| 97-12B | 36 | 50 | 18 | 40 | 57 |

TABLE 17-continued

Effect of fungal isolates on control of chickweed.

| | Emergence % | Chlorosis % | FFW % | Mortality % | WCIA % |
|---|---|---|---|---|---|
| 95-268B | 69 | 97 | 2 | 97 | 97 |
| 97-15B2 | 64 | 60 | 22 | 56 | 65 |

[Z]Mean of two trials

TABLE 18

Effect of fungal isolates on control of wild buckwheat.

| | Emergence % | Chlorosis % | FFW % | Mortality % | WCIA % |
|---|---|---|---|---|---|
| Control (C) | 54 | 0 | 100 | 0 | 0 |
| 85-24B | 41 | 88 | 1 | 91 | 92 |
| 94-134 | 32 | 87 | 5 | 74 | 39 |
| 94-26 | 40 | 22 | 32 | 28 | 96 |
| 94-44B | 49 | 95 | 1 | 95 | 85 |
| 95-54A1 | 55 | 5 | 78 | 5 | 11 |
| 97-12B | 40 | 4 | 61 | 0 | 15 |
| 89-25A | 39 | 0 | 62 | 0 | 13 |
| 94-359A | 41 | 0 | 49 | 0 | 17 |
| 95-268B | 36 | 89 | 7 | 59 | 81 |
| 97-15B2 | 40 | 63 | 22 | 25 | 55 |

TABLE 19

Effect of fungal isolates on control of field bindweed.

| | Emergence % | Chlorosis % | FFW % | Mortality % | WCIA % |
|---|---|---|---|---|---|
| Control (C) | 34 | 0 | 100 | 9 | 3 |
| 95-54A1 | 33 | 50 | 32 | 43 | 54 |
| 94-359A | 37 | 0 | 75 | 13 | 13 |

TABLE 20

Effect of fungal isolates on control of plantain (*Plantago lanceolata*).

| | % Emergence | % Chlorosis | % Fresh weight index % | % Mortality | Weed control |
|---|---|---|---|---|---|
| No fungus | 100 | 0 | 100 | 0 | 0 |
| 85-24B | 91 | 98 | 0 | 100 | 100 |
| 94-134 | 96 | 100 | 0 | 98 | 98 |
| 94-26 | 100 | 100 | 0 | 100 | 100 |
| 94-44B | 100 | 100 | 0 | 100 | 100 |
| 95-54A1 | 100 | 100 | 0 | 100 | 100 |
| 97-15B2 | 95 | 25 | 44 | 26 | 36 |

Annual weed control index % = [(100 − foliar fresh weight) + (% mortality) + (% incidence of chlorosis)] ÷ 300 × 100%. A weed control index greater than 25% was considered to be acceptable.

TABLE 21

Weed control index (WCI) of fungal isolates on scentless chamomile, false cleavers, wild oats, green foxtail, chickweed, wild buckwheat, field bindweed, plantain, perennial sow thistle, dandelion, and Canada thistle. A weed control index greater than 25% was considered to be acceptable.

| | Weed control index % | | | | | | | | | | | Summary of Bioactivity Levels | |
|---|---|---|---|---|---|---|---|---|---|---|---|---|---|
| | | | | | | | | | | | | Preferred WCI: 50-75% | Most preferred WCI: 75-100% |
| Isolate | SC | FC | WO | GF | CH | WB | FB | PL | PST | DA | CT | | |
| No fungus | 7 | 4 | 0 | 1 | 0 | 0 | 3 | 0 | 0.1 | 0 | 0 | na | na |
| 85-24B | 79 | 30 | 0 | 43 | 76 | 92 | nd | 100 | 7 | 62 | 74 | DA, CT | SC, CH, WB, PL |
| 94-26 | 27 | 48 | nd | nd | 91 | 39 | nd | 100 | 24 | 47 | 76 | none | CH, CT, PL |
| 94-44B | 82 | 64 | 21 | 10 | 99 | 96 | nd | 100 | 58 | 59 | 88 | FC, PST, DA | SC, CH, WB, CT, PL |
| 94-134 | 82 | 54 | 2 | 0 | 59 | 85 | nd | 98 | 8 | 15 | 72 | FC, CH, CT | SC, WB, PL |
| 95-54A1 | 98 | 71 | 0 | 2 | 84 | 11 | 54 | 100 | 13 | 61 | 79 | FC, FB, DA | SC, CH, CT, PL |
| 97-12B | 93 | 43 | 0 | 8 | 57 | 15 | nd | nd | 34 | 61 | 47 | CH, DA | SC |
| 89-25A | 71 | 13 | 0 | 3 | nd | 13 | nd | nd | 15 | 43 | 30 | SC | none |
| 94-359A | 50 | 18 | 0 | 43 | nd | 17 | 13 | nd | 6 | 25 | 32 | SC | none |
| 95-268B | 72 | 92 | 17 | 0 | 97 | 81 | nd | nd | 0 | 45 | 68 | SC, CT | FC, CH, WB |
| 97-15B2 | 91 | 72 | 4 | 0 | 65 | 55 | nd | 36 | 7 | 9 | 85 | FC, CH, WB, SF | SC, CT | nd = no data;
na = not applicable
Annual weeds:
SC = scentless chamomile,
WO = wild oats,
GF = green foxtail,
FC = false cleavers,
CH = chickweed,
WB = wild buckwheat,
FB = field bindweed,
PL = plantain seed
Annual weed control index % = [(100 − foliar fresh weight) + (% mortality) + (% incidence of chlorosis)] ÷ 300 × 100%
Perennial weeds:
PST = perennial sow thistle,
DA = dandelion,
CT = Canada thistle
Perennial weed control index % = [(100 − root weight) + (100 − foliar fresh weigh) + (% mortality) + (% incidence of chlorosis)} ÷ 400 × 100%

Collectively these results demonstrate that a range of *Phoma macrostoma* isolates are effective at selectively controlling weed growth. These isolates are effective at controlling weed growth of broadleaf weeds, including the Plantaginaceae, for example, plantain, the Compositae, for example scentless chamomile, dandelion, perennial sow thistle, false cleavers, and Canada thistle, Caryophyllaceae, for example chickweed, Polygonaceae, for example field bindweed, Convolvulacease, for example field bindweed. *Phoma macrostoma* does not exhibit weed control activity of grassy weeds, for example wild oats, and green foxtail, and can therefore be used to control broad leaf weeds in grasses.

EXAMPLE 3

Characterization of Weed Control Activity

Hulless Barley Bioassay

To prepare the barley for inoculation with a fungal isolate, hulless barley, for example but not limited to, barley cv. CDC Silky was soaked in distilled water. Excess water was drained and the barley was autoclaved for 45 minutes at 121° C. for a total of three times. After autoclaving the flasks were inoculated when cool.

To prepare the inoculum suspension, a two-week old agar culture plate was placed in a wide mouth bottle with sterile distilled water, and an antibiotic stock solution (streptomycin and vancomycin) was added and the agar antibiotic mixture was homogenized.

Each container of sterile barley grains was inoculated with the homogenized inoculum suspension and incubated for two weeks under ambient lab conditions. After incubation, barley from the container was removed and the infected grains were spread in a thin layer over the tray to dry for 4 days under ambient room conditions. The dry grains were ground with a mill (i.e. Arthur H. Thomas Co.). The ground inoculum may be stored for up to 3 months at room temperature or refrigerated for longer storage time. The control consisted of uninoculated sterile grain treated in the same manner. Viability of ground inoculum was determined by plating 25 pieces on PDA plate and recording the number of particles with colony growth after 3 days and the number of colonies that resemble the original fungal isolate or are contaminants after 7 days.

To conduct the bioassay, healthy roots were cut into 10 cm long segments, making sure that each root segment has at least one bud. Washed root segments were weighed and placed two per pot. Ground inoculum was sprinkled evenly over roots and soil surface, for example about 5 g (other doses may also be used), covered with 2-3 cm of soil mix, and the pots were placed in a greenhouse. The total number of shoots, number of shoots or plants that died, total number of shoots or plants with symptoms (i.e. chlorosis, necrosis, lesions) at 2, 4 and 6 weeks after root inoculation was recorded. Also at 6 weeks collect, the fresh weight of rinsed roots remaining in pot and the fresh weight of foliar tissue was recorded. Data was analyzed for several parameters:

i) % root growth (i.e.[final root weight of treatment/start root weight of treatment]÷[final root weight of control/start root weight of control]×100);
ii) foliar biomass;
iii) shoot emergence as % of control; and
iv) % shoots with symptoms.

3.1 Duration of Application

To determine the efficacy of a single application of fungal isolates of the present invention over subsequent years, sample fungal isolates were applied to the soil (hulless barley inoculum prepared as outlined above) at a rate of 1 kg/m$^2$ (over a range of particle sizes from 50-840 µ; see Table 25 below ), at three different periods within the growth season: late spring (at the time of emergence of Canada thistle); mid summer; and in the fall. The number of Canada thistle remaining in the test plots were determined over two growth seasons. The results of this experiment are presented in Table 22.

TABLE 22

The effect of a single application of isolate 85-24B to the soil on the emergence of Canada thistle plants in the field.

| | Number of Canada thistle plants per plot over time | | | | |
|---|---|---|---|---|---|
| Treatment | August '99 | September '99 | May '00 | June '00 | July '00 |
| Control | 45 ± 9 | 80 ± 12 | 43 ± 5 | 69 ± 6 | 114 ± 5 |
| Applied June 1999 | 21 ± 1 | 44 ± 2 | 20 ± 2 | 42 ± 4 | 73 ± 4 |
| Applied August 1999 | 14 ± 5 | 39 ± 17 | 22 ± 6 | 41 ± 9 | 80 ± 14 |
| Applied October 1999 | na | Na | 46 ± 9 | 82 ± 15 | 131 ± 21 | na = not available

These data illustrate that a single application of a fungal isolate of the present invention is effective at exerting weed control activity over one or more growth seasons. The weed control activity is greatest if the inoculum is applied in the spring or summer, and is reduced if applied in the fall.

3.2 Weed Control Activity in Lawns

To determine the efficacy of a single application of fungal isolates of the present invention for weed control in the establishment of lawn from seed or in previously established perennial turf, sample fungal isolates were applied in the spring to the soil (hulless barley inoculum prepared as outlined above) at a rate between 250-1000 g/m$^2$ (over a range of particle sizes from 50-840 µ; see Table 25 below). Inoculum, grass seed and weed seed were weighed out prior to setting up the field plots. A turf grass "Overseeding" mixture was applied at 5.7 g per ¼ m$^2$ (200 lb per acre). It contained 40% Perennial Rye (Manhattan III and Calypso II), 25% Kentucky Blue Grass (Quantum Leap and Alene), 15% Chewings Fescue, 10% Creeping Red Fescue, 10% *Poa trivialis* L. From this amount a 10% weed mix was calculated (5% dandelion seed and 5% chickweed seed) to be 0.6 g per ¼ m$^2$. Inoculum isolates were weighed according to the dose applied. Field plot preparation of the seeded grass area consisted of rototilling the soil and then firmly packing the seedbed by stepping on a m$^2$ piece of plywood. Areas that were not smooth, were raked and packed again. The ¼ m$^2$ plots were set up in the centre of the packed area. The grass seed, weed seed and inoculum were sprinkled on top and hand raked in two directions. Then 5 m lengths of row cover were placed on top of the plots for a 2 week period and in this time, the plots were watered everyday, just enough to keep the surface moist and not to let the grass seed dry out while germinating. In previously established turf, the ¼ m$^2$ plots were set up in an area where grass had been growing for more than 20 years. Weed seed and the inoculum were sprinkled on the surface and hand raked in two directions. The plots were watered daily for 2 weeks enough to keep the surface moist, but not enough for the inoculum to run off with the water. The number of dandelion and chickweed plants in the test plots were determined over the growing season. Biomass was measured as fresh weight in grams of the grass. The results of this experiment are presented in Table 23.

TABLE 23

Effect of a single application of 85-24B to the soil on the mean emergence of dandelion and chickweed in turf.

| Lawn Treatment | Rate of Application g/m$^2$ | Number of weeds per plot | | Biomass Fr wt. g |
|---|---|---|---|---|
| | | Dandelion | Chickweed | |
| Establishing lawn from seed | 0 | 100 | 27 | 86 |
| | 250 | 46 | 8 | 45* |
| | 500 | 32 | 7 | 71 |
| | 1000 | 16 | 8 | 135 |
| LSD (0.05) | | 22 | 7 | 64 |
| Previously established lawn | 0 | 126 | 20 | 35 |
| | 250 | 47 | nd | 55 |
| | 500 | 21 | nd | 62 |
| | 1000 | 9 | 10 | 63 |
| LSD (0.05) | | 14 | 7 | 29 |

*large variance due to rabbits and geese feeding on grass in plots

These results demonstrate the control of dandelion and chickweed in lawn establishment and in established lawns. They also show the use of 85-24B for enhancing the growth of grass.

3.3 Soil Moisture and Air Temperature

Further studies examined the effect of soil moisture and temperature on weed control activity of several fungal isolates, using hulless barley as the inoculum (see above). For these experiments three soil moisture conditions (saturation, field capacity and permanent wilting point), along with 20° or 30° C. days, were considered. The results of these experiments are present in Table 24.

TABLE 24

Effect of temperature and soil moisture on the weed control activity of several fungal isolates (89-25A, 94-26, 94-359A, and 97-12B) of the present invention on Canada thistle.

| Temperature regime ° C. | Soil moisture conditions | Root weight (% of control) | |
|---|---|---|---|
| | | Trial 1 | Trial 2 |
| 30 day/10 night | Saturation | 22 a$^z$ | 31 a |
| | Field capacity | 48 b | 38 a |
| | Permanent wilting point | 100 c | 59 b |
| 20 day/10 night | Saturation | 36 a | 29 a |
| | Field capacity | 31 a | 35 a |
| | Permanent wilting point | 46 a | 66 b |

$^z$For each temperature regime, lower case letters indicate differences among soil moisture conditions averaged over four isolates.

These results illustrate that better weed control activity is obtained with higher soil moisture at either temperature.

3.4 Application methods

Methods for the application of the fungal isolates were also examined. This study considered weed control activity as a result of applying a hulless barley inoculum, or a liquid inoculum. For hulless barley, the particle size and dose response of the infected barley were examined (Table 25). For liquid inoculum, the effect of mycelial homogenates (mixed with two composts, dairy, or hog and poultry compost) on weed control activity were examined (Table 26).

Autoclaved barley was used for the preparation of a fungal inoculum as described above. Inoculated sterile barley grains are incubated for two weeks under ambient lab conditions, dried and ground with a mill (i.e. Arthur H. Thomas Co.). The control consists of uninoculated sterile grain treated in the same manner. Viability of ground inoculum is determined by plating 25 pieces on PDA plate and recording the number of particles with colony growth after 3 days and the number of colonies that resemble the original fungal isolate or are contaminants after 7 days.

To conduct the bioassay, healthy roots were cut into 10 cm long segments, making sure that each root segment had at least one bud. Root segments were washed and weighed and placed two per pot. Ground inoculum was sprinkled evenly over roots and soil surface, for example about 5 g (other doses may also be used), covered with 2-3 cm of soil mix, and the pots were placed in a greenhouse. The change in root weight at 6 weeks after root inoculation was recorded. The results are presented in Table 25.

TABLE 25

The effect of granule size and application dose on the efficacy of 85-24B to reduce root weight of Canada thistle.

| Granule size$^z$ (μ) | Application dose (g/m$^2$) | Root weight (% of control) |
|---|---|---|
| >840 | 100 | 82 |
| | 500 | 55$^y$ |
| | 1000 | 25 |
| 840-590 | 100 | 98 |
| | 500 | 74 |
| | 1000 | 6 |
| 590-49 | 100 | 45 |
| | 500 | 46 |
| | 1000 | 2 |
| Mean Pooled Standard Error | | 18 |

$^z$>840 = whole barley seed infested with 85-24B had 100% viability/particle; 840-590 = infested barley seed ground and passed through a 20 mesh, but not a 30 mesh sieve had 75% viability/particle; 590-49 = infested barley seed ground and passed through a 30 mesh sieve had 75% viability/particle.
$^y$Mean of two trials The results presented in Table 25, demonstrate that a range of barley granule sizes and application rates are effective in controlling weed growth (indicated by reduced root growth). Increased efficacy is observed with smaller sized granules and higher dose application rates.

Compost Bioassay

The fungus was grown in liquid culture as described above (see Culture of fungal isolates, Example 1). Using a double layer of cheesecloth, the liquid was drained by gravitational force from the mycelium. A ratio of about 1:3.2 (v/v) mycelium to water was homogenized to produce about 10$^5$ to 10$^6$ cfu/mL. The homogenate was mixed with composted manure in a ratio of about 1:2 (v/v).

Two segments of weed root, for example, about 10 cm for Canada thistle roots, were placed in a pot that is three quarters full with soil mix (3 sandy loam: 1 sphagnum peat moss: 1 medium grade vermiculite: 1 wash screened 9 mm sand) and packed firmly. Root segments were weighed and placed two per pot. The treated compost (compost-homogenate mix) was placed in the pot and then covered with additional soil mix before watering thoroughly. Pots were placed in a greenhouse, and the total number of shoots/pot, total number of shoots or plants with symptoms (i.e. chlorosis, necrosis, lesions) at 2, 4 and 6 weeks was recorded. Also at 6 weeks roots were collected, rinsed, and the fresh weight recorded, as was the fresh weight of foliar tissue. The data was analyzed for several parameters:

i) % root growth (i.e. [final root weight of treatment/start root weight of treatment]÷[final root weight of control/start root weight of control]×100); and ii) foliar biomass.

The results are presented in Table 26.

TABLE 26

Effect of using mycelial homogenate of 85-24B to inoculate composted manure for the control of Canada thistle.

| Compost | Treatment | Root weight % of control | Foliar fresh weight % of control |
|---|---|---|---|
| Dairy | No fungus | 100 a | 100 a |
|  | Fungus | 65 b | 76 a |
| Hog and Poultry | No fungus | 100 a | 100 a |
|  | Fungus | 28 c | 49 c |

These results demonstrate that liquid inoculum prepared as a homegenate using a variety of compost media, is effective in controlling weed growth.

Soil Drench Bioassay

The fungal isolates were grown in liquid culture as described above (see Culture of fungal isolates, Example 1). One treatment used a mixture of 94-359A, 94-44B, and 85-24B grown for about 4-8 weeks and the other treatment used 85-24B grown for 2 weeks. The mycelium and liquid culture broth were homogenized to produce about $10^3$ to $10^4$ cfu/mL. The control was uninoculated liquid culture medium. Twenty-five dandelion seeds were sown 6 mm deep in 100 mL soilless planting mix (equivalent to 0.02 $m^2$) and 100 mL of homogenate was poured on the soil. Counts were made of the number of dandelion seedlings that emerged and the number of chlorotic seedlings after 5, 7, and 14 days. The results are presented in Table 27.

TABLE 27

The effect of mycelial homogenates of fungal isolates applied as soil drench for the control of dandelion.

| Treatment | Culture Period | Mean cfu/mL | % Chlorosis 5 days | 7 days | 14 days |
|---|---|---|---|---|---|
| Control | 2 weeks | 0 | 0 | 0 | 0 |
| Fungal mixture | 4-8 weeks | $10^3$ | 100 | 100 | 100 |
| 85-24B | 2 weeks | $10^4$ | 0 | 50 | 75 |

These results demonstrate that fungal homogenates with about $10^3$ to $10^4$ cfu/mL may be applied as a soil drench at the rate of about 5 $L/m^2$ for weed control activity, and that faster and greater weed control activity is obtained with mixtures of aged inoculum.

Seed Treatment Bioassay

Isolate 94-44B was grown in liquid culture for 4 weeks as described above (See Culture of fungal isolates, Example 1). The mycelium and liquid culture broth were homogenized to produce about $10^3$ to $10^4$ cfu/mL. The fungal homogenate (1 mL) and 1 mL of 2% methocil (a cellulose sticker) was used to coat 36 seeds of Katewpa wheat (138 cfu/seed) or 173 seeds of creeping red fescue grass seed (29 cfu/seed) in a glass Petrie dish. The coated seed was air-dried overnight in a laminar flow hood. The wheat seeds and 20 dandelion seeds were planted in a 4 inch pot with soil-less planting medium and watered thoroughly. The % of dandelion plants with chlorosis and the fresh weight biomass of wheat were recorded 14 days later. See Table 28.

TABLE 28

The effect of treating the seed of a crop with fungal isolate 94-44B on the control of dandelion and on crop growth.

| Treatment | No. of chlorotic dandelions % | Crop Biomass (% of untreated control) |
|---|---|---|
| Grass seed - treated | 6 | 116 |
| Grass seed - untreated | 0 | 100 |
| Wheat seed - treated | 23* | 122* |
| Wheat seed - untreated | 0 | 100 |

*significantly different than the untreated control at $P < 0.05$

These results demonstrate that the inventive fungal isolate may control dandelions by seed treatment of crops. It also demonstrates a dose effect such that larger seeds with more cfu/seed gave greater control than smaller seeds with fewer cfu/seed.

3.5 Pre- and Post-emergence Foliar Spray Applications

Isolate 94-44B was grown in liquid culture for four weeks as described above (See Culture of fungal isolates, Example 1). The liquid culture was filtered through a nylon mesh cloth and the liquid culture broth and the mycelial fractions were saved separately. A 150 ml aliquot of the liquid culture broth was filtered through a 0.45 um cellulose acetate filter to produce the filtered culture broth treatment. Another 150 ml aliquot of the liquid culture broth had 15% mycelium (w/v) added to it and was then homogenized to produce the treatment called the unfiltered liquid culture broth containing $10^6$ to $10^7$ propagules/ml. Propagules comprised both mycelial fragments and spores. These two treatments plus a water control were sprayed onto 6-4 inch pots using a track sprayer at a rate of 480 L/ha. Each pot was seeded with 0.11 g of grass cv. Overseeding Mixture and 20 dandelion seeds in a soiless planting medium. Pots were sprayed 1-2 days after seeding as a pre-emergent foliar spray application. Pots were also sprayed two weeks after seeding as a post-emergence foliar spray application. Three weeks after spraying, the following data were recorded: total number of dandelions per pot, number of chlorotic dandelions per pot, fresh weight of grass per pot in grams, fresh weight of dandelion per pot in grams. (See Table 29).

TABLE 29

The effect of pre- and post-emergent spray applications of liquid culture broths of isolate 94-44B.

| Time of Application | Spray Treatment | Fresh weight (as % water control) Grass | dandelion | Number of dandelions Chlorotic (%) | Total |
|---|---|---|---|---|---|
| Pre-emergent | Filtered culture broth | 123 b | 16 c | 38 c | 5 b |
|  | Unfiltered culture broth | 159 a | 31 bc | 56 b | 7 ab |
|  | Water Control | 100 b | 100 a | 0 a | 10 a |
| Post-emergent | Filtered culture broth | 113 a | 20 b | 89 b | 5 a |

TABLE 29-continued

The effect of pre- and post-emergent spray applications of liquid culture broths of isolate 94-44B.

|

TABLE 30B

The effect of fungal isolates on chlorosis of agriculturally important plants. The plus symbol indicates a detrimental effect to one or more cultivars tested and the letter indicates the number of cultivars affected (a = 1; b = 2; c = 3; d = 4; e = 5).

| Crop | No. of cultivars | 85-24B | 94-26 | 94-44B | 94-134 | 95-54A1 | 97-12B | 89-25A | 94-359A | 95-268B | 97-15B2 |
|---|---|---|---|---|---|---|---|---|---|---|---|
| Weat | 5 | − | − | − | − | − | − | − | − | − | − |
| Barley | 2 | − | − | − | − | − | − | − | − | − | − |
| Oat | 1 | − | − | − | − | − | − | − | − | − | − |
| Millet | 1 | − | − | − | − | − | − | +a | − | − | +a |
| Canaryseed | 1 | − | − | − | − | − | − | − | − | − | − |
| Canola | 2 | +b | − | +b | +a | +b | +b | +b | − | +b | − |
| Mustard | 2 | +b | − | +b | − | +b | +b | +b | +a | +b | − |
| Fax | 1 | +a | − | − | − | − | − | +a | − | − | − |
| Sunflower | 1 | +a | − | +a | − | +a | − | +a | − | − | − |
| Safflower | 1 | +a | − | +a | − | +a | − | − | − | − | +a |
| Lentil | 2 | +b | +b | +b | +a | +b | − | +a | +a | − | +a |
| Field pea | 1 | +a | +a | +a | − | +a | − | − | − | − | +a |
| Chickpea | 1 | +a | − | +a | − | +a | − | − | − | − | +a |
| Faba bean | 1 | +a | +a | +a | − | +a | − | − | − | − | +a |
| Clovers | 5 | +d | − | +c | − | +c | +b | +c | +c | +b | +c |
| Birdsfoot trefoil | 1 | +a | − | +a | − | − | − | +a | +a | +a | +a |
| Alfalfa | 1 | + | +a | +a | − | +a | +a | +a | − | +a | +a |

+ indicates a detrimental effect on at least one or more cultivars tested for each crop using ANOVA to compare treatment and control at P = 0.05;
− indicates no detrimental response to the treatment using ANOVA to compare treatment and control at P = 0.05

TABLE 30C

The effect of fungal isolates on foliar fresh weight of agriculturally important plants. The plus symbol indicates a detrimental effect to one or more cultivars tested and the letter indicates the number of cultivars affected (a = 1; b = 2; c = 3; d = 4; e = 5).

| Crop | No. of cultivars | 85-24B | 94-269 | 94-44B | 94-134 | 95-54A1 | 97-12B | 89-25A | 94-359A | 95-268B | 97-15B2 |
|---|---|---|---|---|---|---|---|---|---|---|---|
| Weat | 5 | +a | na | − | +a | +a | − | − | − | − | − |
| Barley | 2 | − | na | − | − | − | − | − | +a | − | − |
| Oat | 1 | +a | na | − | − | − | − | − | − | − | − |
| Millet | 1 | − | na | − | − | +a | − | +a | − | − | +a |
| Canary seed | 1 | − | na | − | − | − | − | − | − | − | − |
| 16Canola | 2 | +a | na | − | +a | +b | +a | +b | +b | +b | +b |
| Mustard | 2 | +a | na | na | − | +b | +b | +a | +a | +a | +b |
| Flax | 1 | +a | na | − | − | +a | − | − | − | − | +a |
| Sunflower | 1 | na | na | +b | na | +a | − | − | na | na | na |
| Safflower | 1 | +a | na | − | − | − | − | − | − | − | +a |
| Lentil | 2 | +b | na | +a | +a | +a | +a | +a | +b | − | +b |
| Field pea | 1 | +a | na | − | − | +a | − | − | − | − | +a |
| Chickpea | 1 | − | na | +a | − | − | +a | − | +a | − | +a |
| Faba bean | 1 | +a | na | − | − | +a | − | − | − | − | +a |
| Clovers | 5 | +b | na | +b | − | +b | +b | +a | +b | +c | +c |
| Birdsfoot trefoil | 1 | +a | na | +a | − | − | − | +a | +a | +a | +a |
| Alfalfa | 1 | +a | +a | +a | − | +a | +a | +a | − | +a | +a |

+ indicates a detrimental effect on at least one or more cultivars tested for each crop using ANOVA to compare treatment and control at P = 0.05;
− indicates no detrimental response to the treatment using ANOVA to compare treatment and control at P = 0.05

TABLE 30D

The effect of fungal isolates on mortality of agriculturally important plants. The plus symbol indicates a detrimental effect to one or more cultivars tested and the letter indicates the number of cultivars affected (a = 1; b = 2; c = 3; d = 4; e = 5).

| Crop | No. of cultivars | 85-24B | 94-26 | 94-44B | 94-134 | 95-54A1 | 97-12B | 89-25A | 94-359A | 95-268B | 97-15B2 |
|---|---|---|---|---|---|---|---|---|---|---|---|
| Weat | 5 | − | − | − | − | − | − | − | − | − | − |
| Barley | 2 | − | − | − | − | − | − | − | − | − | − |
| Oat | 1 | − | − | − | − | − | − | − | − | − | − |
| Millet | 1 | − | +a | − | − | − | − | − | − | − | +a |
| Canary seed | 1 | − | − | − | − | − | − | − | − | − | − |
| Canola | 2 | +b | +a | +b | +a | +b | +b | +b | − | +b | +b |
| Mustard | 2 | +b | − | +b | − | +b | +b | +b | +a | +b | +b |
| Flax | 1 | +a | − | − | − | − | − | − | − | − | +a |
| Sunflower | 1 | +a | − | na | na | +a | − | +a | na | na | na |
| Safflower | 1 | +a | − | +a | − | +a | − | − | − | − | +a |
| Lentil | 2 | +b | +a | +b | − | +b | − | − | − | − | − |
| Field pea | 1 | +a | − | +a | − | +a | − | − | − | − | − |
| Chickpea | 1 | − | − | +a | − | +a | − | − | − | − | − |

TABLE 30D-continued

The effect of fungal isolates on mortality of agriculturally important plants. The plus symbol indicates a detrimental effect to one or more cultivars tested and the letter indicates the number of cultivars affected (a = 1; b = 2; c = 3; d = 4; e = 5).

| Crop | No. of cultivars | 85-24B | 94-26 | 94-44B | 94-134 | 95-54A1 | 97-12B | 89-25A | 94-359A | 95-268B | 97-15B2 |
|---|---|---|---|---|---|---|---|---|---|---|---|
| Faba bean | 1 | − | − | +a | − | − | − | − | − | − | − |
| Clovers | 5 | +e | − | +a | +a | +b | +a | +c | +a | +d | +d |
| Birdsfoot trefoil | 1 | +a | − | +a | − | − | − | +a | − | +a | +a |
| Alalfa | 1 | +a | +a | +a | − | +a | +a | +a | − | +a | +a |

+ indicates a detrimental effect on at least one or more cultivars tested for each crop using ANOVA to compare treatment and control at P = 0.05;
− indicates no detrimental response to the treatment using ANOVA to compare treatment and control at P = 0.05

The results presented in Tables 30A-D demonstrate that many plant cultivars of important agricultural species are not affected by fungal isolates of the present invention when applied at high inoculum loads, and that these isolates may be used as a bioherbicide to control weed activity in the presence of crops. Lower inoculum loads, that are effective in exhibiting weed control activity but not harmful to crop plants, may be used to minimize the impact on agriculutral plants if desired.

B) Hulless Barley Inoculum

To determine the residual effects of a single application of fungal isolates of the present invention on agriculturally important crops grown in the field, sample fungal isolates were applied to the soil using the hulless barley inoculum at 1 kg/m$^2$ at three different periods within the growth season to control Canada thistle (See Example 3, Duration of Application). Lentil seed of the cultivar Laird was sown into the treated and control areas at the rate of 70-80 kg/ha approximately 10-14 months after the time of bioherbicide application. The number of lentil plants emerged per plot and the number of plants with chlorosis were counted. The results of this experiment are presented in Table 31. The data of a similar experiment, on Canada thistle, is presented in Table 22.

TABLE 31

The effect of residual fungal inoculum of 85-24B applied to the soil on the mean emergence of lentil per plot and mean number of lentil plants with chlorosis per plot.

| Treatment | Emergence | Chlorosis |
|---|---|---|
| Control | 38 ± 12 S.E. | 0 |
| Applied: | | |
| June 1999 | 46 ± 1 | 1.5 |
| August 1999 | 40 ± 13 | 0 |
| October 1999 | 19 ± 3 | 0.3 |

These results demonstrate that fungal isolates in the present invention do not have harmful residual activity to agriculturally important field crops when applied at high rates of field application in the spring and summer under natural conditions of infection.

EXAMPLE 5

Phytotoxin Production

The weed control activity of heat killed fungal isolates was examined. Hulless barley inoculum was heat killed and applied to Canada thistle or the heat-killed innoculum was mixed with grass seed contaminated with 5% dandelion seed as described below (Tables 32 and 33). The results indicate that heat killed fungal isolates retain weed control activity. Therefore, the effect of filtered inoculated broth or extracts of fungal isolates of the present invention on weed growth was also examined (Table 34).

5.1 Weed Control by the Fungal Agent or by Metabolites Produced by the Fungal Agent Hulless barley grains inoculum is prepared as outlined above (Example 3). The barley inoculum is autoclaved and applied to soil in which Canada thistle is grown or the inoculum is mixed with grass seed contaminated with 5% dandelion seed (see above Example 3). As a control, regular barley grain or non-infested barley inoculum were applied to the soil. These results were repeated under greenhouse and field conditions. The results of the experiments are shown in Table 32 and Table 33.

TABLE 32

The effect of heat-killed fungal-infested barley grains on Canada thistle.

| Treatment | Chlorosis | Root weight % of control | Mortality % |
|---|---|---|---|
| Fungal Isolate 89-25A | | | |
| Untreated control | no | 100 a | 0 |
| Infested grain | yes | 9 b | 70 c |
| Autoclaved grain | yes | 33 b | 20 ab |
| Fungal Isolate 97-12B | | | |
| Untreated control | no | 100 a | 0 |
| Infested grain | yes | 67 ab | 30 b |
| Autoclaved grain | yes | 55 ab | 17 ab |

Different letters within a column indicate significant differences at P<0.05 using Duncans multiple range test. Fungal viability of infested grain was 100% while the viability in the autoclaved sample was 0%.

These experiments demonstrate that heat killed fungal inoculum exhibits weed control activity, and that live fungal inoculum is not required for weed control activity. These results suggest that a natural product is made by fungal isolates of the present invention. Crude extracts of a phytotoxin fraction were obtained and analysed for weed control activity.

TABLE 33

The effect of heat-killed fungal infested barley grains (isolate 85-24B) on emergence of dandelion in turf.

| Treatment | Average No. dandelion per plot | Biomass of Grass per plot (Fresh wt. g.) |
|---|---|---|
| No grain | 117 | 50 |
| Grain | 48 | 57 |
| Infested grain | 19 | 69 |
| Heat-killed infested grain | 16 | 98 |
| LSD (0.05) | 16 | 29 |

Field test conducted in mid-August and ran for 4 weeks before taking biomass.

These results demonstrate that the fungal agent or metabolites produced by the fungal agent may control dandelion in lawns and that the metabolites may improve the growth of the grass.

5.2 Phytotoxin Extraction and Bioassay

Fungal isolates were grown in liquid culture media on a shaker for 4 weeks under ambient light and temperature conditions. The culture was separated into a broth and a mycelium fraction by vacuum filtration using Buchner funnel lined with Whatman #1 filter paper and 2-4 layers of cheesecloth. The broth fraction (filtered inoculated broth) was reduced to dryness either a using a roto-evaporator (40° C.) or freeze-dryer. The mycelium fraction was placed in the chloroform for 3 hours to overnight then vacuum filtered through Whatman #1 filter paper to separate solvent and mycelium. The filtered solvent was roto-evaporated to dryness. The control was uninoculated liquid culture media treated the same as the broth fraction. The dried extracts were stored in flasks in the refrigerator until used. For testing, the dried extracts from both the broth and mycelium fractions were first dissolved in 2-5 ml of distilled water and then an equal amount of 80% methanol was added to each flask. The control treatment was 40% methanol. Methanol and ethyl acetate extracts were also obtained from the mycelium fraction following the chloroform extraction step, and examined for weed control activity as described below.

A bioassay was used to determine the presence of phytotoxins in droplets of the fractions that caused chlorotic symptoms similar to that caused by the fungus on leaves of a susceptible plant (in this example, faba bean was used as a test plant) or Canada thistle (weed host). Faba bean seeds were planted into soil mix and thinned to 5 plants per pot using 2 pots per treatment. Canada thistle roots were planted in soil mix and after 3 weeks, pots with 2-3 shoots were selected. Two—10 ul drops of an extract were applied to 2 leaves per faba bean plant and 3 leaves per Canada thistle shoot; one droplet over a puncture wound made from an insect pin and the other droplet directly on the leaf surface. Plants were observed daily for 10 days for chlorosis.

A different bioassay was used to determine the impact of the phytotoxins from the fractions on the fresh weight of faba bean. In this assay, faba bean seeds were mixed with 1 ml of extract and 1 ml of 2% methocil to coat the seeds and then left to air dry overnight. Five seeds were planted per pot in soil mix. Plants were rated for emergence and chlorosis after 10 days, and foliar biomass (fresh weight) after 4 weeks.

The weed control activity of these solvent extracts are present in Table 34 (chloroform extract) and Table 35 (chloroform, methanol or ethyl acetate extracts).

Weed control activity, determined by the percentage of chlorotic plants (faba bean, FB or Canada thistle, CT) observed 10 days after receiving droplets of a chloroform extract obtained from fungal isolate 94-26, is presented in Table 34

TABLE 34

Weed control activity of a solvent extract of a fungal isolate of the present invention. Solvent control is 40% methanol, or the uninoculated broth.

| | % chlorotic plants | | | | | |
|---|---|---|---|---|---|---|
| | Trial 1 | | Trial 2 | | Trial 3 | Trial 4 |
| Treatment | FB | CT | FB | CT | FB | FB |
| Solvent control | 0 | 0 | 0 | 0 | 0 | 0 |
| Uninoculated broth | 0 | 0 | 0 | 0 | 0 | 0 |
| Filtered Inoculated broth | 100 | 67 | 90 | 80 | 100 | 100 |
| Mycelium-chlorofom | 100 | 100 | 0 | 0 | 0 | 100 | treatment n = 10 plants

The weed control activity of chloroform, methanol, or ethyl acetate fractions is also examined. Weed control activity is assayed by monitoring emergence, chlorosis, and foliar fresh weight of faba bean that had seed treated with various solvent extracts from 94-26, or uninoculated control broth. The results of this experiment are present in Table 35.

TABLE 35

Weed control activity of various solvent extracts of a fungal isolate of the present invention.

| Treatment | Emergence % | Chlorosis % | Fresh weight g |
|---|---|---|---|
| Uninoculated broth | 93 a | 0 | 36 a |
| Filtered Inoculated broth | 100 a | 100 b | 18 cd |
| Mycelium-chloroform | 100 a | 100 b | 11 d |
| Mycelium-methanol | 87 a | 87 b | 20 bc |
| Mycelium-ethyl acetate | 93 a | 13 a | 37 a | n = 15 plant; Different letters within a column indicate significant differences at P < 0.05 using a LSD test The results presented in Tables 34 and 35 demonstrate that filtered inoculated broth and solvent extracts obtained from the fungal isolates of the present invention induce disease symptoms, reduce growth, and exhibit weed control activity in susceptible plants. Therefore, filtered inoculated broth, extracts from mycelium, or a combination thereof, may be used to control weed growth.

EXAMPLE 6

Figure 7:
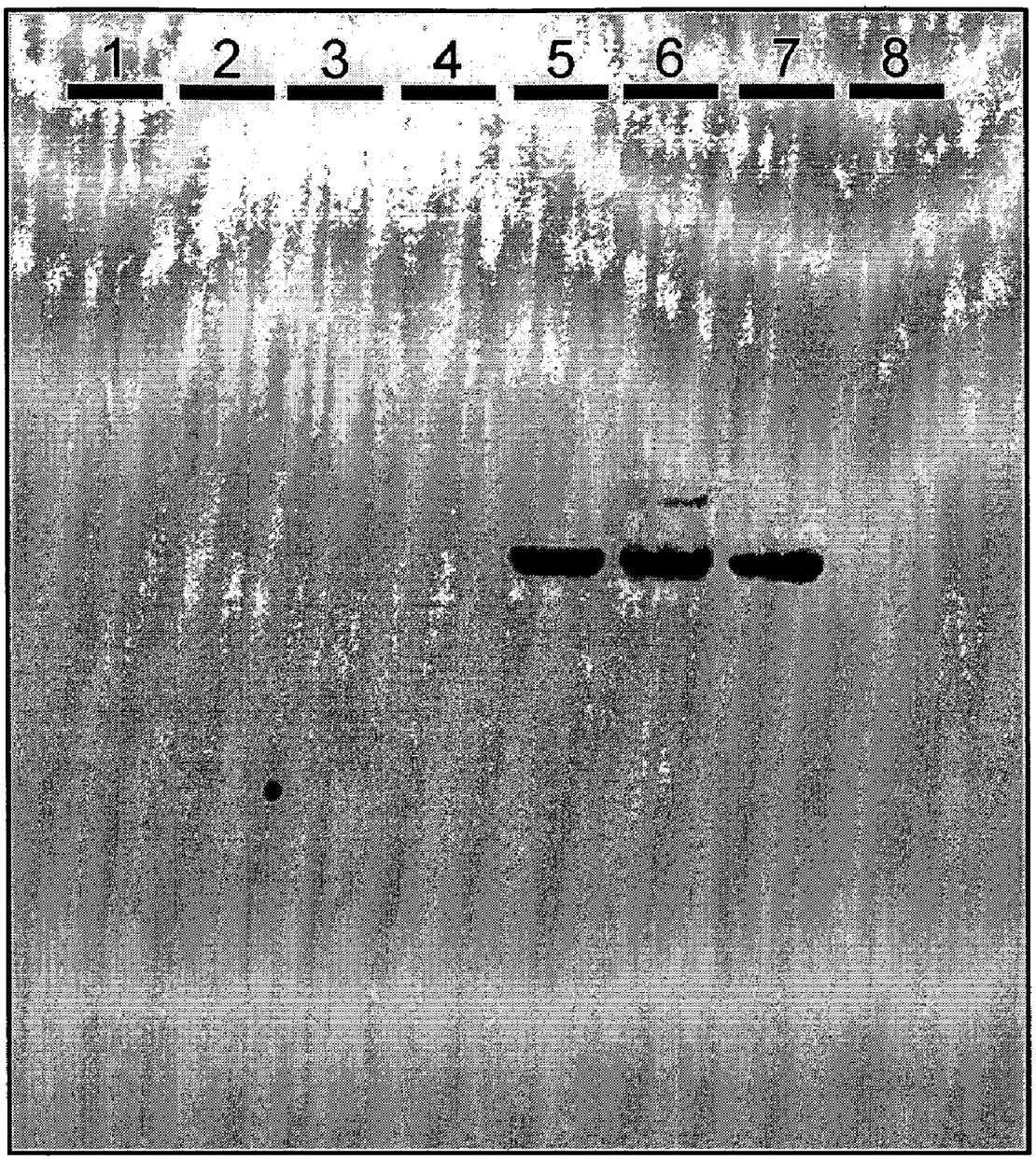
FIG. 7 shows Southern hybridization of the generated probe (SEQ. ID. NO:1) with genomic DNA from three isolates of *P. macrostoma* with bioherbicidal activity. Lanes 1: Gene Ruler™ 1 kb Ladder. Lanes 2-4: uncut DNA of *P. macrostoma* isolates 85-24B, 94-44B, and 95-54A1, respectively. Lanes 5-7: SacI-KpnI digested DNA of *P. macrostoma* isolates 85-24B, 94-44B, and 95-54A1, respectively. Lane 8: 100 bp marker.

Development of PCR Probe for Detecting Isolates of *Phoma macrostoma* that Exhibit Weed Control Activity 6.1 Plasmid DNA Isolation and DNA Probe Sequencing Genomic DNA from isolates 94-44B, 95-54A1, and 85-24B was digested with SacI and KpnI restriction enzymes to create several 1-2 kb length fragments. The fragments were cloned into *E. coli* DH5α with the plasmid pBluescript KSII (Stratagene). Using Southern hybridization, one fragment from 85-25B was found to bind to genomic DNA of 94-44B, 95-54A1, and 85-24B (FIG. 7). This fragment was used as a probe for a Southern hybridization to chromosomal DNA from 7 other isolates of *P. macrostoma* that had demonstrated weed control activity (see Example 2.2), plus one isolate of *P. medicaginis* and 3 isolates of *P. herbarum*. The results of the Southern Hybridization are shown in FIG. 8

Figure 8:
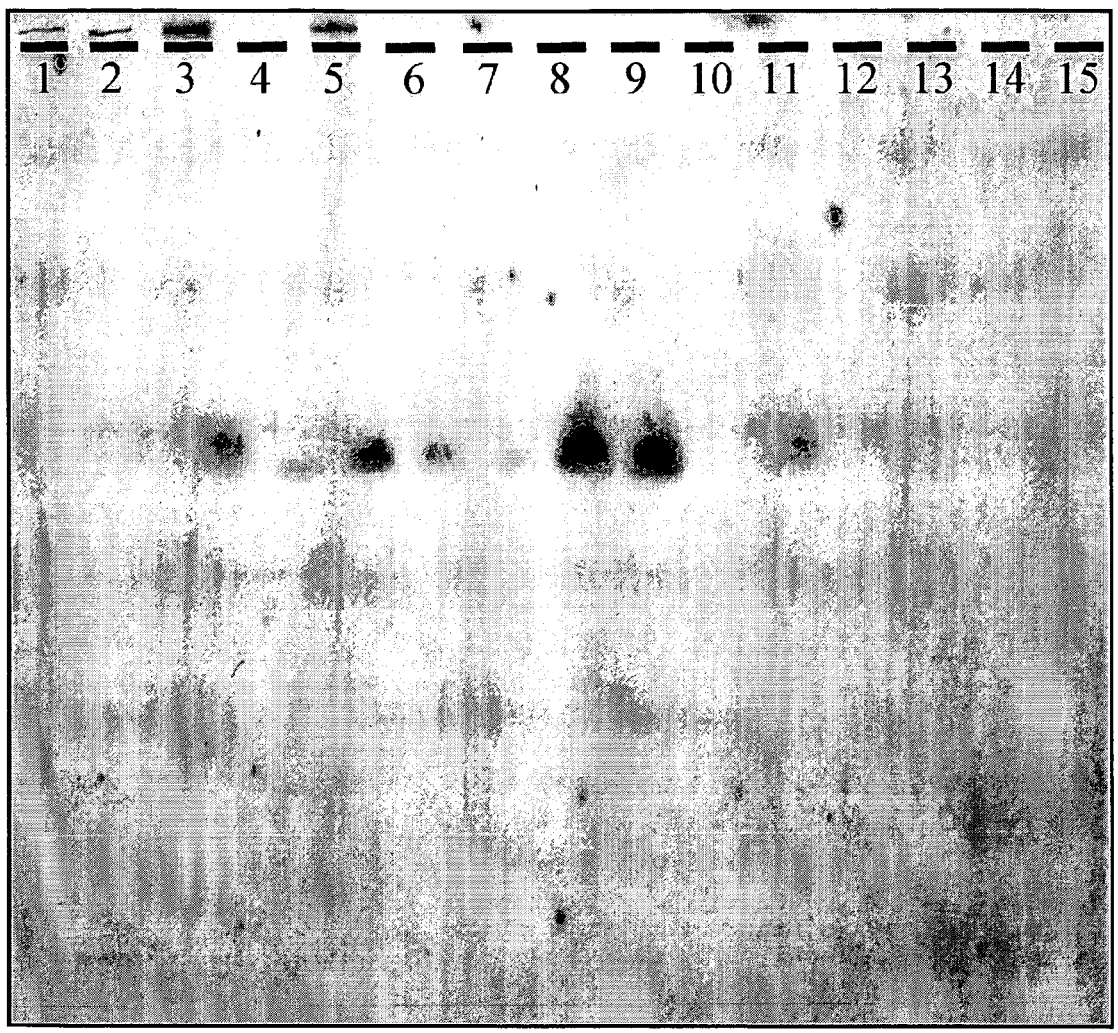
FIG. 8 shows Southern hybridization of the probe (SEQ. ID. NO: 1) with chromosomal DNA from isolates of *P. macrostoma* with bioherbicidal activity, and two other *Phoma* species that do not have bioherbicidal activity. Lanes 1-15: 100 bp marker, *P. macrostoma* 85-24B, *P. macrostoma* 89-25A2, *P. macrostoma* 94-26, *P. macrostoma* 94-44B, *P. macrostoma* 94-134, *P. macrostoma* 94-359A, *P. macrostoma* 95-54A1, *P. macrostoma* 95-268, *P. macrostoma* 97-12B, *P. macrostoma* 97-15B2, *P. medicaginis* 94-335A1, *P. herbarum* AI, *P. herbarum* AIV, and *P. herbarum* G5/2.

The probe hybridized to 8 of the 10 *P. macrostoma* isolates, but did not hybridize to the other *Phoma* species tested (FIG. 8).

Plasmid DNA (pBluescript KSII containing the probe) was isolated using the QIAGEN® Spin Miniprep Kit. The probe (SacI-KpnI insert) was sequenced at the Plant Biotechnology Institute, National Research Council Canada, Saskatoon. The nucleotide sequence of the probe (SEQ. ID. NO: 1) is presented in FIG. 9.

6.2 PCR Primer Design and Conditions

Based on SEQ. ID. NO: 1, a pair of primers were designed for PCR detection of *P. macrostoma* isolates:

```
Left primer:
ACA GCT TCG ACA ATG GCT CT;    [SEQ. ID. NO: 2]
and

Right primer:
ACA TTC GCG TAG TTC CCA AC     [SEQ. ID. NO: 3]
```

However, other primer pairs may be used as desired.

The 25-μl PCR reaction mixture was comprised of 14.7 μl of Ultra-pure water, 2.5 μl of GeneAmp® 10×PCR Buffer II, 2.0 μl of MgCl$_2$ (25 mM), 2.0 μl of dNTP mix (MBI Fermentas, 2 mM each), 1.25 μl of each primer (5 μM), 0.3 μl of AmpliTaq Gold polymerase (5 U/μl, Applied Biosystems), and 1.0 μl of template DNA (10 ng/μl). The PCR program comprised an initial denaturation at 94° C. for 10 min, followed by 35 cycles of 94° C., 2 min (denaturation), 60° C., 2 min (annealing) and 72° C., 3 min (extension), followed by a final extension at 72° C. for 10 min. All PCR reactions were performed in an Alpha Unit™ Block Assembly for PTC DNA Engine™ Systems (MJ Research, Inc., Waltham, Mass.). The primer pair yields a PCR product of 853 bases corresponding to 449 to 1301 nucleotides of SEQ. ID. NO: 1 as shown in FIG. 10.

6.3 Methods for Testing Primer Pair for Specificity to *P. macrostoma*

The fungal cultures used for specificity testing the PCR primers are listed in Table 36. Fungal isolates were preserved by maintaining a hyphal fragment and spore suspension in a 1:1 skim milk (10% v/v) to glycerol (40% w/v) solution and then stored at −80° C. Isolates were revived by thawing a vial containing the fungus to room temperature. The contents were aseptically spread on the surface of 15-cm diameter petri dishes containing Difco potato dextrose agar (PDA) or V-8® juice agar augmented with 3 ml of 85% lactic acid per liter of media. The plates were incubated at room temperature with natural light for 1-2 weeks. Genomic DNA was extracted from each of the fungal isolates as described below.

TABLE 36

Isolates of *Phoma* species

| Species | Isolate | Host of origin | Place of Origin[a] | Source[b] |
|---|---|---|---|---|
| *Phoma macrostoma* | 85-24B | *Cirsium arvense* (L.) Scop. | Saskatchewan, Canada [3] | SRC/IDAC |
| *P. macrostoma* | 89-25A2 | *Cirsium arvense* | Saskatchewan, Canada [3] | SRC/IDAC |
| *P. macrostoma* | 94-26 | *Cirsium arvense* | Ontario, Canada [4] | SRC/IDAC |
| *P. macrostoma* | 94-44B | *Cirsium arvense* | Saskatchewan, Canada [3] | SRC/IDAC |
| *P. macrostoma* | 94-134 | *Cirsium arvense* | New Brunswick, Canada [4] | SRC/IDAC |
| *P. macrostoma* | 94-359A | *Cirsium arvense* | Saskatchewan, Canada [3] | SRC/IDAC |
| *P. macrostoma* | 95-54A1 | *Cirsium arvense* | Nova Scotia, Canada [4] | SRC/IDAC |
| *P. macrostoma* | 95-268B | *Cirsium arvense* | Saskatchewan, Canada [3] | SRC/IDAC |
| *P. macrostoma* | 97-12B | *Cirsium arvense* | Alberta, Canada [3] | SRC/IDAC |
| *P. macrostoma* | 97-15B2 | *Cirsium arvense* | Alberta, Canada [3] | SRC/IDAC |
| *P. macrostoma* var. *incolorata* | CBS 839.84 | *Hordeum vulgare* L. | Monheim, Germany | CBS |
| *P. macrostoma* var. *macrostoma* | CBS 154.83 | *Philadelphus coronaries* L. | Baarn, Netherlands | CBS |
| *P. macrostoma* var. *macrostoma* | CBS 482.95 | *Larix decidua* Mill. | Munchen, Germany | CBS |
| *P. macrostoma* var. *macrostoma* | CBS 488.94 | *Forsythia* sp. | Baarn, Netherlands | CBS |
| *P. macrostoma* var. *macrostoma* | CBS 837.84 | *Triticum aestivum* L. | Munheim, Germany | CBS |
| *P. dennisii* var. *dennisii* | CBS 135.96 | *Solidago Canadensis* L. | Ontario, Canada [4] | CBS |
| *P. lingam* | Leroy | *Brassica napus* L. | Saskatchewan, Canada [3] | SRC |
| *P. lingam* | Peace-3 | *Brassica napus* | British Columbia, Canada [1] | SRC |
| *P. lingam* | P1 86-12 | *Brassica napus* | Manitoba, Canada [3] | SRC |
| *P. lingam* | P1 89-19 | *Brassica* sp. | Unknown, Australia | SRC |
| *P. lingam* | P1 89-21 | *Brassica napus* | Mt Barker, Australia | SRC |
| *P. herbarum* | AI | *Taraxacum officinale* Webber ex F. H. Wigg. | Ontario, Canada [4] | G. Boland |
| *P. herbarum* | AIV | *Taraxacum officinale* | Ontario, Canada [4] | G. Boland |
| *P. herbarum* | G/5/2 | *Taraxacum officinale* | Ontario, Canada [4] | G. Boland |
| *P. chrysanthemicola* | 90-64 | *Ambrosia artemisifolia* | Ontario, Canada [4] | SRC |
| *P. chrysanthemicola* | 91-271 | *Ambrosia artemisifolia* | Ontario, Canada [4] | SRC |
| *P. exigua* | 92-180-1 | *Cirsium arvense* | Manitoba, Canada [3] | SRC |
| *P. medicaginis* | 94-335A1 | *Medicago lupulina* L. | Saskatchewan, Canada [3] | SRC |
| *P. nebulosa* | 92-74 | *Cirsium arvense* | Saskatchewan, Canada [3] | SRC |
| *P. pomorum* | 91-177 | *Ambrosia artemisifolia* | Iowa, USA | SRC |
| *Cochliobolus sativus* | 2715 | *Hordeum vulgare* | Ontario, Canada [4] | SRC |
| *Epicoccum purpurascens* | 98-SD85-18 | *Setaria viridis* L. (Beauv.) | Saskatchewan, Canada [3] | SRC |
| *Fusarium oxysporum* | 91-121B | *Ambrosia artemisiifolia* | Ontario, Canada [4] | SRC |
| *Penicillium* sp. | 02-10 | *Lens culinaris* Medik. | Saskatchewan, Canada [3] | SRC |
| *Pythium* sp. | 94-123-B (1) | *Setaria viridis* | New Brunswick, Canada [4] | SRC |
| *Sclerotinia sclerotiorum* | SS-321 | *Brassica napus* | Saskatchewan, Canada [3] | SRC |
| *Septoria cirsii* | 98-11B2 | *Cirsium arvense* | Saskatchewan, Canada [3] | SRC |

[a]The number in parentheses refers to the Canadian ecozone.
[b]SRC = Saskatoon Research Centre, Agriculture and Agri-Food Canada, Saskatoon, Canada; IDAC = isolates deposited at the International Depository Authority of Canada, Winnipeg, Canada; CBS = Centraalbureau voor Schimmelcultures, Utrecht, The Netherlands.

6.4 Methods for Testing Primer Pair for Sensitivity to *P. macrostoma*

Inoculum of *P. macrostoma* 94-44B was grown on sterilized, hulled barley grain in loosely sealed, 250-ml canning jars. The grain was inoculated with 10 ml of fungal inoculum suspension made from a 2-week-old culture plate homogenized for 30 seconds (Polytron Kinematica Pt 10-35 at setting 5-7) in 300 ml water supplemented with 3 ml of an antibiotic stock solution (1% streptomycin and 0.5% vancomycin). Inoculated jars were incubated for 2 weeks under ambient laboratory conditions and infested grains then dried on foil-lined trays under ventilated conditions. Grains were then ground to 49-840 μm particles.

The ground inoculum was used to apply 7 fungal dose treatments (i.e. 0, 4, 8, 16, 31, 63, and 125 g/$m^2$ surface area) to 10.5 $cm^2$ pots under greenhouse conditions. To obtain an even distribution of the fungal inoculum over the surface, especially at lower inoculum rates, all dose treatments were mixed with a proportion of uninfested ground barley, such that the total amount of grain applied to each pot was equivalent to the rate of 125 g/$m^2$. Sown in each pot were 20 dandelion seeds and 0.11 g of turf grass "Overseeding Mixture" (containing 40% Perennial Rye (*Lolium perenne* L., cvs. Manhattan III and Calypso II), 25% Kentucky Blue Grass (*Poa pratensis* L., cvs. Quantum Leap and Alene), 15% Chewings Fescue (*Festuca rubra* var. *commutata* Gaud.), 10% Creeping Red Fescue (*Festuca rubra* L.), 10% Roughstalk Bluegrass (*Poa trivialis* L.).

The dandelion was rated for percentage of chlorosis at 10 days after inoculum application. After 3 weeks, soil and roots of grass and dandelion were collected and sampled for DNA extraction. The experimental design was a randomized complete block with 4 replications.

6.5 Methods for Genomic DNA Extraction from Fungal Cultures, Plant and Soil

Fungal cultures were grown on PDA plates for DNA isolation using QIAGEN® DNeasy® Plant Mini Kit. Approximately 100 mg of mycelium and spores from the wet surface of the culture plate were scraped and ground in liquid nitrogen in an Eppendorf tube using a mini plastic pestle. The follow-up procedures were completed according to the manufacturer's instructions (QIAGEN Inc., Mississauga, Ontario).

Plants were carefully removed from soil to keep the roots intact. The plant sample was mostly turfgrass with some dandelion occasionally present. The plant roots were placed in a beaker of water and shaken for 30 min to remove attached soil, and then rinsed under tap water until the roots were visibly free of soil particles. The samples were shaken again in tap water for 30 min and then rinsed with tap water. After a final rinse with distilled water, the roots were cut from the above-ground tissues and blotted with paper towel. Plant DNA was extracted using a protocol based on Edwards et al. (1991) *Nucl. Acids Res.* 19: 1349 with an RNase-A treatment followed by a phenol-chloroform extraction.

The UltraClean™ Soil DNA Kit (MO BIO Laboratories, Inc., Solana Beach, Calif.) was chosen for extracting DNA from the soil samples. For each sample, 0.3 g of fine soil particles of less than 1 mm diameter and free of obvious plant debris were used according to the manufacturer's directions.

6.6 Results of Specificity and Sensitivity Testing with PCR Primers

Fifteen isolates of *P. macrostoma*, 13 isolates representing 8 other *Phoma* species, and 7 isolates of common soil fungi from 7 other genera (Table 36) were tested for their specificity to the PCR primers. The primer pair (SEQ. ID. NO: 1; SEQ. ID. NO: 2) was highly specific to all 10 *P. macrostoma* isolates possessing weed control activity as shown in FIG. 11. These isolates all were originally isolated from *C. arvense* (Canada thistle). Other isolates of *P. macrostoma* originally isolated from other hosts such as *H. vulgare, Philadelphus coronaries* L., *Larix deciduas* Mill., *Forsythia* sp., and *Triticum aestivum* L. were not detected. Similarly, isolates of eight different *Phoma* species and 7 other genera were not detected by the primers.

To evaluate how sensitive the PCR primers were in detecting low levels of isolate 94-44B, soil and plant root samples were taken from pots treated with varying doses of inoculum (0-125 g/$m^2$) in the greenhouse trial. The biocontrol isolate was not detected in soil samples with 0 g/$m^2$, but it was detected from soil with treatments ranging from 4 g/$m^2$ to 125 g/$m^2$ of inoculum as shown in FIG. 12. In plant roots, isolate 94-44B was detected at doses between 8 g/$m^2$ and 125 g/$m^2$, but not at the lowest dose of 4 g/$m^2$ (FIG. 12). Before sampling the plants for DNA extraction, symptoms of severe chlorosis were observed on dandelion seedlings in treatments with high rates of inoculum. The percent chlorosis at the doses of 0, 4, 8, 16, 31, 63, and 125 g/$m^2$ was 0, 19, 28, 64, 93, 92, and 100%, respectively ($LSD_{0.05}$=2.9).

6.7 Primer Specific Identification of *Phoma macrostoma* from World Collections Using PCR Primer Pair Sixty-two isolates of *P. macrostoma* originating from a diverse range of hosts and geographic origins were acquired from various collections (Table 5). Upon receipt, isolates were resuscitated, single spored and cultured on potato dextrose agar (PDA; Difco Laboratories, Detroit, Mich., USA) supplemented with 85% lactic acid (3 ml/L). Cultures were incubated at 23° C.±1 under 12 hour light provided by two 40-W, 120 cm long cool white fluorescent tubes placed 30 cm above the plates. Fungal isolates were preserved by maintaining a hyphal fragment and spore suspension in a 1:1 skim milk (10% v/v) to glycerol (40% v/v) solution and then stored at −80° C.

Single spore cultures of each isolate were grown for 5-7 days on PDA, after which mycelial plugs were transferred to 250 ml Erlenmeyer flasks containing 100 ml of potato dextrose broth and incubated on an orbital shaker (150 rpm) at 23±1° C. for 7 days. Mycelium was harvested by filtration, lyophilised and ground in a 2 ml Wheaton-Tenbroek tissue grinder (Fisher Scientific, Ottawa, Ontario, Canada) following the addition of 800 μl of lysis buffer (1% sodium dodecyl sulphate, 10 mM Tris-HCl [pH 8.0], 0.5 M NaCl and 10 mM EDTA). Genomic DNA extraction was then performed according to the method of Sambrook et al. (1989) *Molecular Cloning: A Laboratory Manual*. Cold Spring Harbour Press, Cold Spring Harbour, N.Y. DNA was re-suspended in 100 μL of TE buffer (10 mM Tris-HCl [pH 8.0] and 1 mM EDTA) and quantified by spectrophotometry using a NanoDrop ND-1000™ (NanoDrop Technologies, Inc., Rockland, Del.). DNA was adjusted to 10 ng/μL via the addition of TE buffer and stored at −20° C. until required.

Genomic DNA from each isolate was amplified using the primer pair (SEQ. ID. NO: 2; SEQ. ID. NO: 3). The primers were synthesised by Invitrogen Life Technologies Inc. (Burlington, Ontario, Canada). PCR reactions were performed in a total volume of 25 μL comprising 0.5 μL of purified genomic DNA template (10 ng/μL), 1.25 μL of each primer (0.5 μM), 2.0 μL of dNTP mix (2 mM each of dATP, dCTP, dGTP and dTTP [New England Biolabs, Ltd., Pickering, Ontario, Canada]), 2.0 μL of $MgCl_2$ (25 mM), 0.3 μL of Taq DNA polymerase (5 U/μL [Promega Corporation, Madison, Wis.]) and 2.5 μL of 10×PCR reaction buffer (50 mM Tris-HCl [pH 8.0], 100 mM NaCl, 0.1 mM EDTA, 1 mM DTT, 50% glycerol and 1% Triton X-100). The reaction was performed with an initial denaturation of 3 min at 94° C. followed by 35 cycles of denaturation (60 seconds at 94° C.), annealing (60 seconds at 60° C.) and extension (90 seconds at 72° C.), and a final extension of 10 minutes at 72° C.

6.8 Electrophoresis and Visualisation of PCR Products

PCR reactions were performed in an Alpha Units™ Block Assembly for PTC DNA Engine™ Systems(MJ Research Inc., Waltham, Mass.). PCR products were separated by electrophoresis on 2% agarose containing 1× Tris acetate-EDTA. Gels were run at 100V for 3 hours, and then stained with 1.0 µg/mL ethidium bromide for 15-20 minutes before being visualized and photographed under UV light. All PCR amplifications were performed in duplicate for purposes of reproducibility.

FIG. 13 shows that PCR amplification with the primer pair (SEQ. ID. NO: 2; SEQ. ID. NO: 3) resulted in the amplification of a single DNA fragment that migrated between the 0.8 and 1.2 kb length markers for each of 14 shown to exhibit weed control activity (see Example 2.2). These 14 isolates included all isolates of the present invention (Saskatoon Research Centre (SRC) collection and labelled with prefix SRC) as well as isolates SRC02-2A and SRC03-1A8 also from the Saskatoon Research Centre collection, and one other isolate, DAOM175940 (CCFC003534), obtained from the Department of Agriculture Ottawa Mycology (DAOM), also known as the Canadian Collection of Fungal Cultures (CCFC). DAOM175940 was collected independently of the SRC isolates, almost 20 years prior to the commencement of this project (see Table 5). A virulent isolate SRC94-26Avir, which was created in the laboratory rather than being isolated in nature did not produce a single DNA fragment that migrated between the 0.8 and 1.2 kb length markers as with the nature isolates originating from Canada thistle.

Apart from one other faint amplification product in lane 41 corresponding to isolate IMI175661 (see FIG. 13B), which upon re-amplification failed to yield a positive response (FIG. 13C, Lane 22), PCR amplification with the primer pair (SEQ. ID. NO: 2; SEQ. ID. NO: 3) did not result in amplification of products from genomic DNA of any of the other P. macrostoma isolates.

For re-analysis of the only suspect isolate, IMI175661, DNA from this isolate and one located on either side (i.e. lanes 40 and 42 of FIG. 13B, IMI118020 and IMI299239 respectively), were re-amplified. The latter two isolates were re-amplified to ensure that the product observed in FIG. 13B, Lane 41 did not originate from either of the flanking isolates by way of overflow or seepage of small amounts of DNA either during the loading process or by way of error. Additionally, as lane boundaries were occasionally difficult to distinguish, the inclusion of these two isolates ensured the problem was addressed adequately. Following re-amplification, all ensuing responses from these isolates were negative (FIG. 13C, Lanes 21-23).

Figure 13A:
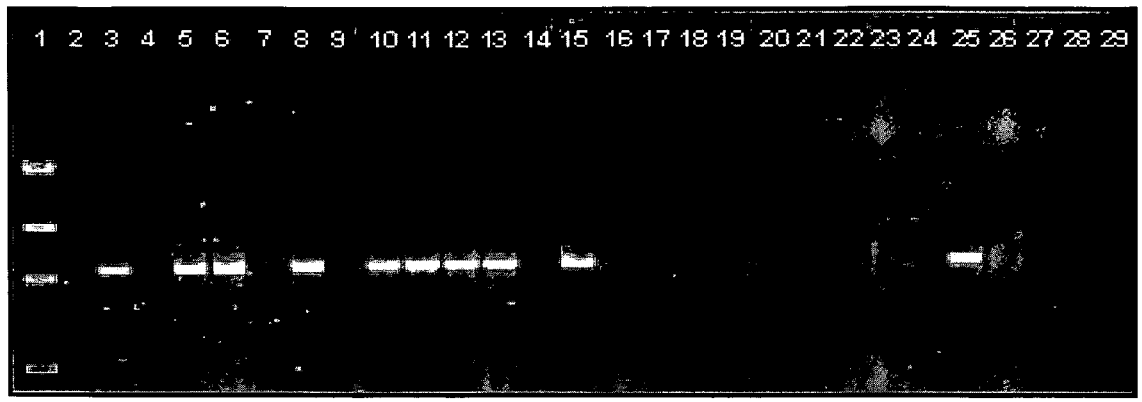
Figure 13B:
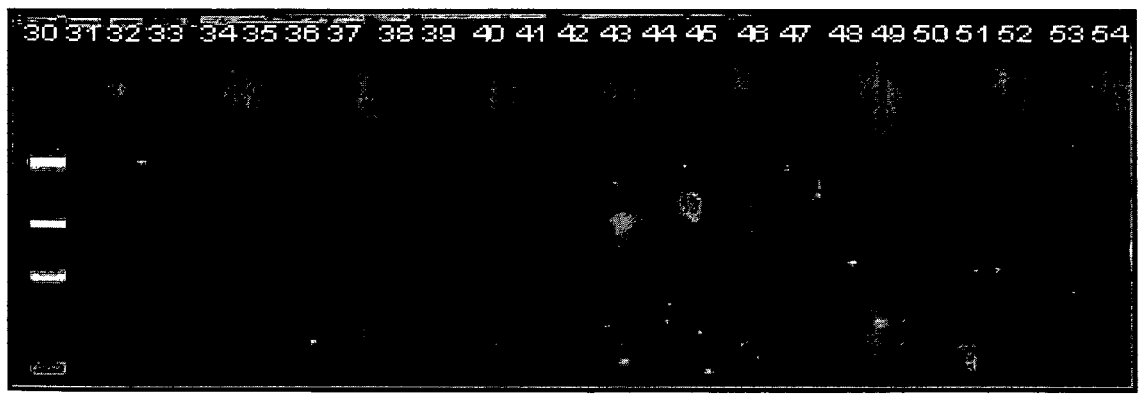
Figure 13C:

In contrast, three of the SRC isolates failed to amplify in the first round of experiments, despite being expected to yield amplification products (FIG. 13A). SRC97-15B2, SRC85-24B and SRC95-54A1, were re-amplified after adjusting DNA concentrations (FIG. 13C). With the exception of isolate SRC97-15B2, all returned positive responses.

Figure 13D:
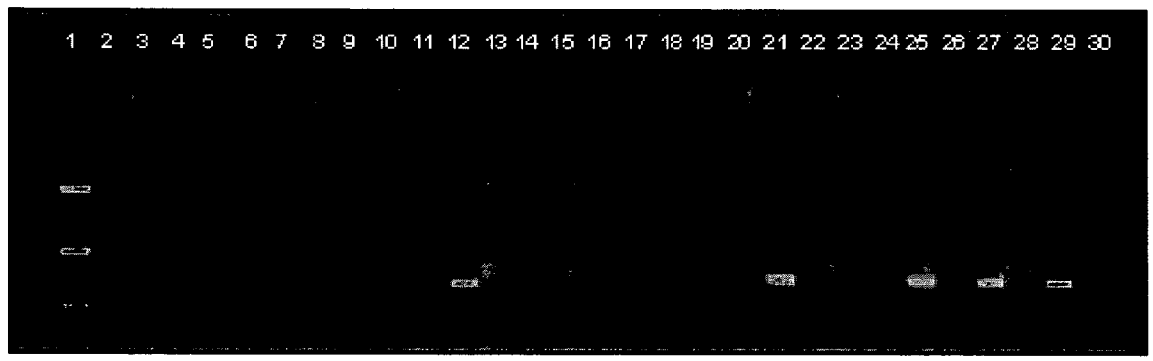

Morphological examination suggested that the culture of SRC97-15B was contaminated so it was resuscitated from stock cultures and DNA extracted for re-analysis after which a positive response was observed (FIG. 13D, Lane 12). Other isolates not previously tested were included in the analysis shown in FIG. 13D: SRC03-1A8 (see Table 5), P. macrostoma type cultures CBS223.69 and CBS529.66, and several other isolates of unknown Phoma sp. that are not part of the P. macrostoma collection presented in Table 5. Note that the avirulent isolate SRC94-26Avir was consistently negative.

These results demonstrate that the probe defined by SEQ ID NO:1 may be used to distinguish and identify fungal isolates that exhibit weed control activity. Furthermore, fragments of SEQ ID NO:1 may also be used to identify fungal isolates that exhibit weed control activity

EXAMPLE 7

Chromosomal Karyotyping of Bioherbicidal Isolates of *Phoma macrostoma*

7.1 Pulse Field Gel Electrophoresis Methods

The chromosomal DNA of bioherbicidal isolates of P. macrostomal (including the isolates of the present invention), together with one isolate of P. medicaginis and three isolates of P. herbarum, was compared by pulsed field gel electrophoresis (PFGE) analysis Single-spore cultures of the isolates were maintained by subculture on 10% V8®-juice agar and incubated at room temperature (20-24C) with a 16 hour photoperiod at 100-150 µE/m$^2$/s. Pycnidiospores of 14 day-old cultures were harvested by scraping the surface with 0.05% Tween 80, and filtering the spore suspension through two layers of Miracloth. Chromosome inserts were prepared as described by Plummer and Howlett (1993); *Curr Genet* 24: 107-113. Electrokaryotyping was performed on a contour-clamped homogeneous electric field (CHEF) DR II system (Bio-Rad, Mississauga, Ont., Canada) using 0.5×TBE buffer at 11C according to Chen and Séguin-Swartz (1999); *Can J Plant Pathol* 21: 361-367 with minor modifications as follows: the initial switch time was 600 sec and final switch time was 600 sec at 100 V for 72 hours, followed by initial 400 sec and final 400 sec at 100 V for 46 hours. Gels were stained in 0.1 µg/ml ethidium bromide solution and photographed. The chromosomal DNA bands were recorded for each isolate as present ("1") or absent ("0"). The data were analyzed by the phylogenetic software package TREECON® for Windows (Version 1.3b; Van de Peer and De Wachter (1994) *Computational Applications in the Biosciences*, 10: 569-570). The evolutionary distance estimation was performed according to Nei and Li (1979) *Proceedings of the National Academy of Sciences of the United States of America*, 76: 5269-5273. An unweighted pair group cluster method with arithmetic averages (UPGMA; Benzécri JP (1973) L'analyse des données. Tome I. La taxonomie. Dunod (ed), Paris, France) was used to infer tree topology. Bootstrap analyses were included in the distance estimation and tree topology to place confidence intervals on phylogenies (Efron and Gong (1983) *Am Stat* 37: 36-48.; Felsenstein (1985) Evolution, 39: 783-791; Sworfford et al. (1996) Hillis D M, Moritz C, Mable B K, eds. Molecular Systematics. Sinauer Associates, Sunderland, USA. pp. 407-514).

7.2 Results of PFGE Analysis

Twenty-seven polymorphic chromosomal DNA bands were generated using the PGFE analysis as shown in FIG. 14. The chromosomal profiles of P. medicaginis and P. herbarum were different from those of P. macrostoma. The bioherbicidal isolates of P. macrostoma separated into two different categories of chromosomal profiles (Type I and Type II). The Type I category included the isolates 94-44B, 85-24B, 94-26, 95-268B and 95-54A1, while the other five isolates (94-134, 94-359A, 97-12B, 97-15B2, 89-25A2) belonged to Type II as shown in FIG. 15.

EXAMPLE 8

RAPD Fingerprints of Bioherbicidal Isolates of *Phoma macrostoma*

8.1 Random Amplified Polymorphic DNA Methods

Random Amplification of DNA from bioherbicidal isolates (including isolates of the present invention) where compared with other *Phoma* isolates shown in Table 36. The primers used were 10-mer oligonucleotides purchased from the Biotechnology Laboratory (University of British Columbia (UBC), Vancouver, British Columbia) and are listed in Table 37.

TABLE 37

10-mer oligonucleotide primers selected for RAPD analyses

| Primer No. | Sequence | GC % | Source | SEQ. ID. NO: |
|---|---|---|---|---|
| UBC 308 | 5' AGCGGCTAGG 3' | 70 | UBC | 4 |
| UBC 356 | 5' GCGGCCCTCT 3' | 80 | UBC | 5 |
| UBC 734 | 5' GGAGAGGGAG 3' | 70 | UBC | 6 |
| UBC 736 | 5' GAGGGAGGAG 3' | 70 | UBC | 7 |

DNA amplification was performed in 25 μl reaction mixtures, each containing 20 ng template DNA, 1 unit AmpliTaq Gold Polymerase (5U/μl, Applied Biosystems), 1/10 volume (2.5 μl) of GeneAmp® 10×PCR Buffer II, 2.0 mM $MgCl_2$, 0.2 μM primer, and 100 μM of each dNTPs (MBI Fermentas). The PCR program comprised an initial denaturation at 94C for 10 min, followed by 45 cycles of 94C for 1 min (denaturation), 35C for 1 min (annealing) and 72C for 2 min (extension), followed by a final extension at 72C for 10 min. All the amplification reactions were performed in an Alpha Unit™ Block Assembly for PTC DNA Engine™ Systems (MJ Research, Inc.). The amplification products were resolved by electrophoresis on 1.5% agarose gels. To check reproducibility of amplicons, amplifications were conducted in duplicate. Banding patterns were identical in both trials, signifying reproducability.

The chromosomal DNA bands were recorded for each *Phoma* isolate as present ("1") or absent ("0"). The data were analyzed by the phylogenetic software package TREECON® for Windows (Version 1.3b; Van de Peer and De Wachter (1994) *Computational Applications in the Biosciences,* 10: 569-570). The evolutionary distance estimation was performed according to Nei and Li (1979) *Proceedings of the National Academy of Sciences of the United States of America,* 76: 5269-5273. An unweighted pair group cluster method with arithmetic averages (UPGMA; Benzécri JP (1973) L'analyse des données. Tome I. La taxonomie. Dunod (ed), Paris, France) was used to infer tree topology. Bootstrap analyses were included in the distance estimation and tree topology to place confidence intervals on phylogenies (Efron and Gong (1983) *Am Stat* 37: 36-48.; Felsenstein (1985) *Evolution,* 39: 783-791; Sworfford et al. (1996) Hillis D M, Moritz C, Mable B K, eds. Molecular Systematics. Sinauer Associates, Sunderland, USA. pp. 407-514).

8.2 Results of RAPD Fingerprinting

The RAPD fragment patterns from the biocontrol isolates with primers UBC 308, UBC 356, UBC 734 and UBC 736 were similar to each other but different from those of other isolates of *P. macrostoma* var. *macrostoma, P. macrostoma* var. *incolorata*, and other species of *Phoma* as shown in FIGS. 16A-D. All 10 biocontrol isolates of the present invention were closely related and clustered within the group designated "*P. macrostoma* Biocontrol Isolates" shown in FIG. 17. To a limited extent the isolates within this group were somewhat variable from each other. For example, 97-15B2 had a slightly different banding pattern than the other biocontrol isolates using primers UBC 356, UBC 734 and UBC 736. Isolate 95-54A1 also had an extra band with Primer UBC 736.

The biocontrol isolates of the present invention were clustered together and genetically distinct from the other *Phoma* isolates. Within the cluster of biocontrol isolates, the isolates originating from two different Canadian ecozones were randomly scattered. The evolutionary distance scale was placed at top of figure and a bootstrap value was presented on each node of the tree. With the exception of a small group basal to the tree, which was only supported by 59% of bootstrap replicates, strong statistical support was evident for all major clusters.

EXAMPLE 9

ITS Sequencing of Bioherbicidal Isolates of *Phoma macrostoma*

The ribosomal DNA region located between the small (18S) and large ribosomal subunits (LSU) contains two rapidly evolving sequences, referred to as the internal transcribed spacer (ITS) 1 and 2. These rapidly evolving sequences, which are separated by the highly conserved 5.8S ribosomal RNA gene, are capable of displaying variation at the species level. Because these sequences represent the largest components of sequence databases and are easily amplified using universal primers (White et al. (1990) *PCR Protocols: A Guide to Methods and Applications*, eds. Innis, M. A., Gelfand, D. H., Sninsky, J. J., White, T. J. Academic Press, Inc., New York; pp.315-322), sequence analysis of this region can provide a useful tool for identification of species and delineation of species boundaries. Additionally, ITS sequencing may provide a useful tool to assess the relatedness of isolates prior to population studies or genetic diversity analysis. Regions within the ITS sequence may also be identified that are unique to *Phoma macrostoma* isolates exhibiting weed control activity, and these regions may be used to assay for isolates exhibiting weed control activity using standard techniques including PCR, or SNP analysis.

9.1 Fungal Isolates and DNA Extraction

All details regarding collection, resuscitation, cultivation, storage and extraction of fungal DNA are as described previously in Example 6.7. The isolates used are listed in Table 5.

9.2 ITS PCR Amplification

The complete ITS region (ITS1, 5.8S rRNA gene, ITS2) of each isolate was amplified with primers:

```
ITS4
(TCC TCC GCT TAT TGA TAT GC; SEQ. ID. NO: 8) and

ITS5
(GGA AGT AAA AGT CGT AAC AAG G; SEQ. ID. NO: 9)
``` designed by White et al. (1990) *PCR Protocols: A Guide to Methods and Applications*, eds. Innis, M. A., Gelfand, D. H., Sninsky, J. J., White, T. J. Academic Press, Inc., New York; pp. 315-322, and synthesized by Integrated DNA Technologies (Coralville, Iowa). PCR reactions were performed in a total volume of 25 µL comprising 0.5 µL of purified genomic DNA template (10 ng/µL), 1.25 µL of each primer (5 µM), 2.0 µL of dNTP mix (2 mM each of dATP, dCTP, dGTP and dTTP [New England Biolabs]), 1.5 µL of MgCl$_2$ (25 mM), 0.3 µL of Taq DNA polymerase (5 U/µL [Promega Corporation]) and 2.5 µL of 10×PCR reaction buffer (50 mM Tris-HCl [pH 8.0], 100 mM NaCl, 0.1 mM EDTA, 1 mM DTT, 50% glycerol and 1% Triton X-100). The reaction was performed with an initial denaturation of 3 min at 94° C. followed by 35 cycles of denaturation (60 s at 94° C.), annealing (60 s at 65° C.) and extension (2 min at 72° C.), and a final extension of 10 min at 72° C. PCR reactions were performed in an Alpha Units™ Block Assembly for PTC DNA Engine™ Systems (MJ Research Inc., Waltham, Mass.).

Prior to purification and sequence analysis of amplified products, 5 µL aliquots from each isolate were separated and visualized by electrophoresis as described previously, to confirm that the amplification reactions had occurred successfully.

9.3 PCR Product Purification and DNA Sequencing

Following electrophoresis, ITS products were purified with the Wizard PCR Preps DNA Purification System™ (Promega Corporation). Sequencing of the purified PCR products was performed by the Plant Biotechnology Institute, Saskatoon, Saskatchewan, Canada. PCR products were sequenced in an AB 3730xl capillary electrophoresis DNA sequence analyzer (Applied Biosystems, Streetsville, Ontario, Canada), at the DNA Technologies Unit, Plant Biotechnology Institute, National Research Council of Canada, Saskatoon, SK, Canada.

9.4 Sequence Analysis

Following receipt of sequence data, primer sequences were removed and forward and reverse sequences were aligned, corrected visually for mismatches in accordance with supplied electropherograms and trimmed to include the complete ITS region (ITS1, 5.8S rRNA gene, ITS2) and 10 bases each of the 18S and large ribosomal RNA subunits, which were retained to aid in the alignment. Individual sequences were compiled in BioEdit Sequence Alignment Editor (Hall (1999) *Nucleic Acids Symposium Series,* 41: 95-98) and analyzed by ClustalX™ (Thompson et al. (1997) *Nucleic Acids Research,* 24: 4876-4882). A phylogenetic tree based on the neighbor-joining algorithm of Saitou & Nei (1987) *Molecular Biology and Evolution,* 4: 406-425 was produced to demonstrate the relationships between isolates. Statistical support for inferred groups was estimated by bootstrap analysis using 1000 replications (Felsenstein (1985) *Evolution,* 39: 783-791). The final tree was displayed with NJplot™ (Perriere & Gouy (1996) *Biochimie,* 78: 364-369).

9.5 Results

Figure 18A:
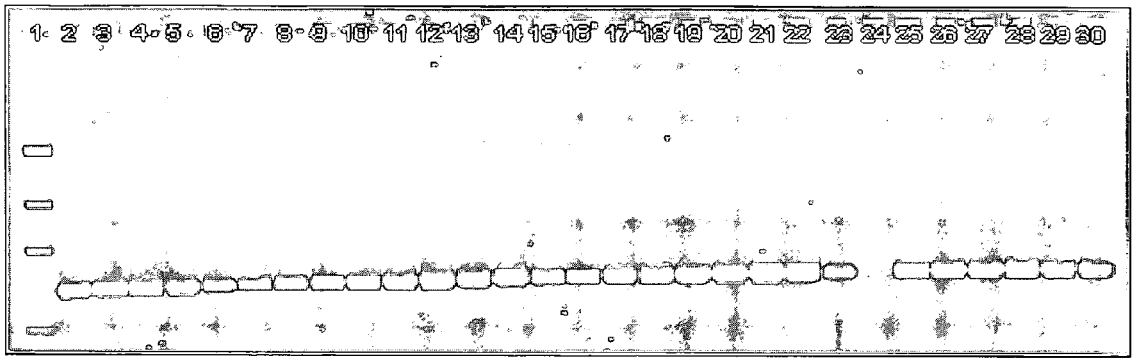
Figure 18B:
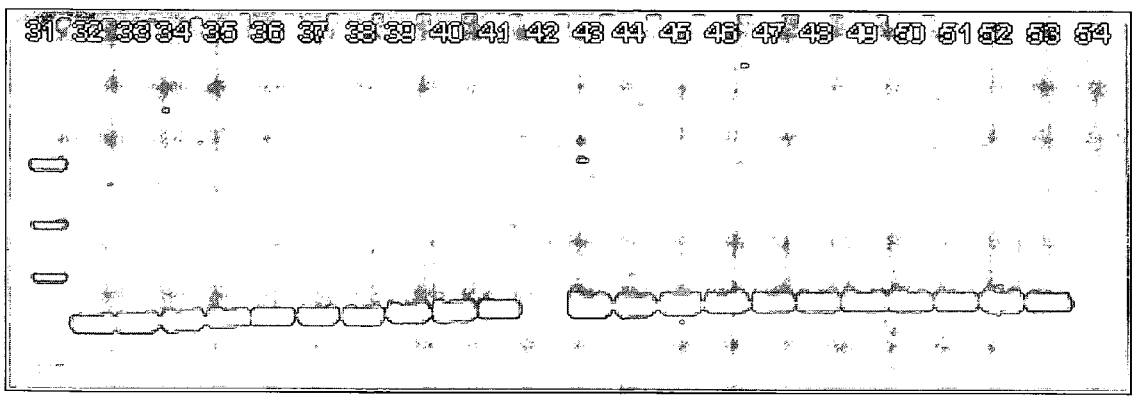
Figure 18C:
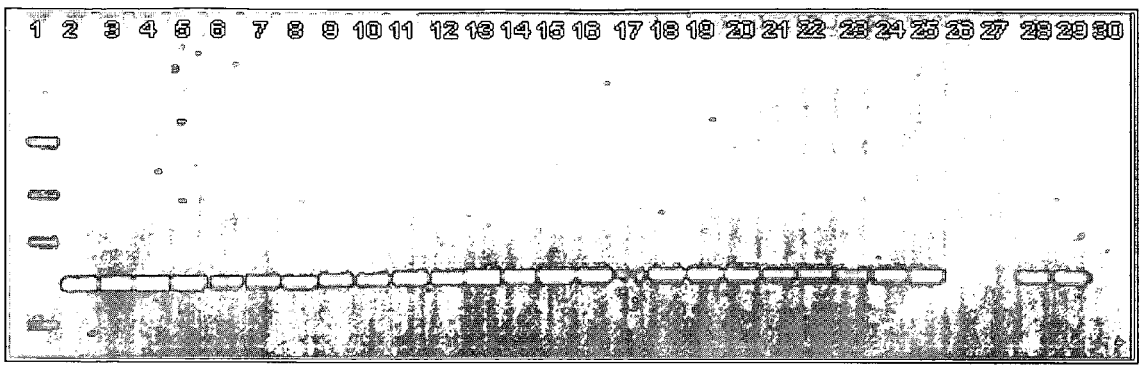
Figure 18D:
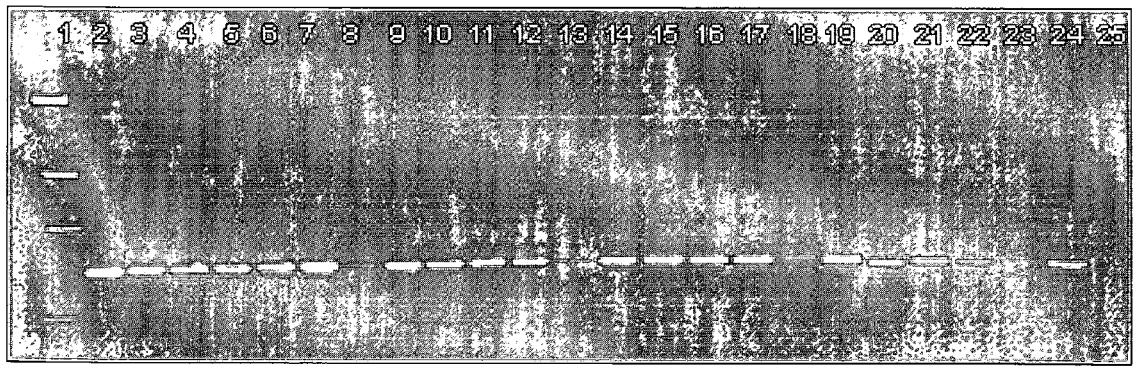

PCR amplification with oligonucleotide primers ITS4 and ITS5 (White et al. (1990) *PCR Protocols: A Guide to Methods and Applications,* eds. Innis, M. A., Gelfand, D. H., Sninsky, J. J., White, T. J. Academic Press, Inc., New York; pp. 315-322), resulted in the amplification of a single DNA fragment that migrated equidistance between the 400 and 800 bp length markers for each of the isolates sequenced in this study as shown in FIGS. 18A-D. Although some individual isolates failed to amplify during the first round of experiments, as indicated in FIGS. 18A and 18B, re-amplification with differing DNA concentrations and in the case of SRC97-15B2, resuscitation from stock as outlined in Example 6.8, solved these problems and DNA from each of the isolates in the collections was amplified to produce the expected fragment size of approximately 500 bp.

With the exception of isolate IMI336757, which was 516 bp in length due to an 8 base deletion at position 370-377, the length of the ITS region amplified from each isolate ranged from 521-524 nucleotides, following sequence analysis and subsequent removal of terminal primer sequences. This stretch included the entire ITS region (ITS1, 5.8S, ITS2), 43 bp of the 18S ribosomal DNA subunit and 39 bp of the large ribosomal DNA subunit. The ITS region alone spanned 439-442 bases, 125-128 for ITS1, 160 for the 5.8S region, which was completely conserved and 154 for ITS2. In general, intraspecific sequence variation between the majority of isolates was minimal. However, species originating from Canada thistle (*Cirsium arvense*) and of Canadian origin frequently displayed a common divergence from the other isolates in the study, generally comprising unique nucleotides at positions of variance.

Of the 524 bp sequenced, isolates shown to exhibit biocontrol activity (Example 2.2) including isolates from Canada thistle were unique at 20 positions throughout the sequence, 12 of which were present within the more variable ITS1 region. In this region, all instances of divergence were common to isolates from Canada thistle (SRC isolates including the isolates of the present invention, and DAOM175940) and on almost half of these occasions isolate DAOM175135, obtained from *Lens esculenta,* but also of Canadian origin shared the unique nucleotide. Although other isolates occasionally also shared a familiar divergence from a more common state, on average only 2.9 of the 47 non-Canada thistle isolates possessed the same nucleotide at these positions. Fourteen transitions, four transversions and two insertion (indels) mutations were responsible for the observed variation common to isolates from Canada thistle, which was equivalent to approximately 3.82% of the amplified region. FIG. 19A shows multiple sequence alignment of the ITS sequence for the *Phoma* isolates which provides a visual representation of the sequence compositions. A non-limiting example of an ITS sequence from a *Phoma macrostoma* isolate that exhibits weed control activity is shown in FIG. 19B (SEQ ID NO:15). Sequences of the other isolates that exhibit weed control activity can be derived from the information presented in FIG. 19A.

To study the relationship between isolates, a phylogenetic tree was produced according to the neighbor-joining method of Satou and Nei (1987) *Molecular Biology and Evolution,* 4: 406-425. Confidence values for the inferred groups were estimated by bootstrap analysis using 1000 random permutations (Felsenstein (1985) *Evolution,* 39: 783-791). The ITS phylogram shown in FIG. 20 indicates the presence of two major clusters. Group I comprised isolates from world collections, collected from numerous hosts and almost exclusively from locations external to Canada. Strain DAOM175135 was the only exception, having been isolated from *Lens esculenta* from Alberta, Canada. No isolates in this group had bioherbicidal activity. Group II contained isolates shown to exhibit biocontrol activity (Example 2.2) and was supported by 100% of bootstrap replications. Most of these isolates (including the isolates of the present invention) were isolated from Canada thistle. Many strains within their respective groups were identical throughout their entire ITS region, as shown by the absence of branch lengths. The long branch lengths observed for isolates obtained from Canada thistle (Group II), suggest that considerable time has passed since this group diverged from a common ancestor. The loss of virulence observed for isolate SRC94-26Avir (produced in the laboratory rather than being isolated from nature) also appears to be reflected by a divergence in the ITS region, away from isolates exhibiting the bioherbicidal phenotype.

EXAMPLE 10

AFLP Fingerprints of Bioherbicidal Isolates of *Phoma macrostoma*

The amplified fragment length polymorphism (AFLP) technique, developed by Vos et al. (1995) *Nucleic Acids Research,* 23: 4407-4414, is a powerful tool for DNA fingerprinting of fungal genomes. In principle, it is a combination of RFLP and PCR techniques. DNA is digested with two restriction enzymes (EcoRI and MseI in the original protocol), and double-stranded oligonucleotide adapters are ligated to the restriction sites. PCR primers complementary to the adapters and restriction sites amplify fragments that are flanked by the adapters. A subset of these fragments is selectively amplified by PCR primers that contain 2- or 3-base extensions into the restriction fragments. Only those fragments that perfectly match the primer sequences can be amplified by PCR. DNA fingerprints generally contain 50 to 100 restriction fragments after separation on denaturing polyacrylamide gel. AFLP are highly reproducible, easily implemented, required only small quantities of genomic DNA and exhibit a high level of polymorphisms per gel.

10.1 Fungal Isolates and DNA Extraction

All details regarding collection, resuscitation, cultivation, storage and extraction of fungal DNA are as described previously in Example 6.7. The isolates used are listed in Table 5.

10.2 Amplified Fragment Length Polymorphisms (AFLP)

AFLP protocols were adapted from those supplied by Invitrogen. A 250 ng sample of genomic DNA was double digested with 3.6 units of EcoRI and 3.5 units of MseI (New England Biolabs, Pickering, Ontario, Canada) and 7 μL of 5× restriction digest reaction in a final volume of 35 μL. Digests were incubated at 37° C. for 2 h, followed by 15 min at 70° C. Adapters were then ligated onto the restriction fragments and used as priming sites for subsequent PCR amplification. For this ligation, a 35 μL adapter/ligation mixture was added directly to the completed restriction digest reaction. The ligation reaction mixture contained 2 μmol EcoRI-adapter; 20 μmol MseI-adapter; 1.4 units T4 DNA-ligase (Invitrogen, Burlington, Ontario, Canada); 0.4 mM ATP; 10 mM Tris-HCl, pH 8.0; 10 mM MgAc; and 50 mM KAc. The ligation reaction was incubated at room temperature (20-25° C.) for 2 h and then diluted 10 fold with 1×TE-0.1 buffer (10 mM Tris-HCl [pH 8.0], 0.1 mM EDTA).

The pre-amplification reactions were performed using the restricted fragments with ligated adapters as template. Both the EcoRI and MseI primers were fully complementary to their respective adapters and contained no selective bases. The PCR 51 μL mix contained 5 μL template DNA (ligation product); 2 units Taq DNA polymerase (New England Biolabs); 200 mM Tris-HCl, 15 mM $MgCl_2$, 500 mM KCl, and 40 μL of pre-amplification primer mix (0.23 mM of each dNTP, 750 μg/L each of MseI and EcoRI primers and sterile water). The following conditions were used for PCR: 94° C. for 30 s, 56° C. for 60 s and 72° C. for 60s for 20 cycles. All pre-amplification reactions were run on an MJ Research PTC DNA Engine Systems thermal cycler™ (MJ Research, Waltham, Mass.). The pre-amplification product was diluted 50 fold with 1×TE-0.1 buffer.

Twenty-one primer combinations were used to perform a preliminary screening using three *P. macrostoma* isolates. Primer combinations included EcoRI+AC, AG, AT, TA, TC, TG or TT combined with MseI+CA, CT, or G. With the exception of primer combinations containing EcoRI+TG, all produced amplification products. Fifteen primer combinations were used to fingerprint the entire population of isolates. Six primer combinations; EcoRI+AC, AG, TC with MseI+CA and CT were selected for analysis (Table 38). For each primer pair the EcoRI primer was end-labeled with radioactive $\gamma^{-33}$P-ATP. The end labelling reaction mixture contained: 27.8 mg/L EcoRI primer, 0.2 units of T4 kinase (Invitrogen), and 0.10 μL of 5× kinase buffer, in a total of 0.5 μL. The end labelling reaction was incubated for 1 hour at 37° C. followed by 10 minutes at 70° C.

TABLE 38

Primer pairing and sequences for primer combinations used in AFLP

| Primer pairings | Sequences | SEQ. ID. NO: |
|---|---|---|
| EcoRI + AC and MseI + CA | 5'-GACTGCGTACCAATTCAC-3' + <br> 5'-GATGAGTCCTGAGTAACA-3' | 10 <br> 11 |
| EcoRI + AC and MseI + CT | 5'-GACTGCGTACCAATTCAC-3' + <br> 5'-GATGAGTCCTGAGTAACT-3' | 10 <br> 12 |
| EcoRI + AG and MseI + CA | 5'-GACTGCGTACCAATTCAG-3' + <br> 5'-GATGAGTCCTGAGTAACA-3' | 13 <br> 11 |
| EcoRI + AG and MseI + CT | 5'-GACTGCGTACCAATTCAG-3' + <br> 5'-GATGAGTCCTGAGTAACT-3' | 13 <br> 12 |
| EcoRI + TC and MseI + CA | 5'-GACTGCGTACCAATTCTC-3' + <br> 5'-GATGAGTCCTGAGTAACA-3' | 14 <br> 11 |
| EcoRI + TC and MseI + CT | 5'-GACTGCGTACCAATTCTC-3' + <br> 5'-GATGAGTCCTGAGTAACT-3' | 14 <br> 12 |

Selective primers are shown in bold type

For selective amplifications a selective amplification mixture containing 6.7 mg/L MseI primer (with either -CA or -CT extension) and 267 μmol of each dNTP per reaction, 2 units of Taq DNA polymerase (New England Biolabs), 2 μL of 10×PCR buffer (200 mM Tris-HCl, pH 8.0; 15 mM $MgCl_2$; 500 mM KCl), sterile water and 15 μL of the 1:50 pre-amplification product as template was combined with end labeled EcoRI primer mix. PCR reactions were performed on an MJ Research PTC DNA Engine Systems thermal cycler (MJ Research), under the following conditions: one cycle at 94° C. for 30 s, 65° C. for 30 s and 72° C. for 60 s; during the next 12 cycles the annealing temperature was decreased by 0.7° C. per cycle; and the final 23 cycles were performed at 94° C. for 30 s, 56° C. for 30 s and 72° C. for 60 s.

10.3 Electrophoresis and Visualization of AFLP Products

Amplification products were subjected to electrophoresis on 5% denaturing polyacrylamide gels on a BioRad sequencing gel system (38 cm×50 cm×0.4 cm). Gels were run at 90 W for 2.45 h in 1×TBE, blotted dry with Whatmann 3 MM chromatography paper and dried on a BioRad 585 gel drier with BioRad Hydrotech vacuum pump for 2 h, then exposed to Kodak Biomax™ (location) 35 cm×43 cm X-ray film for 5-7 days at −80° C. Film was developed using Kodak XOMAT™ film developer.

10.4 Data Analysis

PCR products were analyzed using visual pair-wise comparisons of adjacent lanes by reading horizontally across the gel from the bottom to the top. Only bright definitive bands between 100 and 400 bp were scored and the presence of single, dominant bands in each lane allowed alignment of PCR products across non-contiguous lanes. Polymorphic DNA fragments were treated as individual loci, which were named according to the primer used and the length of the informative DNA fragment amplified. All amplicons were scored under the assumption that each fragment represented a unique biallelic (presence or absence of a fragment) locus. Data from all six primer combinations (Table 38) were combined to produce a multilocus dataset. Isolates with the same DNA fingerprint and multilocus haplotype are assumed to be individual members of the same clone.

Data was analyzed using TREECON v1.3b; (Van de Peer & De Wachter (1994) *Computational Applications in the Biosciences,* 10: 569-570). A distance matrix was constructed according to Nei and Li (1979) *Proceedings of the National Academy of Sciences of the United States of America,* 76: 5269-5273 and a dendrogram produced via the un-weighted pair-group method with arithmetic means (UPGMA; Sneath & Sokal (1973) Numerical Taxonomy. W. H. Freeman, San Francisco). Confidence for inferred clusters was provided by bootstrap analysis using 1000 permutations (Felsenstein (1985) *Evolution,* 39: 783-791).

10.5 Results

AFLP analysis of genomic DNA from isolates *P. macrostoma* with six primer combinations (Table 38) resulted in the production of 697 polymorphic bands following the removal of bands outside the 100-400 bp region and combination of all primer sets into a multilocus dataset. Due to the diversity of isolates, no single band was present in all isolates and FIG. 21 demonstrates the complexity of fingerprints across the collection of isolates. Prior to clustering analysis two distinct fingerprints were apparent, and a large number of the isolates fell into one of these two groups.

One group comprises a large number of isolates from a number of collections including ATCC, CBS, ICMP, DAOM and IMI. This group is readily identified and comprises isolates ATCC24524, CBS112.36, CBS154.83, CBS185.25, CBS198.69, CBS297.36, CBS482.95, CBS483.66, CBS488.94, CBS560.70, CBS598.94, CBS837.84, CBS839.84, DAOM175951, CCM-F322, CCMF-323, ICMP2325, ICMP3173, ICMP6603. ICMP6628, ICMP6803, ICMP7033, ICMP10963, ICMP11186, IMI118020, IMI175661 and IMI299239 which correspond to lanes 6, 8, 10-20, 23-26, 28-31, 33, 35-36, 38-40 and also includes isolates MA1908B, CBS223.69, CBS345.97, CBS371.61, CBS529.66 and MA3312 which are not shown on this gel.

The second group contains isolates DAOM175940, SRC85-24B, SRC89-25A2, SRC94-26, SRC94-44B, SRC94-134, SRC94-359A, SRC95-54A1, SRC95-54A2 and SRC95-268B which correspond to lanes 22, 44-46, 48-53 and also include isolates SRC97-12B, SRC97-15B, SRC02-2A and SRC03-1A8 which are not shown on this gel but exhibit a similar band-profile. These isolates exhibit weed control activity. Therefore, this analysis may be used to screen or select for *Phoma macrostoma* isolates that exhibit weed control activity.

The remaining isolates in FIG. 21, which are not representative of either group all possess unique DNA fingerprints and have unique genotypes. This broad range of genotypes suggests there is considerable diversity amongst the world collection. These isolates include ATCC46580, CBS115.12, DAOM175135, ICMP2715, ICMP6814, ICMP10843, ICMP12948, IMI336757, IMI336761 and WAC7881 which correspond to lanes 7, 9, 21, 27, 32, 34 and 41-43, and also include isolates WAC7788, IMI192267, IMI192268 and CBS300.36 which are not shown on this gel. Isolate SRC94-26Avir (lane 47) has a completely different fingerprint in comparison to the other SRC isolates, and appears to have more in common with the non-bioherbicidal *P. macrostoma* isolates than the other isolates obtained from Canada thistle exhibiting herbicidal activity.

The UPMGA cluster analysis produced a dendrogram which is shown in FIG. 22. Almost every isolate occupied a single branch. Notable exceptions were those isolates from Canada thistle which comprised a monophyletic cluster towards the basal part of the tree. This cluster was supported by 100% of bootstrap replications and contained branches that split the SRC isolates into two smaller groups that corresponded to chromosome karyotype groupings as reported in Section 7.2. Isolate DAOM175940 and SRC03-1A8 isolate corresponded to those isolates previously identified as group I by chromosomal karyotyping (SRC85-24B, SRC94-26, SRC94-44B, SRC95-54A1, SRC95-54A2, SRC95-268B), while the remainder of the isolates including isolate SRC02-2A (which was not part of the original chromosomal karyotyping study) clustered together and corresponded to isolates previously identified as possessing the group II chromosome karyotype (SRC89-25A2, SRC94-134, SRC94-359A, SRC97-12B, SRC97-15B2). These clusters were supported by 91 and 82% of bootstrap replicates, respectively.

The branch containing this unique subset of isolates with bioherbicidal activity, identified for their reaction to the biocontrol specific primers, unique ITS sequence and unique AFLP fingerprint is embedded within the dendrogram suggesting that the diversity within this group of isolates is no greater than that within the entire collection. In addition to being genetically unique from the rest of the collection these isolates are also genetically more similar than any other isolates in the study. They possess a very narrow range of diversity and have almost identical genotypes. The data suggest that these isolates may have become genetically isolated on their respective host Canada thistle and/or geographically isolated in Canada. These traits identify biocontrol isolates as a unique subset, possessing unique characteristics.

Note, all reference made to isolates from Canada thistle are made with the exception of isolate 96-24Avir. This avirulent isolate was created by hyphal tip transfer in the laboratory and does not possess herbicidal traits. Primer-mediated identification, ITS sequence analysis and AFLP fingerprinting indicate that this isolate is unlike the other SRC isolates and DAOM175940 that possess the unique characteristics implicated in bioherbicidal activity against broadleaf weeds.

All citations are hereby incorporated by reference.

The present invention has been described with regard to one or more embodiments. However, it will be apparent to persons skilled in the art that a number of variations and modifications can be made without departing from the scope of the invention as defined in the claims.

What is claimed is:

1. An isolated *Phoma macrostoma* isolate from Canadian thistle characterized as exhibiting weed control activity and having an amplified fragment length polymorphism (AFLP) as disclosed in FIG. 21, lanes 22, 44-46, and 48-53 using the primer pair SEQ. ID. NO: 10 and SEQ. ID. NO: 12 or the primer pair SEQ. ID. NO: 10 and SEQ. ID. NO: 11.

2. The isolated *P. macrostoma* isolate of claim 1, wherein the isolate is selected from the group consisting of:

a) 85-24B (IDAC 230201-1, deposited Feb. 23, 2001), b) 89-25A (IDAC 110401-1, deposited Apr. 11, 2001), c) 94-26 (IDAC 230201-2, deposited Feb. 23, 2001), d) 94-44B (IDAC 230201-3, deposited Feb. 23, 2001)

e) 94-134 (IDAC 230201-4, deposited Feb. 23, 2001), f) 94-359A (IDAC 110401-2, deposited Apr. 11, 2001), g) 95-54A1 (IDAC 230201-5, deposited Feb. 23, 2001), h) 95-268B (IDAC 110401-3, deposited Apr. 11, 2001), i) 97-12B (IDAC 230201-6, deposited Feb. 23, 2001), j) 97-15B2 (IDAC 110401-4, deposited Apr. 11, 2001).

3. The isolated *P. macrostoma* isolate of claim 1 combined with a medium for supporting viability of said one or more than one *Phoma* isolate.

4. The isolated *P. macrostoma* isolate of claim 2 combined with a medium for supporting viability of said one or more than one *Phoma* isolate.

* * * * *

SEQUENCE LISTING

<160> NUMBER OF SEQ ID NOS: 17

<210> SEQ ID NO 1
<211> LENGTH: 1376
<212> TYPE: DNA
<213> ORGANISM: Artificial Sequence
<220> FEATURE:
<223> OTHER INFORMATION: Synthetic probe with KpnI and SacI Sites

<400> SEQUENCE: 1

```
ggtaccgatc cccgcaatac accacgattc tggatgcgac aggcaagatt atcgcacctg      60
gattcgtcga cactcaccgt catggttggc aaacgttttt taagaccatg gtctcaaaca     120
tcactctgat tgagtatttc ggccgtttcg gggagtcagc ttctgcagga cgcatcaatg     180
ctgagcaagt ataccttggt cagctcgccg gcctctatga atcagtgaac acgggagtca     240
ctacgaccgt tgatcacgcc catcacactt ggtcagatga gacgtcctgg gctggtctaa     300
acgccagtat agacagcggt gcgcgcgtgt tctggtctta caccttccat gaagttgcaa     360
actataccat cgagcagcaa ctccaaaact atcgcgacat tgtgagccgc gccccacagg     420
caggatcggc tgctgagatc ggagttgctt tcgacagctt cgacaatggc tctgttgatc     480
tggacactat cactgcgatc atagacttag ctaagtaagt ttactcgtta ctcaccttat     540
gattcaaggt atacattgtt ttagttagtc taacgttgtg tgtttagaga atcaaatgcc     600
tcggttatca caacccacgg tggaggaggt gtctatggaa gtaggtgacc cgatgtcctt     660
ttgttttgtt tgagaccgca ctcttgaaca atgggaactg accaaaatct gcagacgaca     720
attctccttc gaccctacag tcccttggca ttctcaacac aagcattcct gtcgttatct     780
ctcacgcgac gtacgtgact ttgcgggaca caatgctgtt gcgcgagaca aatcagttcg     840
tttctatcac gcccgagtca gagatggggt tcggcctcgg acggccgacg agcaacatga     900
tcattgacca agcctcctta ggtgttgatt cacacgcctt tgcttctagt gatctagtat     960
cccaggcgcg cttgtttctt cagagtacgc ggtcagcagt caccgatcaa ctcttcaaga    1020
aatggcaggc tcctaagtcg aaccctatga gtgtcgttca ggcttttctc cttagcacac    1080
gtaacggagg ccttgcactt cgccgcccag accttggtgt tctcagtgtc ggcgctaaag    1140
ctgacgttgt ggtgtgggac gggaccagtc cgagcctgct gggctggcgt gatcctgtgg    1200
ccgcaatcat ccagcactcc aatgtcggcg atgttgagca tgttctcatc gatggcaaat    1260
ttgtgaaaag agatcacaag ctggttgttg gaactacgc gaatgtaaag tctcggttcc    1320
tggaagtcgc aaaccgcatc caggaggact gggagctgat ccccgtccc gagctc        1376
```

<210> SEQ ID NO 2
<211> LENGTH: 20
<212> TYPE: DNA
<213> ORGANISM: Artificial Sequence
<220> FEATURE:
<223> OTHER INFORMATION: Synthetic left primer

<400> SEQUENCE: 2

-continued acagcttcga caatggctct                                       20

<210> SEQ ID NO 3
<211> LENGTH: 20
<212> TYPE: DNA
<213> ORGANISM: Artificial Sequence
<220> FEATURE:
<223> OTHER INFORMATION: Synthetic right primer

<400> SEQUENCE: 3
acattcgcgt agttcccaac                                       20

<210> SEQ ID NO 4
<211> LENGTH: 10
<212> TYPE: DNA
<213> ORGANISM: Artificial Sequence
<220> FEATURE:
<223> OTHER INFORMATION: Synthetic primer UBC 308

<400> SEQUENCE: 4
agcggctagg                                                  10

<210> SEQ ID NO 5
<211> LENGTH: 10
<212> TYPE: DNA
<213> ORGANISM: Artificial Sequence
<220> FEATURE:
<223> OTHER INFORMATION: Synthetic primer UBC 356

<400> SEQUENCE: 5
gcggccctct                                                  10

<210> SEQ ID NO 6
<211> LENGTH: 10
<212> TYPE: DNA
<213> ORGANISM: Artificial Sequence
<220> FEATURE:
<223> OTHER INFORMATION: Synthetic primer UBC 734

<400> SEQUENCE: 6
ggagagggag                                                  10

<210> SEQ ID NO 7
<211> LENGTH: 10
<212> TYPE: DNA
<213> ORGANISM: Artificial Sequence
<220> FEATURE:
<223> OTHER INFORMATION: Synthetic primer UBC 736

<400> SEQUENCE: 7
gagggaggag                                                  10

<210> SEQ ID NO 8
<211> LENGTH: 20
<212> TYPE: DNA
<213> ORGANISM: Artificial Sequence
<220> FEATURE:
<223> OTHER INFORMATION: Synthetic primer ITS4

<400> SEQUENCE: 8
tcctccgctt attgatatgc                                       20

<210> SEQ ID NO 9
<211> LENGTH: 22
<212> TYPE: DNA
<213> ORGANISM: Artificial Sequence

```
<220> FEATURE:
<223> OTHER INFORMATION: Synthetic primer ITS5

<400> SEQUENCE: 9
ggaagtaaaa gtcgtaacaa gg                                              22

<210> SEQ ID NO 10
<211> LENGTH: 18
<212> TYPE: DNA
<213> ORGANISM: Artificial Sequence
<220> FEATURE:
<223> OTHER INFORMATION: Synthetic primer

<400> SEQUENCE: 10
gactgcgtac caattcac                                                   18

<210> SEQ ID NO 11
<211> LENGTH: 18
<212> TYPE: DNA
<213> ORGANISM: Artificial Sequence
<220> FEATURE:
<223> OTHER INFORMATION: Synthetic primer

<400> SEQUENCE: 11
gatgagtcct gagtaaca                                                   18

<210> SEQ ID NO 12
<211> LENGTH: 18
<212> TYPE: DNA
<213> ORGANISM: Artificial Sequence
<220> FEATURE:
<223> OTHER INFORMATION: Synthetic primer

<400> SEQUENCE: 12
gatgagtcct gagtaact                                                   18

<210> SEQ ID NO 13
<211> LENGTH: 18
<212> TYPE: DNA
<213> ORGANISM: Artificial Sequence
<220> FEATURE:
<223> OTHER INFORMATION: Synthetic primer

<400> SEQUENCE: 13
gactgcgtac caattcag                                                   18

<210> SEQ ID NO 14
<211> LENGTH: 18
<212> TYPE: DNA
<213> ORGANISM: Artificial Sequence
<220> FEATURE:
<223> OTHER INFORMATION: Synthetic primer

<400> SEQUENCE: 14
gactgcgtac caattctc                                                   18

<210> SEQ ID NO 15
<211> LENGTH: 524
<212> TYPE: DNA
<213> ORGANISM: Phoma macrostoma

<400> SEQUENCE: 15
tttccgtagg tgaacctgcg gaaggatcat tacctagagt tgcgggctct gcctgccatc     60
tcttacccat gtcttttgag taccttacgt ttcctcggcg ggtccgcccg ccgactggac    120
```

```
aaacttaaac cacttgcagt tgaaatcagc gtctgaaaaa acttaatagt tacaactttc    180
aacaacggat ctcttggttc tggcatcgat gaagaacgca gcgaaatgcg ataagtagtg    240
tgaattgcag aattcagtga atcatcgaat ctttgaacgc acattgcgcc ccttggtatt    300 ccatgggca tgcctgttcg agcgtcattt gtaccttcaa gccttgcttg gtgttgggtg     360
tttgtctcgc ctctgcgcgc agactcgcct caaaacaatt ggcagccggc gtattgattt    420
cggagcgcag tacatctcgc gctttgcact caccacggcg gcgtccaaaa gtacattttt    480
acactcttga cctcggatca ggtagggata cccgctgaac ttaa                     524
```

<210> SEQ ID NO 16
<211> LENGTH: 1370
<212> TYPE: DNA
<213> ORGANISM: Artificial Sequence
<220> FEATURE:
<223> OTHER INFORMATION: Synthetic probe

<400> SEQUENCE: 16

```
cgatccccgc aatacaccac gattctggat gcgacaggca agattatcgc acctggattc    60
gtcgacactc accgtcatgg ttggcaaacg ttttttaaga ccatggtctc aaacatcact   120
ctgattgagt atttcggccg tttcggggag tcagcttctg caggacgcat caatgctgag   180
caagtatacc ttggtcagct cgccggcctc tatgaatcag tgaacacggg agtcactacg   240
accgttgatc acgcccatca cacttggtca gatgagacgt cctgggctgg tctaaacgcc   300
agtatagaca gcggtgcgcg cgtgttctgg tcttacacct tccatgaagt tgcaaactat   360
accatcgagc agcaactcca aaactatcgc gacattgtga gccgcgcccc acaggcagga   420
tcggctgctg agatcggagt tgcttcgac agcttgaca atggctctgt tgatctggac     480
actatcactg cgatcataga cttagctaag taagtttact cgttactcac cttatgattc    540
aaggtataca ttgttttagt tagtctaacg ttgtgtgttt agagaatcaa atgcctcggt    600
tatcacaacc cacggtggag gaggtgtcta tggaagtagg tgacccgatg tccttttgtt    660
ttgtttgaga ccgcactctt gaacaatggg aactgaccaa atctgcaga cgacaattct     720 ccttcgaccc tacagtccct tggcattctc aacacaagca ttcctgtcgt tatctctcac    780
gcgacgtacg tgactttgcg ggacacaatg ctgttgcgcg agacaaatca gttcgtttct    840
atcacgcccg agtcagagat ggggttcggc ctcggacggc cgacgagcaa catgatcatt    900
gaccaagcct ccttaggtgt tgattcacac gcctttgctt ctagtgatct agtatcccag    960
gcgcgcttgt ttcttcagag tacgcggtca gcagtcaccg atcaactctt caagaaatgg   1020
caggctccta agtcgaaccc tatgagtgtc gttcaggctt ttctccttag cacacgtaac   1080
ggaggccttg cacttcgccg cccagacctt ggtgttctca gtgtcggcgc taaagctgac   1140
gttgtggtgt gggacgggac cagtccgagc ctgctgggct ggcgtgatcc tgtggccgca   1200
atcatccagc actccaatgt cggcgatgtt gagcatgttc tcatcgatgg caaatttgtg   1260
aaaagagatc acaagctggt tgttgggaac tacgcgaatg taaagtctcg gttcctggaa   1320
gtcgcaaacc gcatccagga ggactgggag ctgatccccc gtcccgagct                1370
```

<210> SEQ ID NO 17
<211> LENGTH: 525
<212> TYPE: DNA
<213> ORGANISM: Phoma macrostoma
<220> FEATURE:
<221> NAME/KEY: misc_feature
<222> LOCATION: (42)..(42)
<223> OTHER INFORMATION: n is t or no nucleotide -continued

```
<220> FEATURE:
<221> NAME/KEY: misc_feature
<222> LOCATION: (88)..(88)
<223> OTHER INFORMATION: n is t or no nucleotide
<220> FEATURE:
<221> NAME/KEY: misc_feature
<222> LOCATION: (124)..(124)
<223> OTHER INFORMATION: n is t or no nucleotide

<400> SEQUENCE: 17
kttccgyagk ygaacctgcg gaaggatcat tacctagagt tngyrggcty tgccyrcyay     60
ctcttaccca tgtcttttrm gtacywtncg tttcctcggy gggyycgccc rccgwyygga    120
caanhttaaa ccmyttgyar ttgmaatcag cgtctgaaaa aacwtaatar ttacaacttt    180
caacaacgga tctcttggtt ctggcatcga tgaagaacgc agcgaaatgc gataagtagt    240
gtgaattgca gaattcagtg aatcatcgaa tctttgaacg cacattgcgc cccttggtat    300
tccatggggc atgcctgttc gagcgtcatt tgtaccttca agcyytgctt ggtgttgggt    360
gtttgtctcs cctyygcgyg yagactcgcc tyraaacaat tggcagccgg cgtattgwtt    420
tcggagcgca gyacawytyg crctytgymy tcabmacgrc grcrtccaaa arkhmwttyt    480
tacactcttg acctcggatc aggtagggat acccgctgaa cttaa                   525
```